United States Patent
Mimoto et al.

(10) Patent No.: US 7,816,387 B2
(45) Date of Patent: Oct. 19, 2010

(54) β SECRETASE INHIBITOR

(75) Inventors: Tsutomu Mimoto, Osaka (JP); Satoshi Nojima, Osaka (JP); Naoya Kinomura, Osaka (JP); Yoshiaki Kiso, 15-26, Inaba-cho, Ibaraki-shi, Osaka 567-0827 (JP)

(73) Assignees: Dainippon Sumitomo Pharma Co., Ltd., Osaka-Shi, Osaka (JP); Yoshiaki Kiso, Ibaraki-Shi, Osaka (JP)

( * ) Notice: Subject to any disclaimer, the term of this patent is extended or adjusted under 35 U.S.C. 154(b) by 123 days.

(21) Appl. No.: 11/991,426

(22) PCT Filed: Aug. 31, 2006

(86) PCT No.: PCT/JP2006/317178

§ 371 (c)(1),
(2), (4) Date: Mar. 4, 2008

(87) PCT Pub. No.: WO2007/029587

PCT Pub. Date: Mar. 15, 2007

(65) Prior Publication Data

US 2009/0198056 A1 Aug. 6, 2009

(30) Foreign Application Priority Data

Sep. 5, 2005 (JP) ............................. 2005-256427

(51) Int. Cl.
A61K 31/4168 (2006.01)
A61K 31/4196 (2006.01)
A61K 31/41 (2006.01)
C07D 233/88 (2006.01)
C07D 249/14 (2006.01)
C07D 257/06 (2006.01)

(52) U.S. Cl. .................. 514/381; 514/383; 514/392; 548/262.6; 548/300.1; 548/251

(58) Field of Classification Search .......... 514/383, 514/392, 381; 548/300.1, 262.6, 251
See application file for complete search history.

(56) References Cited

U.S. PATENT DOCUMENTS

2004/0209925 A1* 10/2004 Pulley et al. ............... 514/357
2005/0075327 A1 4/2005 Flohr et al.
2007/0004637 A1 1/2007 Kiso

FOREIGN PATENT DOCUMENTS

| WO | WO-01/00665 | 1/2001 |
| WO | WO-2004/043916 | 5/2004 |
| WO | WO-2004/050609 A1 | 6/2004 |
| WO | WO-2004/076478 | 9/2004 |
| WO | WO-2004/080376 A2 | 9/2004 |
| WO | WO-2005/040126 A1 | 5/2005 |
| WO | WO-2006/036664 A1 | 4/2006 |

OTHER PUBLICATIONS

Neurotherapeutics, 5(3), pp. 399-408 (2008).*
Sinha, Sukanto et al., "Purification and cloning of amyloid precursor protein β-secretase from human brain", *Nature*, Dec. 2, 1999, vol. 402, pp. 537-540.
Ghosh, Arun K. et al., "Design of potent inhibitors for human brain memapsin 2 (β- secretase)", *J. Am. Chem. Soc.*, 2000, vol. 122, pp. 3522-3523.
Kimura, Tooru et al., "KMI-358 and KMI-370, highly potent and small-sized BACE1 inhibitors containing phenylnorstatine", *Bioorganic & Medicinal Chemistry Letters*, 2004, vol. 14, pp. 1527-1531.
Kimura, Tooru et al., "Design and synthesis of highly active Alzheimer's β-secretase (BACE1) inhibitors, KMI-420 and KMI-429, with enhanced chemical stability", *Bioorganic & Medical Chemistry Letters*, 2005, vol. 15, pp. 211-215.

* cited by examiner

*Primary Examiner*—Kamal A Saeed
*Assistant Examiner*—Michael Barker
(74) *Attorney, Agent, or Firm*—Birch, Stewart, Kolasch & Birch, LLP

(57) ABSTRACT

The present invention relates to a compound of the formula (1):

(1)

wherein $R^1$ is group of the formula (2):

(2)

(wherein X is nitrogen atom or $C(R^5)$, Y is nitrogen atom or $C(R^6)$, $R^5$ and $R^6$ are each independently hydrogen atom, etc.) etc., m is 1 to 6, $L^1$ is single bond, etc., $R^2$ is hydrogen atom, substituted or unsubstituted alkyl group, etc., $R^3$ is hydrogen atom, etc., $L^2$ is single bond, etc., $R^4$ is hydrogen atom, substituted or unsubstituted aryl group, etc., or pharmaceutically acceptable salt thereof, being useful for preventing or treating Alzheimer's disease.

10 Claims, No Drawings

β SECRETASE INHIBITOR

This application is the national stage of International Application PCT/JP2006/317178, filed Aug. 31, 2006, which claims priority under 35 USC §119(a)-(d) of Japanese Application No. 2005-256427, filed Sep. 5, 2005.

TECHNICAL FIELD

The present invention relates to an agent for preventing or treating a disease associated with β-secretase, comprising a compound containing hydroxymethylcarbonyl structure or a pharmaceutically acceptable salt thereof as an active ingredient. In particular the invention relates to an agent for preventing or treating Alzheimer's disease.

PRIOR ART

Alzheimer's disease (abbreviated as AD) is a neurodegenerative disease characterized by dementia that insidiously develops in old age and gradually progresses. AD's main symptom is progressing dementia and AD is pathologically characterized by a large amount of senile plaques and neurofibrillary tangles (abbreviated as NFT) observed in the cerebral cortex and hippocampus, and by cerebral atrophy due to deciduation of neuron.

Senile plaque has, as a main component, extracellularly sedimental amyloid fibers comprising of amyloid β-peptide (abbreviated as Aβ). The appearance of senile plaques is extremely specific for AD and aging, and it is a pathological change which is seen at the earliest stage of the disease's progression.

Aβ is produced by cleavage of an amyloid precursor protein (abbreviated as APP) by two kinds of proteases. APP is a type I transmembrane protein consisting of about 700 residues, with Aβ contained in a region ranging from its extracellular region to a transmembrane region. A protease that is involved in the production of Aβ from APP is called "secretase". A secretase that cleaves the amino terminal of Aβ is a "β secretase"; a secretase that cleaves the carboxyl terminal is a "γ secretase"; and a secretase that cleaves the carboxyl terminal of the 16th Lys in the interior of Aβ is an "α secretase". In an amyloidogenic pathway, APP is cleaved with a β secretase to produce a secretion-type APP β (sAPP β) and a carboxyl terminal fragment called β-stub. A γ secretase cleaves this fragment to produce Aβ and a γ-stub.

At present, one of the current mainstream strategies is to target secretase as a point of action for preventing or treating AD. Among them, particular attention has been focused on β and γ secretases since direct effects can be expected. In recent years, considerable progress has been made in the development of β and γ secretase inhibitors. In 1999, it has been reported by some laboratories that β secretase is a β-site APP cleaving enzyme called BACE1 (also referred to as BACE, Asp 2, or memapsin 2).

Since BACE1 is an aspartic acid protease, based on the substrate Transition state concept established by the study on the same class of protease inhibitor such as renin and HIV, various β secretase inhibitors have been reported in recent years. Tang et al. determined the IC$_{50}$ value of 30 nM for a 14 residues peptide in which a hydroxyethylcarbonyl structure was introduced into a substrate cleaving site of β secretase (for example, see Nature, 402, 537-540 (1999)). Ghosh et al. searched various compounds containing hydroxyethylene structure, and found that OM99-2 had strong inhibitory activity (Ki=1.6 nM) (for example, see PCT International Publication WO01/0000665 pamphlet and J. Am. Chem. Soc., 122, 3522-3523 (2000)). Also they found that compounds containing benzoyl structure at amino terminal of hydroxyethylamine derivatives exhibited strong inhibitory activity (for example, see PCT International Publication WO2004/043916 pamphlet and PCT International Publication WO2004/080376 pamphlet). In addition, Kiso, et al. found that compounds containing carboxylic acid or its isostere structure at amino terminal and carboxyl terminal of hydroxymethyl carboxamide structure had strong inhibitory activity (for example, see PCT International Publication WO2004/076478 pamphlet, Bioorg. Med. Chem. Lett., 14, 1527-1531 (2004) and Bioorg. Med. Chem. Lett., 15, 211-215 (2005)).

DISCLOSURE OF INVENTION

Problems to be Solved by Invention

An object of the present invention is to provide an agent for preventing or treating a disease associated with β-secretase, in particular AD.

The present inventors have intensively studied in order to achieve the above-mentioned objects, and have found that a compound containing hydroxymethylcarbonyl structure or a pharmaceutically acceptable salt thereof had an excellent β-secretase inhibitory activity, and have accomplished the present invention.

That is, the present invention relates to the following embodiments:

[1] A compound represented by the general formula (1):

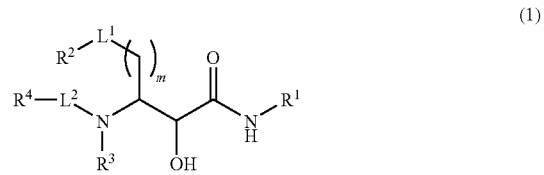

(1)

wherein
R$^1$ is a group of the formula (2):

(2)

wherein X is a nitrogen atom or a group of the formula: C(R$^5$),

Y is a nitrogen atom or a group of the formula: C(R$^6$),

R$^5$ and R$^6$ are each independently a hydrogen atom, a halogen atom, a carboxyl group, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted, saturated or unsaturated aliphatic heterocyclic group, a substituted or unsubstituted aryl group, a substituted or unsubstituted aromatic heterocyclic group, a substituted or unsubstituted alkoxycarbonyl group, or a substituted or unsubstituted amino group, or alternatively R$^5$ and R$^6$ may combine together with the carbon atoms to which they bind, to form a substituted or unsubstituted cyclopentene ring, a substituted or unsubstituted cyclohexene ring, a substituted or unsubstituted benzene ring, or a substituted or unsubstituted pyridine ring; or a group of the formula (3):

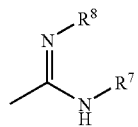
(3)

wherein $R^7$ is a hydrogen atom, a substituted or unsubstituted alkyl group, or a group of the formula: $C(=O)R^9$ or $C(=S)R^9$ (wherein $R^9$ is a substituted or unsubstituted alkyl group), $R^8$ is a hydrogen atom or a substituted or unsubstituted alkyl group, or alternatively $R^7$ and $R^8$ may combine to form a group of the formula: $-[C(R^{10})(R^{11})]_n-$, $-C(=O)[C(R^{10})(R^{11})]_p-$ or $-C(=S)[C(R^{10})(R^{11})]_p-$ (wherein $R^{10}$ and $R^{11}$ are each independently a hydrogen atom or a substituted or unsubstituted alkyl group, n is an integer of 2 to 4 and p is an integer of 1 to 3, or when n or p is more than 1, two or more $R^{10}$ and two or more $R^{11}$ may be each independently the same or different group);

m is an integer of 1 to 6, $L^1$ is a single bond, an oxygen atom or a sulfur atom, $R^2$ is a hydrogen atom, a substituted or unsubstituted alkyl group, a substituted or unsubstituted cycloalkyl group, a substituted or unsubstituted cycloalkenyl group, a substituted or unsubstituted, saturated or unsaturated aliphatic heterocyclic group, a substituted or unsubstituted aryl group, or a substituted or unsubstituted aromatic heterocyclic group, $R^3$ is a hydrogen atom or a substituted or unsubstituted alkyl group, $L^2$ is a single bond or a group selected from the following formulae (a) to (n):

$-[C(R^{12})(R^{13})]_q-$, (a)

$-C(=O)-$, (b)

$-[C(R^{12})(R^{13})]_q-C(=O)-$, (c)

$-O-[C(R^{12})(R^{13})]_q-C(=O)-$, (d)

$-S-[C(R^{12})(R^{13})]_q-C(=O)-$, (e)

$-N(R^{14})-[C(R^{12})(R^{13})]_q-C(=O)-$, (f)

$-[N(R^{14})-C(R^{12})(R^{13})-C(=O)]_r-$, (g)

$-[C(R^{12})(R^{13})]_s-O-C(=O)-$, (h)

$-[C(R^{12})(R^{13})]_s-N(R^{14})-C(=O)-$, (i)

$-[C(R^{12})(R^{13})]_s-N(R^{14})-C(=S)-$, (j)

$-S(=O)_2-$, (k)

$-C(R^{12})=C(R^{13})-C(=O)-$, (l)

$-C(=O)-N(R^{14})-C(R^{12})(R^{13})-C(=O)-$, (m)

$-C(=O)-[C(R^{12})(R^{13})]_q-C(=O)-$ (n)

wherein $R^{12}$, $R^{13}$ and $R^{14}$ are each independently a hydrogen atom or a substituted or unsubstituted alkyl group, q is an integer of 1 to 6, r is 2 or 3, s is an integer of 0 to 6, and when q, r or s is more than 1, two or more $R^{12}$, two or more $R^{13}$ and two or more $R^{14}$ may be each independently the same or different group;

$R^4$ is a hydrogen atom, a substituted or unsubstituted, saturated or unsaturated aliphatic heterocyclic group, a substituted or unsubstituted aryl group, or a substituted or unsubstituted aromatic heterocyclic group, or a pharmaceutically acceptable salt thereof.

[2] The compound as set forth in [1] or a pharmaceutically acceptable salt thereof, wherein $R^2$ is a hydrogen atom, a substituted or unsubstituted cycloalkyl group, a substituted or unsubstituted cycloalkenyl group, a substituted or unsubstituted, saturated or unsaturated aliphatic heterocyclic group, a substituted or unsubstituted aryl group, or a substituted or unsubstituted aromatic heterocyclic group, $L^2$ is a single bond or a group selected from the following formulae (a) to (e) and (i) to (n):

$-[C(R^{12})(R^{13})]_q-$, (a)

$-C(=O)-$, (b)

$-[C(R^{12})(R^{13})]_q-C(=O)-$, (c)

$-O-[C(R^{12})(R^{13})]_q-C(=O)-$, (d)

$-S-[C(R^{12})(R^{13})]_q-C(=O)-$, (e)

$-[C(R^{12})(R^{13})]_s-N(R^{14})-C(=O)-$, (i)

$-[C(R^{12})(R^{13})]_s-N(R^{14})-C(=S)-$, (j)

$-S(=O)_2-$, (k)

$-C(R^{12})=C(R^{13})-C(=O)-$, (l)

$-C(=O)-N(R^{14})-C(R^{12})(R^{13})-C(=O)-$, (m)

$-C(=O)-[C(R^{12})(R^{13})]_q-C(=O)-$ (n)

wherein $R^{12}$, $R^{13}$, $R^{14}$, q and s have the same meanings as defined in [1], and $R^4$ is a substituted or unsubstituted, saturated or unsaturated aliphatic heterocyclic group, a substituted or unsubstituted aryl group, or a substituted or unsubstituted aromatic heterocyclic group.

[3] The compound as set forth in [1] or [2] or a pharmaceutically acceptable salt thereof, wherein $R^1$ is a group of the formula (2):

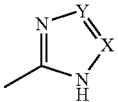
(2)

wherein X and Y have the same meanings as defined in [1].

[4] The compound as set forth in [3] or a pharmaceutically acceptable salt thereof, wherein X is a group of the formula: $C(R^5)$ (wherein $R^5$ has the same meaning as defined in [1]) and Y is a group of the formula: $C(R^6)$ (wherein $R^6$ has the same meaning as defined in [1]).

[5] The compound as set forth in [1] or [2] or a pharmaceutically acceptable salt thereof, wherein $R^1$ is a group of the formula (3):

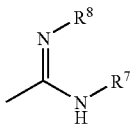

(3)

wherein $R^7$ and $R^8$ have the same meanings as defined in [1].

[6] The compound as set forth in any one of [1] to [5] or a pharmaceutically acceptable salt thereof, wherein m is 1, $L^1$ is a single bond and $R^2$ is a substituted or unsubstituted aryl group.

[7] The compound as set forth in any one of [1] to [6] or a pharmaceutically acceptable salt thereof, wherein $L^2$ is a group of the formula: —C(=O)— and $R^4$ is a substituted or unsubstituted aryl group.

[8] The compound as set forth in any one of [1] to [7] or a pharmaceutically acceptable salt thereof, wherein a compound of the formula (1) is represented by the formula (4):

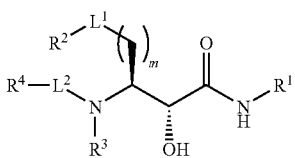

(4)

wherein $R^1$, $R^2$, $R^3$, $R^4$, $L^1$, $L^2$ and m have the same meanings as defined in [1].

[9] A β-secretase inhibitor comprising the compound as set forth in any one of [1] to [8] or a pharmaceutically acceptable salt thereof as an active ingredient.

[10] An agent for preventing or treating Alzheimer's disease, comprising the compound as set forth in any one of [1] to [8] or a pharmaceutically acceptable salt thereof as an active ingredient.

EFFECT OF THE INVENTION

The compound of the present invention has an excellent β-secretase inhibitory activity, and thus is useful for preventing or treating Alzheimer's disease.

BEST MODES FOR CARRYING OUT THE INVENTION

The present invention is explained in more detail below.

Unless defined otherwise, the definition for each group shall also be applied to where said group is a part of another group.

The number of a substituent described herein is not limited specifically as long as possible, and thus includes one or more than 1.

The term "alkyl group" includes, for example, a straight chain or branched chain alkyl group having 1 to 10 carbon atom(s), specifically such as methyl, ethyl, propyl, isopropyl, butyl, isobutyl, sec-butyl, tert-butyl, pentyl, isopentyl, neopentyl, tert-pentyl, 1-methylbutyl, hexyl, heptyl, octyl, nonyl, or decyl group, etc. Preferred alkyl group is an alkyl group having 1 to 6 carbon atom(s).

The "alkenyl group" includes, for example, a straight chain or branched chain alkenyl group having 2 to 6 carbon atoms, specifically such as vinyl, 1-propenyl, allyl (2-propenyl), isopropenyl (1-methylvinyl), 1-butenyl, 2-butenyl, 3-butenyl, 1-methyl-1-propenyl, 1-methyl-2-propenyl, 2-methylallyl, 1-ethylvinyl, 1-pentenyl, or 1-hexenyl group, etc. Preferred alkenyl group is an alkenyl group having 2 to 4 carbon atoms.

The "alkynyl group" includes, for example, a straight chain or branched chain alkynyl group having 2 to 6 carbon atoms, specifically such as ethynyl, 1-propynyl, 2-propynyl, 1-butynyl, 1-methyl-2-propynyl, 2-butynyl, 3-butynyl, 1-pentynyl, or 1-hexynyl group, etc. Preferred alkynyl group is an alkynyl group having 2 to 4 carbon atoms.

The term "cycloalkyl group" includes, for example, a saturated cycloalkyl group having 3 to 8 carbon atoms, specifically such as cyclopropyl, cyclobutyl, cyclopentyl, cyclohexyl, cycloheptyl, or cyclooctyl. Preferred cycloalkyl group is a saturated cycloalkyl group having 4 to 6 carbon atoms.

The term "cycloalkenyl group" includes, for example, a cycloalkenyl group having 4 to 8 carbon atoms, specifically such as cyclobutenyl, cyclopentenyl, cyclohexenyl, cycloheptenyl, or cyclooctenyl group, with a position for binding on the ring be not limited specifically. Preferred cycloalkenyl group is a cycloalkenyl group having 4 to 6 carbon atoms.

The term "saturated aliphatic heterocyclic group" includes, for example, a 4- to 8-membered saturated aliphatic heterocyclic group having 1 to 3 heteroatom(s) selected from the group consisting of 0 to 3 nitrogen atom(s), 0 to 2 oxygen atom(s) and 0 to 2 sulfur atom(s), with a position for binding on the ring be not limited specifically as long as being chemically stable. Specifical examples include azetidinyl, pyrrolidinyl, piperidyl, piperidino, piperazinyl, azepanyl, azocanyl, tetrahydrofuryl, tetrahydrothienyl, tetrahydropyranyl, morpholinyl, morpholino, thiomorpholinyl, thiomorpholino, 1,4-dioxanyl, or thiazolidinyl group, etc.

The term "unsaturated aliphatic heterocyclic group" includes, for example, a 5- to 8-membered unsaturated aliphatic heterocyclic group having 1 to 3 heteroatom(s) selected from the group consisting of 0 to 3 nitrogen atom(s), 0 to 2 oxygen atom(s) and 0 to 2 sulfur atom(s), and further having 1 or 2 double bond(s), with a position for binding on the ring be not limited specifically as long as being chemically stable. Specifical examples include 2-pyrrolinyl, 3-pyrrolinyl, 2-imidazolinyl, 3-imidazolinyl, 2-pyrazolinyl, or 3-pyrazolinyl group, etc.

The term "aryl group" includes, for example, an aryl group having 6 to 10 carbon atoms, specifically such as phenyl, 1-naphthyl, or 2-naphthyl group etc.

The term "aromatic heterocyclic group", also referred as heteroaryl group, includes, for example, a 5- to 6-membered monocyclic aromatic heterocyclic group or a 9- to 10-membered bicyclic aromatic heterocyclic group having 1 to 4 heteroatom(s) selected from the group consisting of 0 to 4 nitrogen atom(s), 0 to 2 oxygen atom(s) and 0 to 2 sulfur atom(s), with a position for binding on the ring be not limited specifically as long as being chemically stable. Specifical examples include furyl, thienyl, pyrrolyl, oxazolyl, thiazolyl, imidazolyl, pyrazolyl, furazanyl, triazolyl, pyridyl, pyrimidinyl, pyrazinyl, indolyl, quinolyl, isoquinolyl, quinazolinyl, or imidazopyridinyl group, etc.

The term "halogen atom" includes fluorine atom, chlorine atom, bromine atom, or iodine atom.

The term "alkoxy group" includes, for example, a straight chain or branched chain alkoxy group having 1 to 10 carbon atom(s), specifically such as methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, hexyloxy, heptyloxy, octyloxy, nonyloxy, or decyloxy group, etc. Preferred alkoxy group is an alkoxy group having 1 to 6 carbon atom(s).

The term "alkanoyl group", also referred as acyl group or alkylcarbonyl group, includes, for example, a straight chain or branched chain alkanoyl group having 1 to 10 carbon atom(s), specifically such as formyl, acetyl, propionyl, butyryl, isobutyryl, valeryl, isovaleryl, pivaloyl, hexanoyl, heptanoyl, octanoyl, nonanoyl, or decanoyl group, etc. Preferred alkanoyl group is an alkanoyl group having 1 to 6 carbon atom(s).

The term "alkanoyloxy group" includes, for example, a straight chain or branched chain alkanoyloxy group having 1 to 10 carbon atom(s), specifically such as formyloxy, acetyloxy, propionyloxy, butyryloxy, isobutyryloxy, valeryloxy, isovaleryloxy, pivaloyloxy, hexanoyloxy, heptanoyloxy, octanoyloxy, nonanoyloxy, or decanoyloxy group, etc. Preferred alkanoyloxy group is an alkanoyloxy group having 1 to 6 carbon atom(s).

The term "alkoxycarbonyl group" includes, for example, a straight chain or branched chain alkoxycarbonyl group having 2 to 11 carbon atom(s), specifically such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, 1-methylbutoxycarbonyl, hexyloxycarbonyl, heptyloxycarbonyl, octyloxycarbonyl, nonyloxycarbonyl, or decyloxycarbonyl group, etc. Preferred alkoxycarbonyl group is an alkoxycarbonyl group having 2 to 6 carbon atoms.

The term "alkylthio group" includes, for example, a straight chain or branched chain alkylthio group having 1 to 10 carbon atom(s), specifically such as methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, hexylthio, heptylthio, octylthio, nonylthio, or decylthio group, etc. Preferred alkylthio group is an alkylthio group having 1 to 6 carbon atom(s).

The term "alkylsulfinyl group" includes, for example, a straight chain or branched chain alkylsulfinyl group having 1 to 10 carbon atom(s), specifically such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, tert-pentylsulfinyl, 1-methylbutylsulfinyl, hexylsulfinyl, heptylsulfinyl, octylsulfinyl, nonylsulfinyl, or decylsulfinyl group, etc. Preferred alkylsulfinyl group is an alkylsulfinyl group having 1 to 6 carbon atom(s).

The term "alkylsulfonyl group" includes, for example, a straight chain or branched chain alkylsulfonyl group having 1 to 10 carbon atom(s), specifically such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, 1-methylbutylsulfonyl, hexylsulfonyl, heptylsulfonyl, octylsulfonyl, nonylsulfonyl, or decylsulfonyl group, etc. Preferred alkylsulfonyl group is an alkylsulfonyl group having 1 to 6 carbon atom(s).

The term "aroyl group", also referred as arylcarbonyl group, includes, for example, a carbonyl group to which aryl group having 6 to 10 carbon atoms binds, specifically such as benzoyl, 1-naphthoy, or 2-naphthoy group, etc.

The "aryl moiety" in the terms "arylsulfonyl group" and "aryloxy group" has the same meanings as that of the above aryl group.

The "heteroaryl moiety" in the terms "heteroarylcarbonyl group" and "heteroarylsulfonyl group" has the same meanings as that of the above heteroaryl group.

When the "alkyl group", "alkenyl group", or "alkynyl group" is substituted, the substituent is selected from the group consisting of the following groups: (i) to (v), and said "alkyl group", "alkenyl group", or "alkynyl group" may be substituted with 1 to 3 same or different substituent(s):

(i) a halogen atom, a hydroxy group, a carboxyl group, or a cyano group;

(ii) an amino group optionally substituted with 1 or 2 same or different alkyl group(s), a carbamoyl group optionally substituted with 1 or 2 same or different alkyl group(s), or a sulfamoyl group optionally substituted with 1 or 2 same or different alkyl group(s);

(iii) an alkoxy group, an alkanoyl group, an alkanoyloxy group, an alkoxycarbonyl group, an alkylthio group, an alkylsulfinyl group, or an alkylsulfonyl group

[these groups may be substituted with substituent(s) selected from the group consisting of a halogen atom, a hydroxy group, a carboxyl group, or an amino group optionally substituted with 1 or 2 same or different alkyl group(s), and an optionally substituted aryl group, and the substituent of said aryl group includes, for example, a halogen atom, an alkyl group, a hydroxy group, a carboxyl group, an alkoxy group, an alkoxycarbonyl group, a nitro group, a cyano group, and a carbamoyl group];

(iv) a cycloalkyl group, a cycloalkenyl group, or a saturated or unsaturated aliphatic heterocyclic group

[these groups may be substituted with substituent(s) selected from the group consisting of a halogen atom, a hydroxy group, a carboxyl group, an amino group optionally substituted with 1 or 2 same or different alkyl group(s), an alkoxy group, an alkoxycarbonyl group, an optionally substituted alkyl group, and an optionally substituted aryl group, and the substituent of said alkyl group includes, for example, a halogen atom, a hydroxy group, a carboxyl group and an alkoxy group, and the substituent of said aryl group includes, for example, a halogen atom, an alkyl group, a hydroxy group, a carboxyl group, an alkoxy group, an alkoxycarbonyl group, a nitro group, a cyano group and a carbamoyl group];

(v) an aryl group or an aromatic heterocyclic group

[these groups may be substituted with substituent(s) selected from the group consisting of a halogen atom, a hydroxy group, a carboxyl group, an amino group optionally substituted with 1 or 2 same or different alkyl group(s), an alkoxy group, an alkoxycarbonyl group, an optionally substituted alkyl group, and an optionally substituted aryl group, and the substituent of said alkyl group includes a halogen atom, a hydroxy group, a carboxyl group, and an alkoxy group, and the substituent of said aryl group includes, for example, a halogen atom, an alkyl group, a hydroxy group, a carboxyl group, an alkoxy group, an alkoxycarbonyl group, a nitro group, a cyano group and a carbamoyl group].

When the "cycloalkyl group", "cycloalkenyl group", or "saturated or unsaturated aliphatic heterocyclic group" is substituted, the substituent is selected from the group consisting of the following groups: (vi) to (x), and said "cycloalkyl group", "cycloalkenyl group", or "saturated or unsaturated aliphatic heterocyclic group" may be substituted with 1 to 3 same or different substituent(s):

(vi) a halogen atom, a hydroxy group, a carboxyl group, a cyano group, an oxo group, or a thioxo group;

(vii) (1) an amino group optionally substituted with 1 or 2 same or different substituent(s)

[said substituent includes, for example, an optionally substituted alkyl group, an optionally substituted alkanoyl group, an optionally substituted aroyl group, an optionally substituted heteroarylcarbonyl group, an optionally substituted alkylsulfonyl group, an optionally substituted arylsulfonyl group, or an optionally substituted heteroarylsulfonyl group. The substituents of an alkyl group, an alkanoyl group and an alkylsulfonyl group which are optionally substituted include, for example, a halogen atom, a hydroxy group, a carboxyl group, an alkoxy group, an aryl group and an aromatic heterocyclic group. The substituents of an aroyl group, a heteroarylcarbonyl group, an arylsulfonyl group and a heteroarylsulfonyl group which are optionally substituted include, for example, a halogen atom, a hydroxy group, a carboxyl group, an alkoxy group and an alkyl group];

(vii) (2) a carbamoyl group optionally substituted with 1 or 2 same or different alkyl group(s), or a sulfamoyl group optionally substituted with 1 or 2 same or different alkyl group(s);

(viii) an alkyl group, an alkoxy group, an alkanoyl group, an alkanoyloxy group, an alkoxycarbonyl group, an alkylthio group, an alkylsulfinyl group, or an alkylsulfonyl group

[these groups may be substituted with substituent(s) selected from the group consisting of a halogen atom, a hydroxy group, a carboxyl group, an alkoxy group, an optionally substituted aryl group, and an amino group optionally substituted with 1 or 2 same or different alkyl group(s), and the substituent of said aryl group includes, for example, a halogen atom, an alkyl group, a hydroxy group, a carboxyl group and an alkoxy group];

(ix) a cycloalkyl group, a cycloalkenyl group, or a saturated or unsaturated aliphatic heterocyclic group

[these groups may be substituted with substituent(s) selected from the group consisting of a halogen atom, a hydroxy group, a carboxyl group, an amino group optionally substituted with 1 or 2 same or different alkyl group(s), an alkoxy group, an alkoxycarbonyl group, an optionally substituted alkyl group, and an optionally substituted aryl group, and the substituent of said alkyl group includes, for example, a halogen atom, a hydroxy group, a carboxyl group and an alkoxy group, and the substituent of said aryl group includes, for example, a halogen atom, an alkyl group, a hydroxy group, a carboxyl group and an alkoxy group];

(x) an aryl group, an aromatic heterocyclic group, or an aryloxy group

[these groups may be substituted with substituent(s) selected from the group consisting of a halogen atom, a hydroxy group, a carboxyl group, an amino group optionally substituted with 1 or 2 same or different alkyl group(s), an alkoxy group, an alkoxycarbonyl group, an optionally substituted alkyl group, and an optionally substituted aryl group, and the substituent of said alkyl group includes, for example, a halogen atom, a hydroxy group, a carboxyl group and an alkoxy group, and the substituent of said aryl group includes, for example, a halogen atom, an alkyl group, a hydroxy group, a carboxyl group and an alkoxy group].

When the "aryl group" or "aromatic heterocyclic group" is substituted, the substituent is selected from the group consisting of the following groups: (xi) to (xvi), and said "aryl group" or "aromatic heterocyclic group" may be substituted with 1 to 5 same or different substituent(s):

(xi) a halogen atom, a hydroxy group, a carboxyl group, a cyano group, or a nitro group;

(xii) an amino group optionally substituted with 1 or 2 same or different substituent(s)

[said substituent includes, for example, an optionally substituted alkyl group, an optionally substituted aryl group, an optionally substituted alkanoyl group, an optionally substituted aroyl group, an optionally substituted heteroarylcarbonyl group, an optionally substituted alkylsulfonyl group, an optionally substituted arylsulfonyl group, or an optionally substituted heteroarylsulfonyl group. The substituents of an alkyl group, an alkanoyl group and an alkylsulfonyl which are optionally substituted include, for example, a halogen atom, a hydroxy group, a carboxyl group, an alkoxy group, an aryl group and an aromatic heterocyclic group. The substituents of an aryl group, an aroyl group, a heteroarylcarbonyl group, an arylsulfonyl group and a heteroarylsulfonyl group which are optionally substituted include, for example, a halogen atom, a hydroxy group, a carboxyl group, an alkoxy group and an alkyl group];

(xiii) a carbamoyl group optionally substituted with 1 or 2 same or different alkyl group(s) that is optionally substituted, or a sulfamoyl group optionally substituted with 1 or 2 same or different alkyl group(s) that is optionally substituted

[the substituents of an optionally substituted alkyl group in these groups include, for example, a halogen atom, a hydroxy group, a carboxyl group, an alkoxy group, an aryl group, an aromatic heterocyclic group (said aryl group or aromatic heterocyclic group may be substituted with a halogen atom, a hydroxy group, a carboxyl group, an alkyl group, or an alkoxy group)];

(xiv) an alkyl group, an alkenyl group, an alkynyl group, an alkoxy group, an alkanoyl group, an alkanoyloxy group, an alkoxycarbonyl group, an alkylthio group, an alkylsulfinyl group, or an alkylsulfonyl group

[these groups may be substituted with a substituent selected from the group consisting of a halogen atom, a hydroxy group, a carboxyl group, an alkoxy group, a cycloalkyl group optionally substituted with alkyl group, an amino group optionally substituted with 1 or 2 same or different alkyl group(s), and an aryl group (said aryl group may be substituted with a halogen atom, a hydroxy group, a carboxyl group, an alkyl group, or an alkoxy group)];

(xv) a cycloalkyl group, a cycloalkenyl group or a saturated or unsaturated aliphatic heterocyclic group

[these groups may be substituted with a substituent selected from the group consisting of a halogen atom, a hydroxy group, a carboxyl group, an oxo group, a thioxo group, an amino group optionally substituted with 1 or 2 same or different alkyl group(s), an alkoxy group, an alkoxycarbonyl group, an optionally substituted alkyl group, and an optionally substituted aryl group. The substituent of said alkyl group includes, for example, a halogen atom, a hydroxy group, a carboxyl group and an alkoxy group. The substituent of said aryl group includes, for example, a halogen atom, an alkyl group, a hydroxy group, a carboxyl group, and an alkoxy group];

(xvi) an aryl group or an aromatic heterocyclic group

[these groups may be substituted with a substituent selected from the group consisting of a halogen atom, a hydroxy group, a carboxyl group, an amino group optionally substituted with 1 or 2 same or different alkyl group(s), an alkoxy group, an alkoxycarbonyl group, an optionally substituted alkyl group, and an optionally substituted aryl group. The substituent of said alkyl group includes, for example, a halogen atom, a hydroxy group, a carboxyl group and an alkoxy group. The substituent of said aryl group includes, for example, a halogen atom, an alkyl group, a hydroxy group, a carboxyl group, and an alkoxy group].

When "amino group" for $R^5$ and $R^6$ is substituted, the substituent is selected from the following group (xvii) and the "amino group" may be substituted with 1 to 2 same or different substituent(s):

(xvii) an alkyl group, an alkanoyl group, or an alkylsulfonyl group

[these group may be substituted with a substituent selected from the group consisting of a halogen atom, a hydroxy group, a carboxyl group and an alkoxy group].

When $L^2$ is a group of the following formulae (a) to (n):

—[C($R^{12}$)($R^{13}$)]$_q$—, (a)

—C(=O)—, (b)

—[C($R^{12}$)($R^{13}$)]$_q$—C(=O)—, (c)

—O—[C($R^{12}$)($R^{13}$)]$_q$—C(=O)—, (d)

—S—[C($R^{12}$)($R^{13}$)]$_q$—C(=O)—, (e)

—N($R^{14}$)—[C($R^{12}$)($R^{13}$)]$_q$—C(=O)—, (f)

—[N($R^{14}$)—C($R^{12}$)($R^{13}$)—C(=O)]$_r$—, (g)

—[C($R^{12}$)($R^{13}$)]$_s$—O—C(=O)—, (h)

—[C($R^{12}$)($R^{13}$)]$_s$—N($R^{14}$)—C(=O)—, (i)

—[C($R^{12}$)($R^{13}$)]$_s$—N($R^{14}$)—C(=S)—, (j)

—S(=O)$_2$—, (k)

—C($R^{12}$)=C($R^{13}$)—C(=O)—, (l)

—C(=O)—N($R^{14}$)—C($R^{12}$)($R^{13}$)—C(=O)—, (m)

—C(=O)—[C($R^{12}$)($R^{13}$)]$_q$—C(=O)— (n)

then $R^4$ binds to a left side of the formulae (a) to (n) and a nitrogen atom binds to a right side of the above formulae. For other definitions in the above, when different products forms if the divalent groups bind the different direction, it shall be understand that the divalent groups bind to in the direction as indicated in a structural formula, unless defined otherwise. When q, r or s is more than 1, two or more $R^{12}$, two or more $R^{13}$ and two or more $R^{14}$ may be each independently the same or different group. A geometrical isomerism of a double bond in the formula (1) includes, for example, a cis form, a trans form and a mixture thereof.

In the formula (2), X is preferably a group of the formula: C($R^5$) and Y is preferably a group of the formula: C($R^6$). Namely a group of the formula (5):

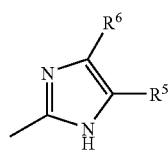

(5)

(wherein $R^5$ and $R^6$ have the same meanings as aforementioned) is preferred. In the formula (5), $R^5$ and $R^6$ are preferably each independently a hydrogen atom, or a substituted or unsubstituted alkyl group.

In the formula (2) and the formula (5), $R^5$ and $R^6$ may combine together with the carbon atoms to which they bind, to form a cyclopentene ring, a cyclohexene ring, a benzene ring, or a pyridine ring, specifically such as a group of the formulae (6) to (12):

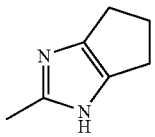

(6)

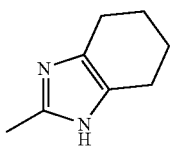

(7)

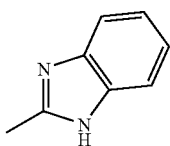

(8)

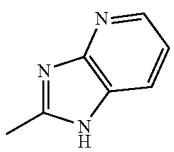

(9)

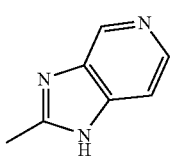

(10)

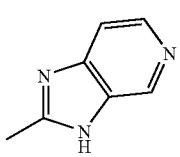

(11)

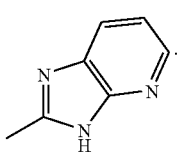

(12)

The carbon atom on the ring in the group represented by the above formulae (6) to (12) may be substituted and said substituent is selected from the group consisting of the following groups (xvii) to (xx) and the carbon atom may be substituted with 1 to 4 same or different substituent(s):

(xvii) a halogen atom, a hydroxy group, a carboxyl group, a cyano group, or a nitro group;

(xviii) an amino group optionally substituted with 1 or 2 same or different substituent(s)

[said substituent includes, for example, an optionally substituted alkyl group, an optionally substituted alkanoyl group, an optionally substituted aroyl group, an optionally substituted heteroarylcarbonyl group, an optionally substituted alkylsulfonyl group, an optionally substituted arylsulfonyl group, or an optionally substituted heteroarylsulfonyl group. The substituents of an alkyl group, an alkanoyl group and an alkylsulfonyl which are optionally substituted include, for example, a halogen atom, a hydroxy group, a carboxyl group, an alkoxy group, an aryl group or an aromatic heterocyclic group. The substituent of an aroyl group, a heteroarylcarbonyl group, an arylsulfonyl group or a heteroarylsulfonyl group which are optionally substituted include, for example, a halogen atom, a hydroxy group, a carboxyl group and an alkoxy group];

(xiv) a carbamoyl group optionally substituted with 1 or 2 same or different alkyl group(s) that is optionally substituted, or a sulfamoyl group optionally substituted with 1 or 2 same or different alkyl group(s) that is optionally substituted

[the substituent of said optionally substituted alkyl group in these groups include, for example, a halogen atom, a hydroxy group, a carboxyl group, an alkoxy group, an aryl group and an aromatic heterocyclic group];

(xx) an alkyl group, an alkenyl group, an alkynyl group, an alkoxy group, an alkanoyl group, an alkanoyloxy group, an alkoxycarbonyl group, an alkylthio group, an alkylsulfinyl group, or an alkylsulfonyl group

[these groups may be substituted with a substituent selected from the group consisting of a halogen atom, a hydroxy group, a carboxyl group, an alkoxy group, a cycloalkyl group optionally substituted with an alkyl group, an amino group optionally substituted with 1 or 2 same or different alkyl group(s), and an aryl group].

When in the formula (3), $R^7$ and $R^8$ combine each other to form a group of the formula: $—[C(R^{10})(R^{11})]_n—$, $—C(=O)[C(R^{10})(R^{11})]_p—$ or $—C(=S)[C(R^{10})(R^{11})]_p—$, the formula (3) specifically represents any one of the formula (13) to the formula (15):

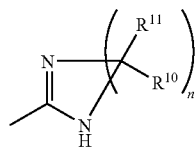

(13)

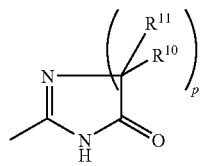

(14)

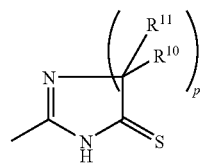

(15)

(wherein $R^{10}$, $R^{11}$, n and p have the same meanings as aforementioned). When n or p is more than 1, two or more $R^{10}$ and two or more $R^{11}$ may be each independently the same or different group.

In the formula (1), $R^4$ is preferably a substituted aryl group and the substituent of said aryl group include, for example, those as aforementioned. When said aryl group is substituted, the aryl group may be substituted with 1 to 5, preferably 1 to 3, more preferably 1 or 2 same or different substituent(s).

Specifical embodiment of the compound of the formula (1) includes, for example, the compound wherein $L^2$ is a carbonyl (C=O) and $R^4$ is the following formula (16):

(16)

(wherein $R^{15}$ is the same substituents as the substituents of the substituted aryl group aforementioned).

The present compound of the formula (1) can be prepared using an intermediate that can be prepared from a commercially available compound or a well-known compound by a combination of well-known methods, according to the following schemes.

The compound of the formula (1) wherein $L^2$ is a group of the formulae (b) to (g) can be prepared, for example, by a method in scheme 1.

[Schem 1]

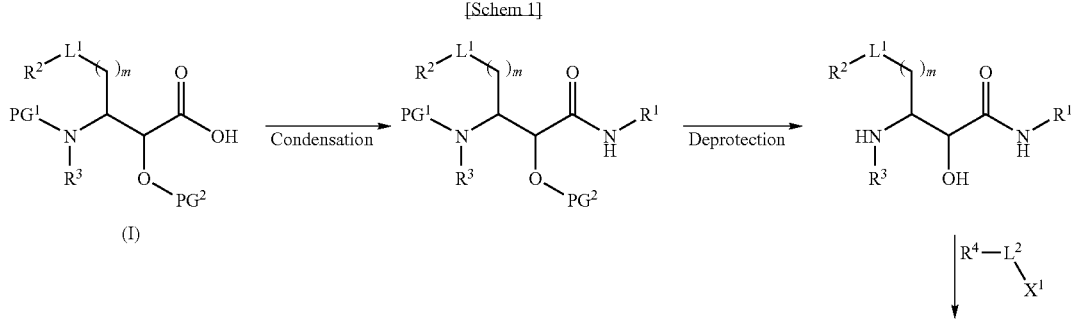

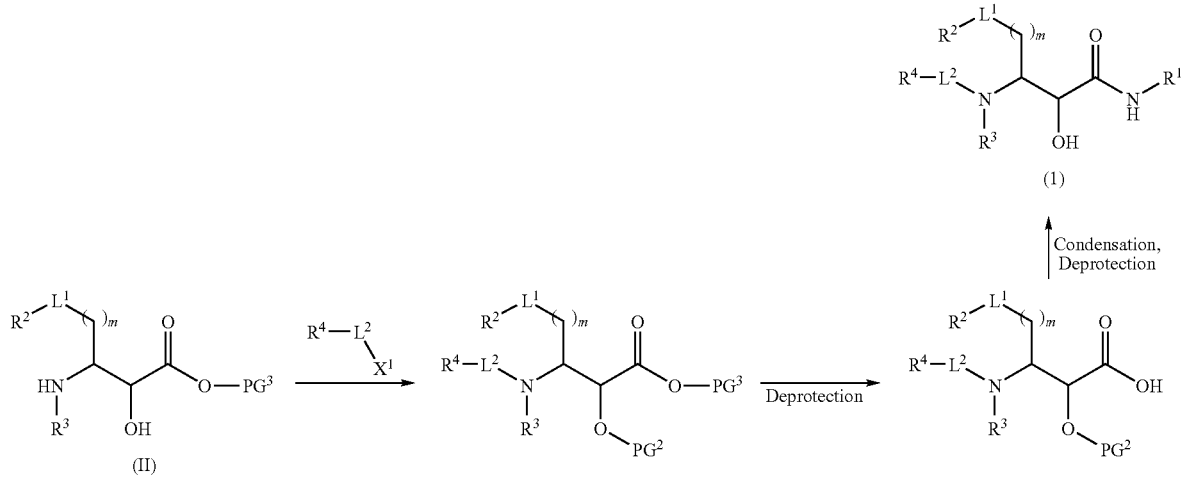

[wherein $R^1$, $R^2$, $R^3$, $R^4$, $L^1$, $L^2$ and m have the same meanings as aforementioned. $X^1$ is a leaving group or a hydroxy group. $PG^1$ is a protecting group of amino group, $PG^2$ is a protecting group of hydroxy group and $PG^3$ is a protecting group of carboxyl group]

In the scheme 1, a formation of an amide bond in the compound wherein $L^2$ is a group of the formulae (b) to (g) can be prepared by the method which is conventionally used in peptide chemistry, for example, the method described in "The Peptides", vol. 1, by Schroder and Luhke, Academic Press, New York, U.S.A (1966), and "Basis and Experiment of Peptide Synthesis" by Nobuo Izumiya, et al., Maruzen (1985), specifically such as an azide, acid chloride, acid anhydride, carbodiimide, carbodiimide-additive, active ester, carbonylimidazole, redox, or enzyme method, and a method using Woodward's reagent K. A condensation is usually performed in a solvent. Examples of solvents include, for example, chloroform, dichloromethane, ethyl acetate, N,N-dimethylformamide, dimethyl sulfoxide, pyridine, dioxane, tetrahydrofuran, N-methylpyrrolidone, acetonitrile, water, methanol, etc., and a mixed solvent thereof. The condensation can be carried out at a temperature of a range of −30° C. to 50° C. as in conventional cases.

The compound wherein $L^2$ is a group of the formulae (h) to (k) can be prepared by a condensation using the corresponding chloroformate, isocyanate, isothiocyanate, or sulfonyl halide to give the desired compounds.

In the scheme 1, the "leaving group" includes, for example, a halogen atom such as bromine atom, etc., or a sulfonyloxy group such as methanesulfonyloxy group or p-toluenesulfonyloxy group, etc., and the like.

In the scheme 1, a functional group not involved in the condensation for each unit can be protected with a protecting group which is usually used in organic chemistry, such as those described in "Protective Groups in Organic Synthesis", by Green, John Wiley & Sons, Inc. (1981), etc.

Examples of the "protecting group of an amino group" include, for example, an urethane type protecting group such as tert-butoxycarbonyl or benzyloxycarbonyl group, as well as a protecting group known to those skilled in the art, such as trityl, tosyl, phthaloyl, formyl, or acetyl group.

Examples of the "protecting group of a carboxyl group" include, for example, a protecting group known to those skilled in the art, such as methyl, ethyl, tert-butyl, or benzyl group.

Examples of the "protecting group of a hydroxy group" include, for example, a protecting group known to those skilled in the art, such as tert-butyl, benzyl, acetyl, methoxymethyl, tetrahydropyranyl (THP) group, or silyl group such as t-butyldimethylsilyl group.

The technique of protection and deprotection can be used by the method described in the aforementioned "Protective Groups in Organic Synthesis".

The compound of the formula (1) wherein $L^2$ is a single bond can be prepared the following method; that is, the bromide of $R^4$—Br is reacted by mixing with the compound (III) in which a hydroxy group or a carboxylic acid is protected, in a solvent such as toluene, N,N-dimethylformamide or dioxane, etc., in the presence of a palladium catalyst such as palladium(II) acetate or tris(dibenzylideneacetone)dipalladium(0), etc., and a ligand such as (R)-(+)-2,2'-bis(diphenylphosphino)-1,1'-binaphthyl or 4,5-bis(diphenylphosphino)-9,9-dimethylxanthine, etc., and a base such as cesium carbonate, etc., at a temperature of a range of room temperature to 200° C. to give the compound of the formula (IV), and the resulting compound of the formula (IV) is subjected to a condensation and a deprotection by a similar method as those in the aforementioned scheme 1 to give the desired compound.

[Scheme 2]

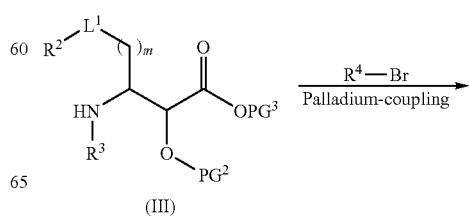

(III)

-continued

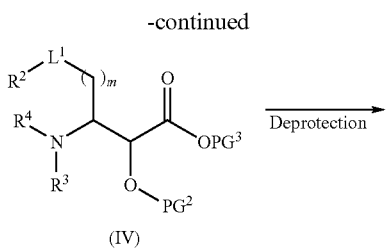
(IV)

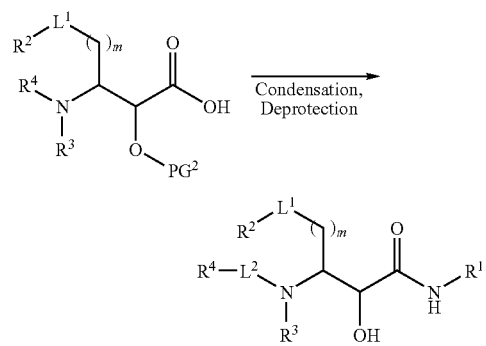

[wherein $R^1$, $R^2$, $R^3$, $R^4$, $L^1$, $L^2$, m, $PG^2$ and $PG^3$ have the same meanings as aforementioned]

The compound of the formula (1) wherein $L^2$ is a group of (a) can be prepared by the following method: that is, the compound of a formula (V) wherein a hydroxy group and a carboxylic acid are protected, is subjected to a reductive alkylation with a reducing reagent such as sodium borohydride, sodium triacetoxyborohydride, or sodium cyanoborohydride, etc. and a carbonyl compound such as aldehyde or ketone, etc., in a solvent such as chloroform, dichloromethane, N,N-dimethylformamide, dimethylsulfoxide, pyridine, dioxane, tetrahydrofuran, N-methylpyrrolidone, acetonitrile, water, methanol, etc., or a mixed solvent thereof at −50° C. to 50° C. to give the compound of the formula (VI), and the resulting compound of the formula (VI) is subjected to a condensation and a deprotection by a similar method as those in the aforementioned scheme 1 to give the desired compound.

[Scheme 3]

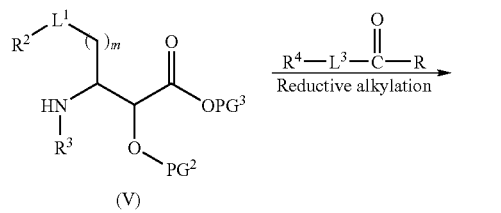
(V)

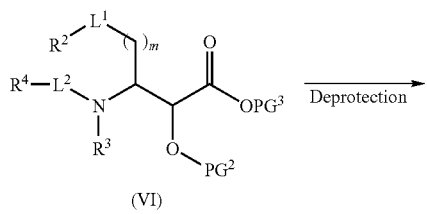
(VI)

-continued

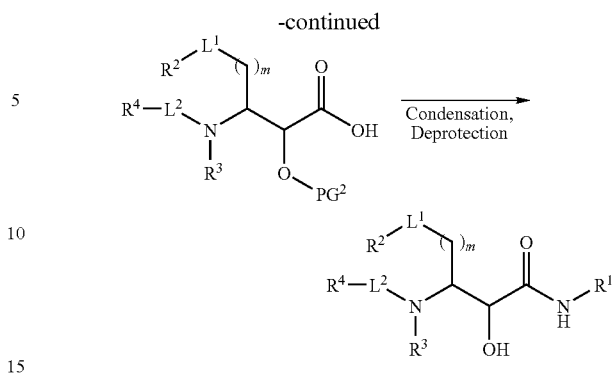

[wherein $R^1$, $R^2$, $R^3$, $R^4$, $L^1$, $L^2$, m, $PG^2$ and $PG^3$ have the same meanings as aforementioned]

A α-hydroxy-β-amino acid derivatives (I) and (II) as a key intermediate of the present invention can be prepared by a well-known method (R. Nishizawa et al., J. Med. Chem., 20, 510 (1977); Umezawa et al., JP-A-56-90050; W. Yuan et al., J. Med. Chem., 36, 211 (1993); Peracini, et al., JP-A-02-28144, etc.). For example, as shown in the following scheme 4, a N-protected aminoaldehyde derivative prepared by a conventional method is reacted with a hydrogen cyanide equivalent such as sodium cyanide, potassium cyanide, trimethylsilyl cyanide, or acetone cyanohydrin, etc., in chloroform, dichloromethane, ethyl acetate, dioxane, tetrahydrofuran, acetonitrile, water, methanol, etc., or a mixed solvent thereof to give the cyanohydrin derivative, and the resulting cyanohydrin derivative is subjected to a hydrolysis under an acidic condition such as hydrochloric acid or sulfuric acid, etc., in dioxane, tetrahydrofuran, water or a mixed solvent thereof to derive desired α-hydroxy-β-amino acids. The resulting α-hydroxy-β-amino acids can be reacted with an amino protecting reagent such as di-tert-butyl dicarbonate or benzyl chloroformate, etc., which is conventionally used, in dioxane, tetrahydrofuran, water, or a mixed solvent thereof in the presence of a base, for example, an organic base such as triethylamine or diisopropylethylamine, etc., or an inorganic base such as sodium hydroxide, potassium hydroxide, sodium carbonate or potassium carbonate, etc., to derive to the N-protected α-hydroxy-β-amino acid. Subsequently the N-protected α-hydroxy-β-amino acid can be reacted with dihydropyran, etc., in a solvent such as dioxane or tetrahydrofuran, etc., in the presence of a catalyst such as p-toluenesulfonic acid pyridinium salt, etc., to derive to a hydroxy group-protecting product (I). On the other hand, the N-protected α-hydroxy-β-amino acid can be treated with sulfuric acid or thionyl chloride, etc., in an appropriate alcoholic solvent such as methanol, ethanol or propanol, etc., to derive to an ester protecting product (II).

[Scheme 4]

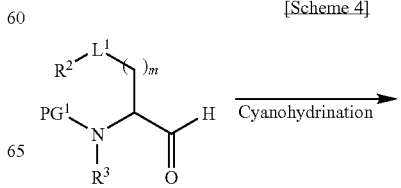

-continued

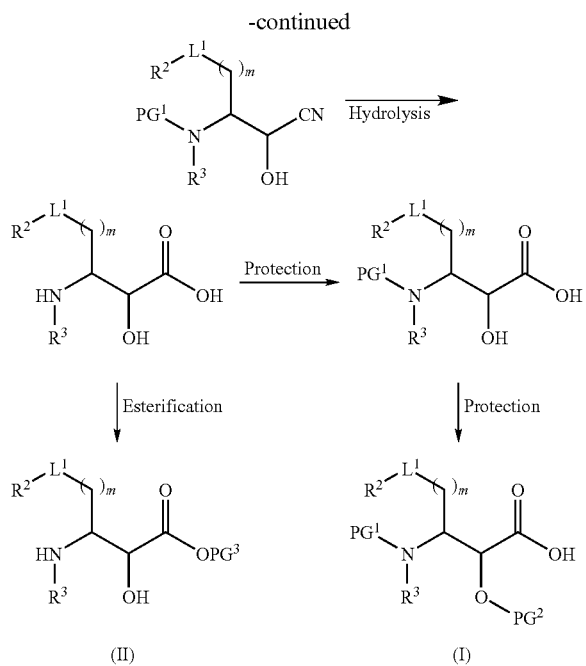

[wherein $R^1$, $R^2$, $R^3$, $R^4$, $L^1$, $L^2$, m, $PG^1$, $PG^2$ and $PG^3$ have the same meanings as aforementioned]

The compound of the formula (1) wherein $R^1$ is a group of the formula (5):

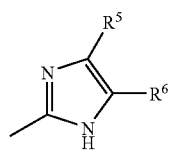

(5)

(wherein $R^5$ and $R^6$ have the same meanings as aforementioned) can be prepared by condensing a 2-aminoimidazole derivative (VII) (which is prepared by a known synthetic method of 2-aminoimidazole, for example, as those shown in Scheme 5 (T. L. Little, et al., J. Org. Chem., 1994, 59, 7299-7305)) by a method shown in scheme 1.

The cyclic reaction shown in the following scheme 5 can be usually carried out by mixing an acetylguanidine with α-haloketone derivative in an appropriate solvent (for example, chloroform, dichloromethane, ethyl acetate, N,N-dimethylformamide, dimethylsulfoxide, pyridine, dioxane, tetrahydrofuran, N-methylpyrrolidone, acetonitrile) at a temperature of a range of room temperature to 100° C. Subsequently a deprotection step can be carried out by treating with an acid such as hydrochloric acid, sulfuric acid, or alkylsulfonic acid, etc., or a base such as hydrazine, etc., in an alcohol such as methanol, ethanol or propanol, etc., at a temperature of a range of room temperature to 100° C.

[Scheme 5]

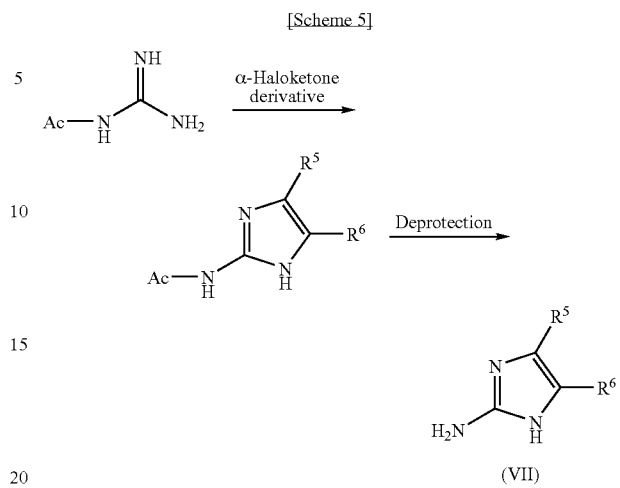

(wherein $R^5$ and $R^6$ have the same meanings as aforementioned)

This cyclic reaction can also be carried out by the following scheme 6 which is different from scheme 5. N-benzyloxycarbonyl guanidine, α-haloketone derivative and an appropriate base (for example, triethylamine or diisopropylethylamine) can be mixed in an appropriate solvent (for example, chloroform, dichloromethane, ethyl acetate, N,N-dimethylformamide, dimethylsulfoxide, pyridine, dioxane, tetrahydrofuran, N-methylpyrrolidone, acetonitrile) at a temperature of a range of room temperature to 100° C. to give the desired cyclic product.

[Scheme 6]

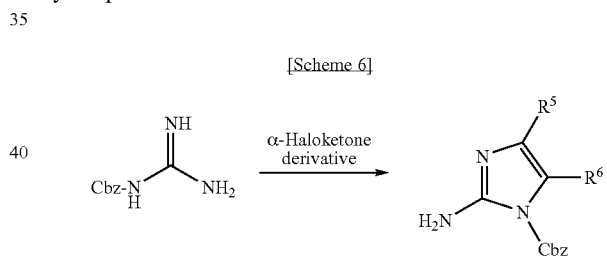

(wherein $R^5$ and $R^6$ have the same meanings as aforementioned)

The present compound wherein $R^1$ is formula (3):

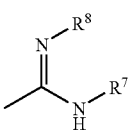

(3)

(wherein $R^7$ and $R^8$ have the same meanings as aforementioned) can be prepared by condensing a guanidine derivative (which can be prepared by a known synthetic method of a substituted guanidine, for example, as those shown in Scheme 7 (R. Samuel et al., J. Org. Chem., 73, 602, 1951)) according to scheme 1. For example, the substituted guanidine derivative can be prepared by treating thiourea derivative with methyl iodide in an alcoholic solvent such as methanol, ethanol, propanol, etc., at a temperature of a range of 50° C. to 100° C. to give methylthiourea derivative, and by treating the resulting methylthiourea derivative with aqueous ammonia in an alcoholic solvent such as methanol, ethanol, propanol, etc., at a temperature of a range of 50° C. to 100° C. according to scheme 7.

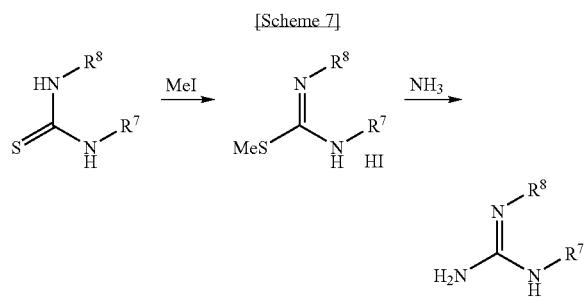

[Scheme 7]

(wherein $R^7$ and $R^8$ have the same meanings as aforementioned)

The compound represented by the general formula (1) can be formed in a pharmaceutically acceptable acid salt with inorganic acid or organic acid or a pharmaceutically acceptable base salt thereof, if necessary. Examples of the acid salt include salts with inorganic acid, such as hydrochloride, hydrobromide, sulfate, phosphate, etc., with organic carboxylic acid, such as formate, acetate, fumarate, maleate, oxalate, citrate, malate, tartarate, aspartate or glutamate, etc., and with sulfonic acid, such as methanesulfonate, benzenesulfonate, p-toluenesulfonate, hydroxybenzensulfonate, dihydroxybenzensulfonate, etc. Examples of a pharmaceutically acceptable base salt include ammonium salt, lithium salt, sodium salt, potassium salt, calcium salt or magnesium salt, etc.

In addition, the present invention includes a hydrate and a solvate such as ethanolate, etc., of the compound represented by the general formula (1) or a pharmaceutically acceptable salt thereof.

The compound of the present invention or a pharmaceutically acceptable salt thereof has asymmetry in some cases, or has a substituent having an asymmetric carbon in some cases, such that there is an optical isomer. The compound of the present invention includes a mixture of the respective isomer or an isolated isomer. Examples of a method for obtaining such optical isomer in a pure form include the optical resolution.

As the optical resolution, when the compound of the present invention or an intermediate thereof has a basic functional group, they may form a salt with an optically active acid (for example, monocarboxylic acids such as mandelic acid, N-benzyloxyalanine or lactic acid, etc., or dicarboxylic acids such as tartaric acid, o-diisopropylidenetartaric acid or malic acid, etc., or sulfonic acids such as camphorsulfonic acid or bromocamphorsulfonic acid, etc.) in an inert solvent (for example, alcoholic solvents such as methanol, ethanol or 2-propanol, ether solvents such as diethyl ether, ester solvents such as ethyl acetate, aromatic hydrocarbon solvents such as toluene, acetonitrile, or a mixed solvent thereof).

In addition, when the compound of the present invention or an intermediate thereof has an acidic substituent such as a carboxyl group, etc., it may be formed as a salt with an optically active amine (for example, organic amines such as α-phenethylamine, quinine, quinidine, cinchonidine, cinchonine or strychnine, etc.). Examples of the temperature used to form a salt include a temperature of a range of room temperature to the boiling point of the solvent. In order to improve optical purity, it is desirable to raise the temperature to near boiling point of the solvent only once. Chemical yield can be improved by cooling before filtering of the precipitated salt, if necessary. It is suitable that an amount of an optically active acid or amine to be used be in a range of about 0.5 to about 2.0 molar equivalents, preferably in a range of around 1 molar equivalent relative to that of the substrate. If necessary, a crystal may be recrystallized in an inert solvent (for example, alcoholic solvents such as methanol, ethanol or 2-propanol, ether solvents such as diethyl ether, ester solvents such as ethyl acetate, aromatic hydrocarbon solvents such as toluene, acetonitrile, or a mixed solvent thereof) to obtain an optically active salt having a high purity. If necessary, the resulting salt may be treated with an acid or a base by conventional methods to obtain a free compound.

The prepared compound of the present invention can be subjected to conventional separation and purification means after completion of the aforementioned series of reactions. For example, the compound of the present invention can be obtained in a purer form by extraction, distribution, re-precipitation, recrystallization, or column chromatography, etc. In addition, the molecular structure of the compound of the present invention can be determined by spectroscopic means such as nuclear magnetic resonance spectrometry or infrared spectroscopy and/or mass spectrometry on the basis of a structure derived from a corresponding starting material.

The therapeutic agent of the present invention can be administered orally or parenterally. When administered orally, the agent can be administered in a dosage form which is conventionally used. When administered parenterally, the agent can be administered in a dosage form such as an agent for topical application, an injection agent, a transdermal agent or a nasal agent, etc.

The above dosage form is formulated into a preparation with a pharmaceutically acceptable excipient or additive by conventional methods.

Examples of a pharmaceutically acceptable excipient or additive include a carrier, binder, flavor, buffer, thickener, colorant, stabilizer, emulsifier, dispersant, suspending agent, and antiseptic, etc.

Examples of a pharmaceutically acceptable excipient include magnesium carbonate, magnesium stearate, talc, sugar, lactose, pectin, dextrin, starch, gelatin, tragacanth, methylcellulose, sodium carboxymethylcellulose, low melting point wax, and cacao butter, etc. A capsule can be formulated by putting the present compound together with a pharmaceutically acceptable excipient therein. The therapeutic agent of the present invention can be put with a pharmaceutically acceptable excipient, or without the excipient into a capsule. A cachet can be prepared by similar methods.

Examples of a liquid preparation for injection include a solution, suspension, emulsion, etc., such as an aqueous solution, or water-propylene glycol solution, etc. The liquid preparation may also be prepared in the form of a solution of polyethylene glycol or/and propylene glycol, which may contain water. A liquid preparation suitable for oral administration can be prepared by adding water to the present compound and, if necessary, adding a colorant, flavor, stabilizer, sweetener, solubilizer, or thickener, etc. A liquid preparation suitable for oral administration may be prepared by adding the compound of the present invention or a pharmaceutically acceptable salt thereof together with a dispersant to water in order to increase viscosity. Examples of a thickener include a pharmaceutically acceptable natural or synthetic gum, resin, methylcellulose, sodium carboxymethylcellulose or known suspending agent, etc.

Examples of an agent for topical application include the aforementioned liquid preparation, a cream, aerosol, spray, powder, lotion, and ointment, etc. The aforementioned agent for topical application can be prepared by mixing the present compound or a pharmaceutically acceptable salt thereof with a pharmaceutically acceptable diluent and carrier that are conventionally used. An ointment or cream is obtained, for example, by formulating into a preparation by adding a thickener and/or a gelling agent to an aqueous or oily base. Examples of a base include water, liquid paraffin, and vegetable oil (peanut oil, castor oil, etc.), etc. Examples of a thickener include soft paraffin, aluminum stearate, cetostearyl alcohol, propylene glycol, polyethylene glycol, lanolin, hydrogenated lanolin, and beeswax, etc.

A lotion can be prepared by adding one or more kinds of pharmaceutically acceptable stabilizer, suspending agent, emulsifier, diffusing agent, thickener, colorant, and flavor, etc., to an aqueous or oily base.

A powder is formulated into a preparation with a base for a pharmaceutically acceptable powder. Examples of the base include talc, lactose, and starch, etc. Drops can be formulated into a preparation from an aqueous or non-aqueous base and one or more kinds of pharmaceutically acceptable diffusing agent, suspending agent, and solubilizer, etc. The agent for topical application may, if necessary, contain an antiseptic such as methyl hydroxybenzoate, propyl hydroxybenzoate, chlorocresol, and benzalkonium chloride, or a bacteriostat. A preparation of a liquid spray, a powder or a drop containing the present compound or a pharmaceutically salt thereof as an active ingredient can be administered nasally.

The dose and the frequency of administration may vary according to the conditions, ages, weights of the patients and the dosage form, etc., and when administered orally, the present compound can usually be administered in a dose of a range of about 1 to about 3000 mg, preferably a range of about 5 to about 300 mg per day in adult, once a day, or divided into several dosage units. When administered as an injection, the present compound can usually be administered in a dose of a range of about 0.1 to about 300 mg, preferably a range of about 1 to about 100 mg per day, once a day, or divided into several dosage units.

The present invention is illustrated in more detail below by Examples and Reference Examples, but the present invention should not be construed to be limited thereto.

In this specification, the following abbreviations can be used for sake of simplicity of description.

HOBt.H$_2$O: 1-Hydroxybenzotriazole monohydrate,
WSC.HCl: 1-Ethyl-3-(3'-dimethylaminopropyl)carbodiimide monohydrochloric acid salt,
HBTU: 2-(1H-Benzotriazolyl)-1,1,3,3-tetramethyluronium hexafluorophosphate

EXAMPLES

Reference Example 1

(2R,3S)-3-[(tert-Butoxycarbonyl)amino]-4-phenyl-2-(tetrahydro-2H-pyran-1-yloxy)butanoic acid

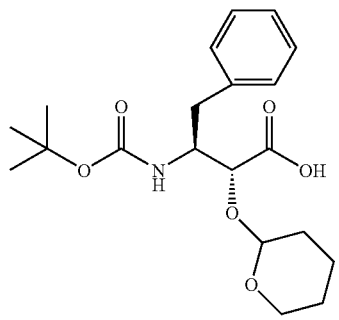

A mixture (40 mL) of (2R,3S)-3-[(tert-butoxycarbonyl)amino]-2-hydroxy-4-phenylbutanoic acid 8.86 g (30 mmol), p-toluenesulfonic acid pyridinium 1.51 g (6.0 mmol), dihydropyran (50 mL) and tetrahydrofuran was stirred at 80° C. for 8 hours. The solvent was concentrated, and thereto was 1N aqueous sodium hydroxide solution (100 mL) and the mixture was washed with hexane/ethyl acetate=1:1 (100 mL). The aqueous layer was adjusted by adding 1N hydrochloric acid to pH=4 and the mixture was extracted with ethyl acetate. After drying on magnesium sulfate, the solvent was evaporated to give 7.38 g (19.4 mmol) of the title compound (yield: 65%).

MS (LC/MS): 380 [M+H]$^+$
$^1$H-NMR (400 MHz, DMSO-d$_6$): δ 1.27 (s, 9H), 1.49 (br, 3H), 1.63 (br, 2H), 1.85 (br, 1H), 2.72-2.85 (m, 2H), 3.45-3.48 (m, 1H), 3.78-3.86 (m, 1H), 4.04-4.11 (m, 1H), 4.13-4.16 (m, 1H), 4.64 (br, 1H), 7.18 (d, 1H, J=7.32 Hz), 7.23-7.28 (m, 5H), 12.70 (br, 1H).

Reference Example 2 tert-Butyl (1S,2R)-1-benzyl-3-(1H-imidazol-2-ylamino)-3-oxo-2-(tetrahydro-2H-pyran-2-yloxy)propyl]carbamate

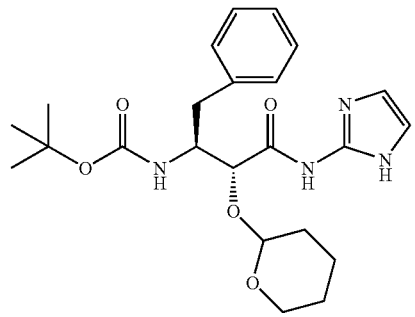

2-aminoimidazole sulfate 1.85 g (14.0 mmol) was dissolved in water 4 mL, and thereto was added 10 N aqueous sodium hydroxide solution 14 mL under ice-cooling and the mixture was neutralized. To this aqueous solution were added a 40 mL solution of (2R,3S)-3-[(tert-butoxycarbonyl) amino]-4-phenyl-2-(tetrahydro-2H-pyran-1-yloxy)butanoic acid 2.65 g (7.0 mmol) obtained in Reference Example 1, HOBt.H$_2$O 1.18 g (7.7 mmol) and WSC.HCl 4.69 g (24.5 mmol) in N,N-dimethylformamide and the mixture was stirred at 50° C. for 10 hours. After completion of the reaction, the mixture was concentrated and to the residue were added ethyl acetate and 5% aqueous sodium carbonate solution, and the mixture was extracted. The organic layer was washed with an aqueous saturated sodium chloride solution, and thereto were added magnesium sulfate and activated charcoal and the mixture was stirred at room temperature for 30 minutes. After filtration and concentration of the mixture, the mixture was purified by a column chromatography on silica gel (eluted with chloroform-methanol) and followed by a recrystallization from a mixed solvent of ethyl acetate and hexane. A precipitated material was collected by filtering and dried to give 1.86 g (4.19 mmol) of the title compound (yield: 60%).

MS (LC/MS): 445 [M+H]$^+$
$^1$H-NMR (400 MHz, DMSO-d$_6$): δ 1.23 (s, 9H), 1.50 (br, 3H), 1.68 (br, 2H), 1.86 (br, 1H), 2.81 (d, 2H, J=7.20 Hz), 3.49 (br, 1H), 3.85 (m, 1H) 4.09 (m, 1H), 4.31 (d, 1H, J=3.76 Hz), 4.61 (m, 1H), 6.65-6.75 (br, 2H), 7.18 (d, 1H, J=5.96 Hz), 7.23-7.28 (m, 5H), 11.12 (br, 1H), 11.55 (br, 1H).

Reference Example 3

(2R,3S)-3-Amino-2-hydroxy-N-1H-imidazol-2-yl-4-phenylbutanamide 2 hydrochloric acid salts

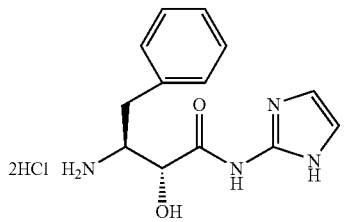

To a tert-butyl [(1S,2R)-1-benzyl-3-(1H-imidazol-2-ylamino)-3-oxo-2-(tetrahydro-2H-pyran-2-yloxy)propyl]carbamate 1.86 g (4.19 mmol) obtained in Reference Example 2 was added 4N hydrochloric acid/dioxane 42 mL and the mixture was stirred at room temperature for 3 hours. After completion of the reaction, the mixture was concentrated, washed with ether, filtered and dried to give 1.33 g (3.99 mmol) of the title compound (yield: 95%).

MS (LC/MS): 261 [M+H]$^+$ (free base)

$^1$H-NMR (400 MHz, DMSO-d$_6$): δ 2.94-3.09 (m, 2H), 3.44-3.66 (br, 2H), 3.71 (br, 1H), 4.23 (br, 1H), 7.25-7.43 (m, 7H), 7.73 (d, 1H, J=6.44 Hz), 12.02 (br, 1H), 13.19 (br, 1H).

Reference Example 4

Dimethyl 5-[(methylsulfonyl)amino]isophthalate

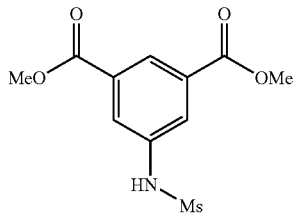

A mixture of dimethyl 3-aminoisophthalate 25.3 g (121 mmol), methanesulfonyl chloride 10 mL (130 mmol) and pyridine (50 mL) was stirred at 50° C. for 4 hours. The reaction solution was poured into a 0.5 N hydrochloric acid (300 mL), and the precipitated solid was collected by filtering, washed with 0.5 N hydrochloric acid and dried under vacuum to give 34.8 g (121 mmol) of the title compound (yield: 100%).

$^1$H-NMR (400 MHz, CDCl$_3$): δ 3.08 (s, 3H), 3.97 (s, 6H), 6.91 (s, 1H), 8.10 (s, 2H), 8.50 (s, 1H).

Reference Example 5

Dimethyl 5-[methyl(methylsulfonyl)amino]isophthalate

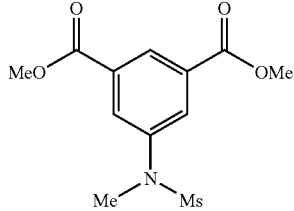

A mixture of dimethyl 5-[(methylsulfonyl)amino]isophthalate 34.8 g (121 mmol) obtained in Reference Example 4, methyl iodide 8.5 mL (137 mmol), potassium carbonate 41.8 g (302 mmol) and acetone (1000 mL) was stirred at room temperature for 8 hours. The mixture was filtered to remove the precipitates and the solvent was evaporated. To the residue was added water (500 mL) and the mixture was extracted twice with ethyl acetate (300 mL). After drying of the mixture on magnesium sulfate, the solvent was evaporated to give 36.0 g (119 mmol) of the title compound (yield: 99%).

$^1$H-NMR (400 MHz, CDCl$_3$): δ 2.89 (s, 3H), 3.39 (s, 3H), 3.97 (s, 6H), 8.23 (s, 2H), 8.61 (s, 1H).

Reference Example 6

3-(Methoxycarbonyl)-5-[methyl(methylsulfonyl)amino]benzoic acid

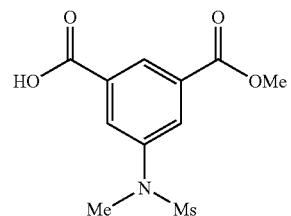

A mixture of dimethyl 5-[methyl(methylsulfonyl)amino]isophthalate obtained in Reference Example 5 36.0 g (119 mmol), potassium hydroxide 8.71 g (155 mmol), methanol (360 mL) and tetrahydrofuran (240 mL) was stirred at 90° C. for 1.5 hours. To a mixture of 1N hydrochloric acid (200 mL) and ice water (500 mL) was added the reaction mixture dropwise, and the precipitated solid was collected by filtering, and dried under vacuum to give 32.4 g (113 mmol) of the title compound (yield: 95%).

$^1$H-NMR (400 MHz, CDCl$_3$): δ 2.91 (s, 3H), 3.41 (s, 3H), 3.98 (s, 3H), 8.29 (s, 2H), 8.67 (s, 1H).

Reference Example 7

3-[Methyl(methylsulfonyl)amino]-5-({[(1R)-1-phenylethyl]amino}-carbonyl)benzoic acid

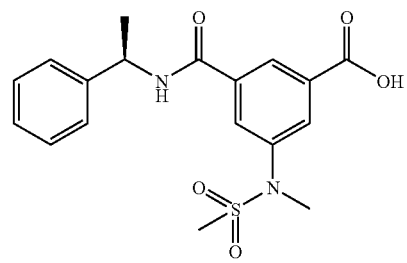

A mixture of 3-(methoxycarbonyl)-5-[methyl(methylsulfonyl)amino]isophthalic acid obtained in Reference Example 6 11.5 g (40 mmol), WSC.HCl 8.43 g (44 mmol), HOBt.H$_2$O 6.74 g (44 mmol), (R)-1-phenethylamine 5.6 mL (44 mmol) and N,N-dimethylformamide (100 mL) was stirred at room temperature for 15 hours. The reaction solution was diluted with ethyl acetate/toluene=1:1 (300 mL) and washed with water (400 mL). The aqueous layer was extracted twice with ethyl acetate/toluene=1:1 (300 mL). The combined organic layer was dried on magnesium sulfate and the mixture was concentrated. The resulting solid was dissolved in 2N aqueous sodium hydroxide solution (80 mL), methanol (80 mL) and tetrahydrofuran (80 mL) and the mixture was stirred at room temperature for 15 hours. The solvent was concentrated and thereto was added water (100 mL) and the mixture was washed twice with ethyl acetate (100 mL). The aqueous layer was adjusted by adding 1N hydrochloric acid to pH=3 and the precipitated solid was collected by filtering and dried under vacuum to give 13.2 g (35.1 mmol) of the title compound. (yield: 88%).

MS (LC/MS): 377 [M+H]+

$^1$H-NMR (400 MHz, DMSO-$d_6$): δ 1.49 (3H, d, J=7.2 Hz), 2.99 (3H, s), 3.30 (3H, s), 5.14-5.23 (1H, m), 7.20-7.25 (1H, m), 7.30-7.35 (2H, m), 7.38-7.41 (2H, m), 8.05-8.08 (2H, m), 8.40 (1H, t, J=1.4 Hz), 9.12 (1H, d, J=8.0 Hz).

Example 1

N-[(1S,2R)-1-Benzyl-2-hydroxy-3-(1H-imidazol-2-ylamino)-3-oxopropyl]-5-[methyl(methylsulfonyl)amino]-N'-[(1R)-1-phenylethyl]isophthalamide

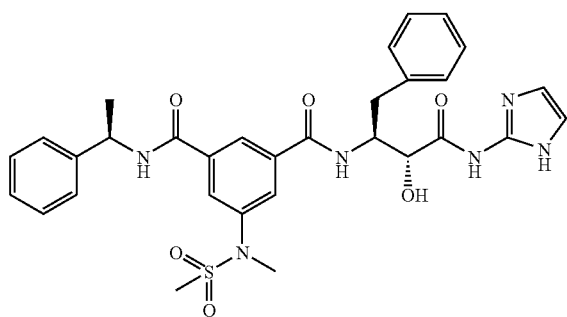

(2R,3S)-3-Amino-2-hydroxy-N-1H-imidazol-2-yl-4-phenylbutanamide 2 hydrochloric acid salts 67 mg (80.2 mmol) obtained in Reference Example 3 was dissolved in N,N-dimethylformamide 1 mL and the mixture was neutralized by adding triethylamine 0.06 mL under ice-cooling. Thereto were added 3-[methyl(methylsulfonyl)amino]-5-({[(1R)-1-phenylethyl]amino}carbonyl)-benzoic acid obtained in Reference Example 7 75 mg (0.2 mmol), HOBt.H$_2$O 32 mg (0.21 mmol) and WSC.HCl 42 mg (0.22 mmol) and the mixture was stirred at room temperature overnight. After completion of the reaction, the reaction solution was extracted by adding ethyl acetate and 5% aqueous sodium carbonate solution. The organic layer was washed with an aqueous saturated sodium chloride solution and dried on magnesium sulfate. After filtration and concentration of the mixture, the reaction residue was purified on HPLC to give 36 mg (0.06 mmol) of the title compound (yield: 29%).

MS (LC/MS): 619 [M+H]+

$^1$H-NMR (400 MHz, DMSO-$d_6$): δ 1.56 (d, 3H, J=7.04 Hz), 2.95-3.04 (m, 5H), 3.33 (s, 3H), 4.30 (m, 1H), 4.69 (m, 1H), 5.24 (m, 1H), 6.06 (br, 1H), 6.75 (br, 2H), 7.21-7.49 (m, 10H), 7.90 (s, 1H), 8.02 (s, 1H), 8.22 (s, 1H), 8.40 (d, 1H, J=9.12 Hz), 9.07 (d, 1H, J=7.92 Hz), 10.85 (br, 1H), 11.58 (br, 1H)

Reference Example 8

Methyl 3-[(methylsulfonyl)amino]-5-nitrobenzoic acid

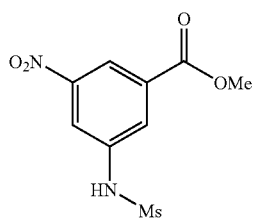

To a solution of 3-amino-5-nitrobenzoic acid 10.3 g (56.6 mmol) in methanol (100 mL) was added thionyl chloride 6.5 mL (89 mmol) dropwise under ice-cooling, and the mixture was stirred at 70° C. for 4 hours. The solvent was evaporated and thereto was added water and the mixture was extracted three times with ethyl acetate (100 mL). The organic layer was washed with an aqueous saturated sodium bicarbonate solution and dried on magnesium sulfate, filtered and concentrated to give 11.0 g (56.1 mmol) of methyl 3-amino-5-nitrobenzoate as a brown solid (yield: 99%).

A mixture of methyl 3-amino-5-nitrobenzoate 24.7 g (126 mmol), pyridine 51 mL (630 mmol), methanesulfonyl chloride 12 mL (151 mmol) and chloroform (250 mL) was stirred at 40° C. for 5 hours. The solvent was evaporated and to the residue was added 1N hydrochloric acid and the mixture was extracted with ethyl acetate 500 mL. The organic layer was washed with 1N hydrochloric acid and 5% aqueous sodium chloride solution and dried on magnesium sulfate. The solvent was evaporated and the residue was recrystallized from a mixed solvent of ethyl acetate and n-hexane to give 32.1 g (117 mmol) of the title compound (yield: 93%).

$^1$H-NMR (400 MHz, CDCl$_3$): δ 3.15 (s, 3H), 4.00 (s, 3H), 8.15 (s, 1H), 8.30 (s, 1H), 8.64 (s, 1H).

Reference Example 9

Methyl 3-[methyl(methylsulfonyl)amino]-5-nitrobenzoate

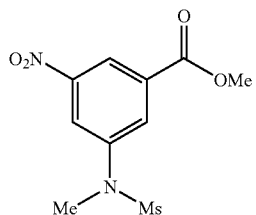

A mixture of methyl 3-[(methylsulfonyl)amino]-5-nitrobenzoate obtained in Reference Example 8 8.22 g (30 mmol), methyl iodide 2.0 mL (32 mmol), potassium carbonate 10.4 g (75 mmol) and acetone (250 mL) was stirred at room temperature for 16 hours. The mixture was filtered to remove the precipitates and the solvent was evaporated. To the residue was added water (150 mL) and the mixture was extracted twice with ethyl acetate (100 mL). After drying of the mixture on magnesium sulfate, the solvent was evaporated to give 8.55 g (29.7 mmol) of the title compound (yield: 99%).

$^1$H-NMR (400 MHz, CDCl$_3$): δ 2.94 (s, 3H), 3.44 (s, 3H), 4.01 (s, 3H), 8.36 (s, 1H), 8.45 (s, 1H), 8.77 (s, 1H).

Reference Example 10

Methyl 3-amino-5-[methyl(methylsulfonyl)amino]benzoate

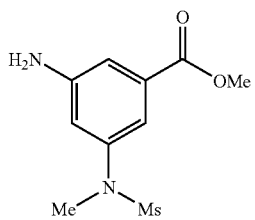

A mixture of methyl 3-[methyl(methylsulfonyl)amino]-5-nitrobenzoate obtained in Reference Example 9 5.76 g (20 mmol), 10% Pd/C (50% wet) (1.50 g), methanol (80 mL) and ethyl acetate (80 mL) was stirred at room temperature under hydrogen atmosphere for 1.5 hours. The reaction solution was filtered on Celite and the solvent was evaporated to give 5.11 g (19.8 mmol) of the title compound (yield: 99%).

$^1$H-NMR (400 MHz, CDCl$_3$): δ 2.85 (s, 3H), 3.31 (s, 3H), 3.90 (s, 3H), 6.97 (t, 1H, J=2.2 Hz), 7.28 (s, 1H), 7.33 (s, 1H).

Reference Example 11

5-Propylamino-3-[methyl(methylsulfonyl)amino]benzoic acid

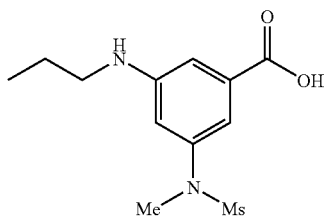

To a mixture of methyl 3-[methyl(methylsulfonyl)amino]-5-nitrobenzoate obtained in Reference Example 9 2.88 g (10 mmol), 10% Pd/C (50% wet) (0.60 g), methanol (30 mL), propionitrile (10 mL) and H$_2$O (10 mL) was added ammonium formate 12.6 g (200 mmol) and the mixture was stirred at 50° C. for 5 hours. The reaction solution was filtered on Celite and the solvent was evaporated and the mixture was dissolved in ethyl acetate, washed with water and dried on magnesium sulfate. The solvent was evaporated and the residue was purified by a column chromatography on silica gel (eluted with chloroform). The resulting methyl ester 1.90 g (6.33 mmol) was dissolved in methanol (20 mL) and thereto was added 2.5N aqueous sodium hydroxide solution 7.60 mL (18.99 mmol) and the mixture was stirred at 40° C. for 1 hour. To the reaction solution was added 5% aqueous citrate and the mixture was extracted with ethyl acetate and washed with 5% aqueous sodium chloride solution and dried on magnesium sulfate. The solvent was evaporated and the residue was recrystallized from n-hexane to give 1.28 g (4.3 mmol) of the title compound (yield: 43%).

$^1$H-NMR (400 MHz, DMSO-d$_6$): δ 0.94 (t, 3H, J=7.4 Hz), 1.51-1.60 (m, 2H), 2.93 (s, 3H), 2.95-3.00 (m, 2H), 3.20 (s, 3H), 6.09 (t, 1H, J=4.6 Hz), 6.76 (s, 1H), 7.08 (s, 2H), 12.85 (s, 1H).

Example 2

N-[1-Benzyl-2-hydroxy-3-(1H-imidazoyl-2-ylamino)-3-oxopropyl]-3-[methyl(methylsulfonyl)amino]-5-(propylamino)benzamide

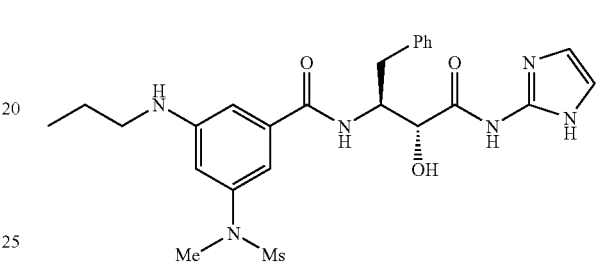

The title compound was prepared using (2R,3S)-3-amino-2-hydroxy-N-1H-imidazol-2-yl-4-phenylbutanamide 2 hydrochloric acid salts obtained in Reference Example 3 and 5-propylamino-3-[methyl(methylsulfonyl)amino]benzoic acid obtained in Reference Example 11 according to the method of Example 1.

$^1$H-NMR (400 MHz, DMSO-d$_6$): δ 0.92 (t, 3H, J=7.4 Hz), 1.48-1.58 (m, 2H), 2.91-3.08 (m, 7H), 3.15 (s, 3H), 4.09-4.16 (m, 1H), 4.33 (s, 1H), 4.55-4.63 (m, 1H), 6.65 (s, 1H), 6.72 (s, 1H), 6.79 (s, 1H), 7.16-7.23 (m, 3H), 7.25-7.30 (m, 2H), 7.30-7.35 (m, 2H), 8.00 (d, 1H, J=8.8 Hz), 11.92 (s, 1H).

Reference Example 12

Methyl 3-hydroxy-5-[methyl(methylsulfonyl)amino]benzoate

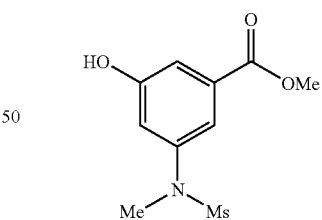

To a mixture of methyl 3-amino-5-[methyl(methylsulfonyl)amino]benzoate 1.29 g (5.0 mmol) in 2N hydrochloric acid (10 mL) and methanol (15 mL) was added sodium nitrite 0.759 g (11 mmol) under ice-cooling. Thereto was further added water (20 mL) and the mixture was stirred at 70° C. for 2 hours. The mixture was extracted twice with ethyl acetate (30 mL) and dried on magnesium sulfate and the solvent was evaporated to give 1.33 g (5.0 mmol) of the title compound (yield: 100%).

$^1$H-NMR (400 MHz, CDCl$_3$): δ 2.87 (s, 3H), 3.40 (s, 3H), 3.93 (s, 3H), 5.69 (s, 1H), 7.50 (t, 1H, J=2.0 Hz), 7.46 (s, 1H), 7.55 (s, 1H).

Reference Example 13

3-[(2-Methylcyclopropyl)methoxy]-5-[methyl(methylsulfonyl)amino]-benzoic acid

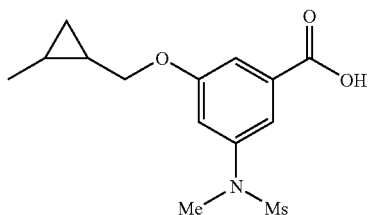

To a mixture of methyl 3-hydroxy-5-[methyl(methylsulfonyl)amino]benzoate 259 mg (1.0 mmol) obtained in Reference Example 12, 2-methylcyclopropanemethanol 0.10 mL (1.0 mmol), triphenylphosphine 367 mg (1.4 mmol) and tetrahydrofuran (6 mL) was added dibenzyl azodicarboxylate 0.32 mL (1.5 mmol) dropwise under ice-cooling and after 30 minutes, the mixture was heated to room temperature and stirred for 16 hours. The solvent was evaporated and the residue was purified by a column chromatography on silica gel (eluted with hexane/ethyl acetate=5:1→7:3). The resulting solid was dissolved in a mixture of 2N aqueous sodium hydroxide solution (2 mL), methanol (2 mL) and tetrahydrofuran (2 mL) and the mixture was stirred at room temperature for 15 hours. The solvent was concentrated and thereto was added water and the resulting mixture was washed with a mixed solvent of hexane/ethyl acetate=1:1. The aqueous layer was adjusted by adding 1N hydrochloric acid to pH=3 and the mixture was extracted with ethyl acetate. After drying of the mixture on magnesium sulfate, the solvent was evaporated to give 291 mg (0.93 mmol) of the title compound (yield: 93%).

$^1$H-NMR (400 MHz, CDCl$_3$): δ 0.35-0.42 (m, 1H), 0.45-0.52 (m, 1H), 0.70-0.78 (m, 1H), 0.88-0.97 (m, 1H), 7.50 (d, 3H, J=5.9 Hz), 2.87 (s, 3H), 3.35 (s, 3H), 3.70-3.83 (m, 2H), 7.23 (s, 1H), 7.58 (s, 1H), 7.63 (s, 1H).

Example 3

N-[1-Benzyl-2-hydroxy-3-(1H-imidazoyl-2-ylamino)-3-oxopropyl]-3-[(2-methylcyclopropyl)methoxy]-5-[methyl(methylsulfonyl)amino]benzamide

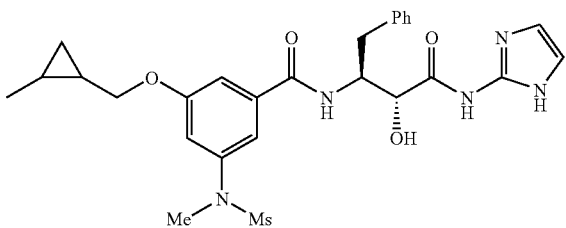

The title compound was prepared using (2R,3S)-3-amino-2-hydroxy-N-1H-imidazol-2-yl-4-phenylbutanamide 2 hydrochloric acid salts obtained in Reference Example 3 and 3-[(2-methylcyclopropyl)methoxy]-5-[methyl(methylsulfonyl)amino]benzoic acid obtained in Reference Example 13 according to the method of Example 1.

$^1$H-NMR (400 MHz, CDCl$_3$): δ 0.35-0.42 (m, 1H), 0.45-0.52 (m, 1H), 0.70-0.78 (m, 1H), 0.88-0.97 (m, 1H), 1.09 (d, 3H, J=5.9 Hz), 2.81 (s, 3H), 3.11 (d, 2H, J=7.8 Hz), 3.25 (s, 3H), 3.70-3.82 (m, 2H), 4.44 (s, 1H), 4.88-4.97 (m, 1H), 6.89-6.93 (m, 1H), 6.99 (d, 2H, J=7.0 Hz), 7.17 (s, 1H), 7.25-7.35 (m, 5H).

Reference Example 14

3-[Methyl(methylsulfonyl)amino]-5-(2-phenylpropoxy)benzoic acid

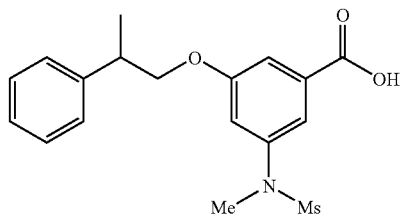

A mixture of methyl 3-hydroxy-5-[methyl(methylsulfonyl)amino]benzoate 259 mg (1.0 mmol) obtained in Reference Example 12, 2-phenyl-1-propanol 0.21 mL (1.5 mmol), tri-n-butylcyanomethylenephosphorane 482 mg (2.0 mmol) and toluene (5 mL) was stirred at 100° C. under argon atmosphere for 7 hours. The solvent was evaporated and the residue was purified by a column chromatography on silica gel (eluted with hexane/ethyl acetate=5:1→3:2). The resulting solid was dissolved in a mixture of 2N aqueous sodium hydroxide solution (2 mL), methanol (2 mL) and tetrahydrofuran (2 mL) and stirred at room temperature for 15 hours. The solvent was concentrated and thereto was added water and the mixture was washed with a mixed solvent of hexane/ethyl acetate=1:1. The aqueous layer was adjusted by adding 1N hydrochloric acid to pH=3 and the mixture was extracted with ethyl acetate. After drying of the mixture on magnesium sulfate, the solvent was evaporated to give 137 mg (0.38 mmol) of the title compound (yield: 38%).

$^1$H-NMR (400 MHz, CDCl$_3$): δ 1.43 (d, 3H, J=7.0 Hz), 2.86 (s, 3H), 2.86 (s, 3H), 3.24-3.30 (s, 1H), 3.37 (s, 3H), 4.00-4.16 (m, 2H), 7.21 (t, 1H, J=2.2 Hz), 7.27-7.38 (m, 5H), 7.50-7.53 (m, 1H), 7.61 (t, 1H, J=1.6 Hz).

Example 4

N-[1-Benzyl-2-hydroxy-3-(1H-imidazoyl-2-ylamino)-3-oxopropyl]-3-[methyl(methylsulfonyl)amino]-5-(2-phenylpropoxy)benzamide

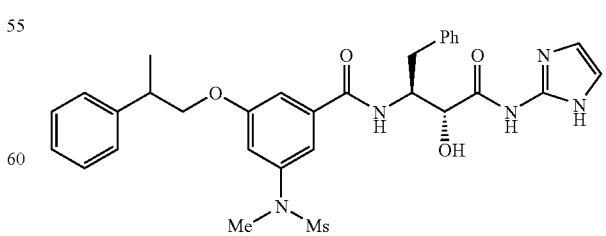

The title compound was prepared using (2R,3S)-3-amino-2-hydroxy-N-1H-imidazol-2-yl-4-phenylbutanamide 2 hydrochloric acid salts obtained in Reference Example 3 and 3-[methyl(methylsulfonyl)amino]-5-(2-phenylpropoxy)benzoic acid obtained in Reference Example 14 according to the method of Example 1.

$^1$H-NMR (400 MHz, DMSO-$d_6$): δ 1.34 (d, 3H, J=7.0 Hz), 2.90-3.07 (m, 5H), 3.16-3.24 (m, 4H), 4.00-4.06 (m, 1H), 4.09-4.16 (m, 1H), 4.32 (s, 1H), 4.57-4.63 (m, 1H), 6.62 (s. 1H), 7.07 (s, 1H), 7.14-7.21 (m, 4H), 7.21-7.28 (m, 4H), 7.28-7.36 (m, 6H), 8.24 (d, 1H, J=8.8 Hz), 11.97 (s, 1H).

Reference Example 15

Methyl 3-bromo-5-[methyl(methylsulfonyl)amino]benzoate

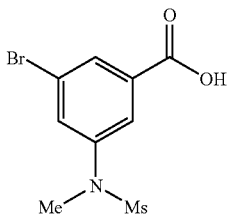

To a solution of methyl 3-amino-5-[methyl(methylsulfonyl)amino]benzoate 1.81 g (7.0 mmol) obtained in Reference Example 10 in 48% aqueous bromic acid solution (20 mL) was added sodium nitrite 0.621 g (9.0 mmol) under ice-cooling and the mixture was heated to 70° C. Thereto was added a solution of cuprous (I) bromide 0.717 g (5.0 mmol) in 48% aqueous bromic acid solution (3.5 mL) dropwise and the mixture was stirred at 70° C. for 2 hours. The mixture was cooled to room temperature and thereto was added water (100 mL) and the mixture was extracted twice with ethyl acetate (100 mL). After drying of the mixture on magnesium sulfate, the mixture was concentrated. The resulting solid was dissolved in methanol (20 mL) and thereto was added thionyl chloride 0.80 mL dropwise under ice-cooling and the mixture was stirred at 70° C. for 5 hours. The solvent was evaporated and thereto was added water and the mixture was extracted three times with ethyl acetate (20 mL). The organic layer was washed with saturated aqueous sodium bicarbonate solution and dried on magnesium sulfate, and the solvent was evaporated and the residual solid was purified by a column chromatography on silica gel (eluted with hexane/ethyl acetate=5:1→5:2) to give 1.19 g (3.69 mmol) of the title compound (yield: 53%).

$^1$H-NMR (400 MHz, CDCl$_3$): δ 2.88 (s, 3H), 3.35 (s, 3H), 3.94 (s, 3H), 7.78 (t, 1H, J=2.0 Hz), 7.94 (t, 1H, J=2.0 Hz), 8.10 (t, 1H, J=2.0 Hz).

Reference Example 16

3-(2-Furyl)-5-[methyl(methylsulfonyl)amino]benzoic acid

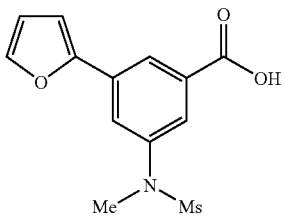

A mixture of methyl 3-bromo-5-[methyl(methylsulfonyl)amino]benzoate obtained in Reference Example 15 166 mg (0.5.0 mmol), tri-n-butyl(2-furyl)stannane 0.18 mL (0.55 mmol), lithium chloride 42 mg (0.10 mmol), tetrakistriphenylphosphine palladium(0) 29 mg (0.025 mmol) and N,N-dimethylformamide (1.5 mL) was stirred at 100° C. under argon atmosphere for 7 hours. The mixture was diluted with a mixed solvent of ethyl acetate/toluene=1:1 and washed twice with water. After drying of the mixture on magnesium sulfate, the mixture was concentrated and the residual oil was purified by a column chromatography on silica gel (eluted with hexane/ethyl acetate=2:1→1:1). The resulting solid was dissolved in a mixture of 2N aqueous sodium hydroxide solution (2 mL), methanol (2 mL) and tetrahydrofuran (2 mL) and the mixture was stirred at room temperature for 15 hours. The solvent was concentrated and thereto added water and the mixture was washed with a mixed solvent of hexane/ethyl acetate=1:1. The aqueous layer was adjusted by adding 1N hydrochloric acid to pH=3 and the mixture was extracted with ethyl acetate. After drying of the mixture on magnesium sulfate, the solvent was evaporated to give 105 mg (0.355 mmol) of the title compound (yield: 71%).

$^1$H-NMR (400 MHz, CDCl$_3$): δ 2.92 (s, 3H), 3.41 (s, 3H), 6.51-6.54 (m, 1H), 6.82 (d, 1H, J=3.2 Hz), 7.52 (d, 1H, J=1.6 Hz), 7.91-7.94 (m, 1H), 7.97 (d, 1H, J=1.8 Hz), 8.30 (d, 1H, J=1.5 Hz).

Example 5

N-[1-Benzyl-2-hydroxy-3-(1H-imidazoyl-2-ylamino)-3-oxopropyl]-3-(2-furyl)-5-[methyl(methylsulfonyl)amino]benzamide

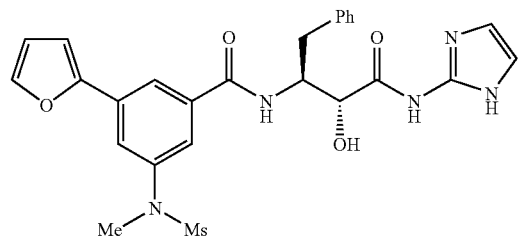

The title compound was prepared using (2R,3S)-3-amino-2-hydroxy-N-1H-imidazol-2-yl-4-phenylbutanamide 2 hydrochloric acid salts obtained in Reference Example 3 and 3-(2-furyl)-5-[methyl(methylsulfonyl)amino]benzoic acid obtained in Reference Example 16 according to the method of Example 1.

$^1$H-NMR (400 MHz, DMSO-$d_6$): δ 2.95-3.11 (m, 5H), 3.26 (s, 3H), 4.35 (s, 1H), 4.59-4.66 (m, 1H), 6.60-6.67 (m, 2H), 7.06 (d, 1H, J=3.3 Hz), 7.16-7.22 (m, 3H), 7.26-7.31 (m, 2H), 7.33-7.38 (m, 2H), 7.55 (t, 1H, J=1.7 Hz), 7.79-7.83 (m, 1H), 7.92 (s, 1H), 8.39 (d, 1H, J=8.8 Hz), 11.89 (s, 1H).

Reference Example 17

3'-Methyl-5-[methyl(methylsulfonyl)amino]biphenyl-3-carboxylic acid

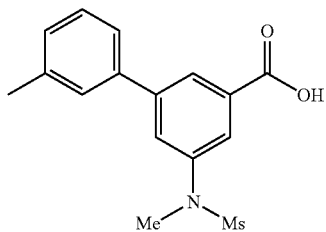

A mixture of methyl 3-bromo-5-[methyl(methylsulfonyl)amino]benzoate obtained in Reference Example 15 38 mg (0.12 mmol), 3-methyl-phenylboronic acid 33 mg (0.24 mmol), cesium carbonate 3.7 mg (0.012 mmol), palladium (II) acetate 1.4 mg (0.0060 mmol), triethylamine 0.056 mL (0.40 mmol) and N,N-dimethylformamide (0.5 mL) was stirred at 100° C. under argon atmosphere for 7 hours. The mixture was diluted with a mixed solvent of ethyl acetate/toluene=1:1 and wished successively with 10% aqueous ammonia and 1N hydrochloric acid. After drying of the mixture on magnesium sulfate, the mixture was concentrated and the residue was purified by a column chromatography on silica gel (eluted with hexane/ethyl acetate=5:13:1). The resulting solid was dissolved in a mixture of 2N aqueous sodium hydroxide solution (0.5 mL), methanol (0.5 mL) and tetrahydrofuran (0.5 mL) and the mixture was stirred at room temperature for 15 hours. The solvent was concentrated and the residue was adjusted by adding 1N hydrochloric acid to pH=3, and the mixture was extracted with ethyl acetate. After drying of the mixture on magnesium sulfate, the solvent was evaporated to give 28 mg (0.355 mmol) of the title compound (yield: 75%).

$^1$H-NMR (400 MHz, CDCl$_3$): δ 2.44 (s, 3H), 2.92 (s, 3H), 3.43 (s, 3H), 7.21-7.25 (m, 1H), 7.33-7.40 (m, 1H), 7.40-7.46 (m, 2H), 7.90 (s, 1H), 8.01 (s, 1H), 8.26 (s, 1H).

Example 6

N-[1-Benzyl-2-hydroxy-3-(1H-imidazoyl-2-ylamino)-3-oxopropyl]-3'-methyl-5-[methyl(methylsulfonyl)amino]biphenyl-3-carboxamide

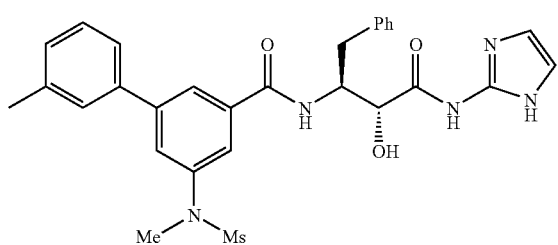

The title compound was prepared using (2R,3S)-3-amino-2-hydroxy-N-1H-imidazol-2-yl-4-phenylbutanamide 2 hydrochloric acid salts obtained in Reference Example 3 and 3'-methyl-5-[methyl(methylsulfonyl)amino]biphenyl-3-carboxylic acid obtained in Reference Example 17 according to the method of Example 1.

$^1$H-NMR (400 MHz, DMSO-d$_6$): δ 2.90-3.05 (m, 5H), 3.28 (s, 3H), 4.23 (s, 1H), 4.59-4.67 (m, 1H), 5.99 (s, 1H), 6.70 (s, 2H), 7.14-7.20 (s, 1H), 7.22-7.34 (m, 5H), 7.39 (t, 1H, J=7.6 Hz), 7.47-7.52 (m, 2H), 7.64 (s, 1H), 7.74 (s, 1H), 7.89 (s, 1H), 8.33 (d, 1H, J=8.7 Hz), 10.73 (s, 1H), 11.52 (s, 1H).

Reference Example 18

Methyl 3-[methyl(methylsulfonyl)amino]-5-(2-oxo-4-phenylpyrrolidin-1-yl)benzoate

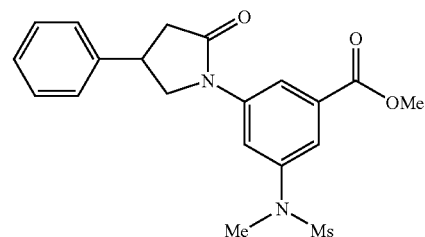

A mixture of methyl 3-bromo-5-[methyl(methylsulfonyl)amino]benzoate obtained in Reference Example 15 322 mg (1.0 mmol), 4-phenyl-2-pyrrolidinone 177 mg (1.1 mmol), cesium carbonate 456 mg (1.4 mmol), tris(dibenzylideneacetone)dipalladium(0) 4.6 mg (0.005 mmol), Zandphos 8.7 mg (0.015 mmol) and 1,4-dioxane (2 mL) was stirred at 110° C. under argon atmosphere for 7 hours. The reaction solution was diluted with ethyl acetate and the resulting precipitates were filtered. The solvent was evaporated and the residual solid was purified by a column chromatography on silica gel (eluted with hexane/ethyl acetate=3:1→1:1) to give 329 mg (0.817 mmol) of the title compound (yield: 82%).

$^1$H-NMR (400 MHz, CDCl$_3$): δ 2.85 (dd, 1H, J=17.2, 9.1 Hz), 2.90 (s, 3H), 3.05 (dd, 1H, J=17.1, 8.8 Hz), 3.37 (s, 3H), 3.70-3.78 (m, 1H), 3.93 (s, 3H), 3.94-3.98 (m, 1H), 4.26 (dd, 1H, J=9.5, 8.2 Hz), 7.28-7.34 (m, 2H), 7.36-7.42 (m, 3H), 7.82 (s, 1H), 8.01 (s, 1H), 8.19 (s, 1H).

Reference Example 19

3-[Methyl(methylsulfonyl)amino]-5-(2-oxo-4-phenylpyrrolidin-1-yl)benzoic acid

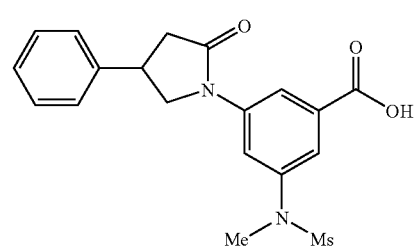

A mixture of methyl 3-[methyl(methylsulfonyl)amino]-5-(2-oxo-4-phenylpyrrolidin-1-yl)benzoate obtained in Reference Example 18 329 mg (0.32 mmol), 2N aqueous sodium hydroxide solution (0.5 mL), methanol (0.5 mL) and tetrahydrofuran (0.5 mL) was stirred at room temperature for 15 hours. The solvent was concentrated and the mixture was adjusted by adding 1N hydrochloric acid to pH=3 and the mixture was extracted with ethyl acetate. After drying of the mixture on magnesium sulfate, the solvent was evaporated to give 113 mg (0.291 mmol) of the title compound (yield: 91%).

$^1$H-NMR (400 MHz, CDCl$_3$): δ 2.85 (dd, 1H, J=17.2, 9.1 Hz), 2.92 (s, 3H), 3.06 (dd, 1H, J=17.1, 8.8 Hz), 3.38 (s, 3H), 3.70-3.78 (m, 1H), 3.94-3.98 (m, 1H), 4.27 (dd, 1H, J=9.5, 8.2 Hz), 7.28-7.34 (m, 2H), 7.36-7.42 (m, 3H), 7.86 (s, 1H), 8.12 (s, 1H), 8.24 (s, 1H).

Example 7

N-[1-Benzyl-2-hydroxy-3-(1H-imidazoyl-2-ylamino)-3-oxopropyl]-3-[methyl(methylsulfonyl)amino]-5-(2-oxo-4-phenylpyrrolidin-1-yl)benzamide

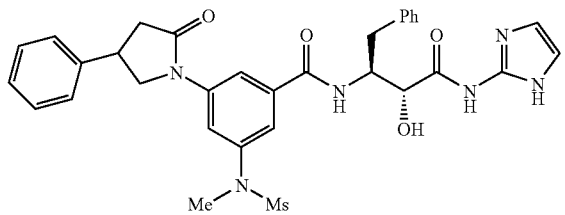

The title compound was prepared using (2R,3S)-3-amino-2-hydroxy-N-1H-imidazol-2-yl-4-phenylbutanamide 2 hydrochloric acid salts obtained in Reference Example 3 and 3-[methyl(methylsulfonyl)amino]-5-(2-oxo-4-phenylpyrrolidin-1-yl)benzoic acid obtained in Reference Example 19 according to the method of Example 1.

$^1$H-NMR (400 MHz, DMSO-d$_6$): δ 2.75-2.82 (m, 1H), 2.88-3.08 (m, 6H), 3.22 (s, 3H), 3.69-3.78 (m, 1H), 3.82-3.89 (m, 1H), 4.17-4.23 (m, 1H), 4.34 (s, 1H), 4.57-4.63 (m, 1H), 6.62 (s, 1H), 7.07 (s, 1H), 7.14-7.21 (m, 3H), 7.21-7.35 (m, 5H), 7.35-7.47 (m, 5H), 7.79 (d, 1H, J=6.5 Hz), 7.90-7.94 (m, 1H), 8.24-8.30 (m, 1H), 11.92 (s, 1H).

Reference Example 20

3-[Methyl(methylsulfonyl)amino]-5-(3-phenylpyrrolidin-1-yl)benzoic acid

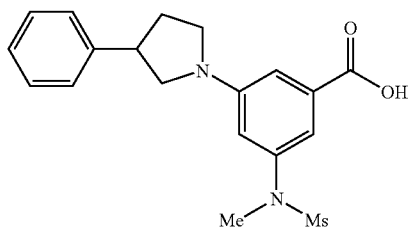

To a solution of methyl 3-[methyl(methylsulfonyl)amino]-5-(2-oxo-4-phenylpyrrolidin-1-yl)benzoate obtained in Reference Example 18 0.20 g (0.50 mmol) in tetrahydrofuran (3 mL) was added 1.0 M BH$_3$.tetrahydrofuran/tetrahydrofuran solution (1.5 mL) dropwise under ice-cooling and the mixture was stirred at room temperature for 16 hours. To the reaction solution was added methanol (3 mL) under ice-cooling, and the solvent was evaporated. The residue was dissolved in methanol (10 mL), and the mixture was stirred at 80° C. for 7 hours and the solvent was evaporated. The resulting solid was dissolved in a mixture of 2N aqueous sodium hydroxide solution (0.5 mL), methanol (0.5 mL) and tetrahydrofuran (0.5 mL) and the mixture was stirred at room temperature for 15 hours. The solvent was concentrated and the residue was adjusted by adding 1N hydrochloric acid to pH=3 and the mixture was extracted with ethyl acetate. After drying of the mixture on magnesium sulfate, the solvent was evaporated to give 165 mg (0.176 mmol) of the title compound (yield: 88%).

$^1$H-NMR (400 MHz, CDCl$_3$): δ 2.12-2.24 (m, 1H), 2.42-2.50 (m, 1H), 2.88 (s, 3H), 3.35 (s, 3H), 3.40 (t, 1H, J=8.8 Hz), 3.46-3.62 (m, 3H), 3.75-3.81 (m, 1H), 6.87 (t, 1H, J=2.2 Hz), 7.22 (s, 1H), 7.25-7.30 (m, 4H), 7.32-7.37 (s, 2H).

Example 8

N-[1-Benzyl-2-hydroxy-3-(1H-imidazoyl-2-ylamino)-3-oxopropyl]-3-[methyl(methylsulfonyl)amino]-5-(3-phenylpyrrolidin-1-yl)benzamide

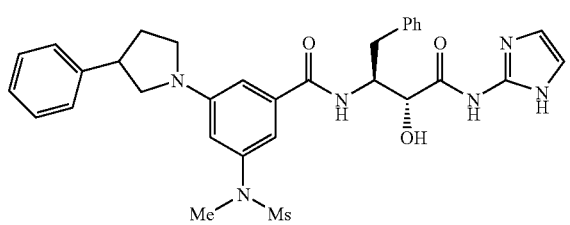

The title compound was prepared using (2R,3S)-3-amino-2-hydroxy-N-1H-imidazol-2-yl-4-phenylbutanamide 2 hydrochloric acid salts obtained in Reference Example 3 and 3-[methyl(methylsulfonyl)amino]-5-(3-phenylpyrrolidin-1-yl)benzoic acid obtained in Reference Example 20 according to the method of Example 1.

$^1$H-NMR (400 MHz, CDCl$_3$): δ 2.05-2.15 (m, 1H), 2.35-2.41 (m, 1H), 2.90-3.00 (m, 5H), 3.18 (s, 3H), 3.20-3.58 (m, 4H), 3.67-3.74 (m, 1H), 4.20 (s, 1H), 4.52-4.58 (m, 1H), 6.01 (s, 1H), 6.62 (s, 1H), 6.77 (s, 1H), 6.90 (s, 1H), 7.14-7.20 (m, 1H), 7.20-7.38 (m, 10H), 8.03 (d, 1H, J=8.8 Hz), 10.61 (s, 1H), 11.50 (s, 1H)

Reference Example 21

Methyl 3-(hydroxymethyl)-5-[methyl(methylsulfonyl)amino]benzoate

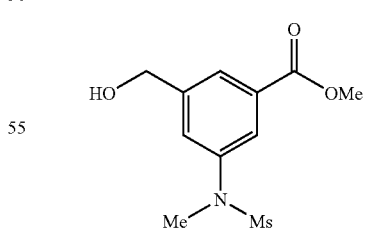

To a solution of 3-(methoxycarbonyl)-5-[methyl(methylsulfonyl)amino]benzoic acid obtained in Reference Example 62.07 g (7.2 mmol) in tetrahydrofuran (10 mL) was added 1.0 M BH$_3$.tetrahydrofuran/tetrahydrofuran solution 9 mL dropwise under ice-cooling and the mixture was stirred at room temperature for 16 hours. To the reaction solution was added methanol (3 mL) under ice-cooling, and the solvent was evaporated. To the residue was added water and the mixture was extracted with ethyl acetate. After drying of the mixture on magnesium sulfate, the solvent was evaporated and the resulting solid was recrystallized from chloroform/hexane to give 1.64 g (6.0 mmol) of the title compound (yield: 83%).

$^1$H-NMR (400 MHz, CDCl$_3$): δ 2.88 (s, 3H), 3.36 (s, 3H), 3.94 (s, 3H), 4.78 (d, 2H, J=5.5 Hz), 7.66 (s, 1H), 7.92 (s, 1H), 7.98 (s, 1H).

Reference Example 22

Methyl 3-formyl-5-[methyl(methylsulfonyl)amino]benzoate

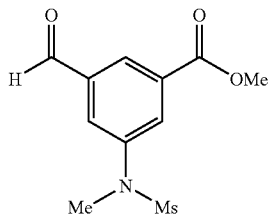

A mixture of methyl 3-(hydroxymethyl)-5-[methyl(methylsulfonyl)amino]benzoate obtained in Reference Example 21 1.10 g (4.0 mmol), manganese dioxide 3.38 g (39 mmol) and ethyl acetate (40 mL) was stirred at 70° C. for 2.5 hours. The mixture was filtered on Celite to remove the precipitates, and the solvent was concentrated to give 0.847 g (3.1 mmol) of the title compound (yield: 78%).

$^1$H-NMR (400 MHz, CDCl$_3$): δ 2.90 (s, 3H), 3.41 (s, 3H), 3.98 (s, 3H), 8.10 (dd, 1H, J=1.5, 2.2 Hz), 8.29 (dd, 1H, J=1.6, 2.2 Hz), 8.45 (t, 1H, J=1.4 Hz).

Reference Example 23

3-(2-Cyclopropylvinyl)-5-[methyl(methylsulfonyl)amino]benzoic acid

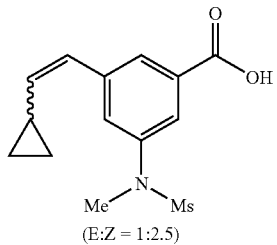

(E:Z = 1:2.5)

A solution of cyclopropylmethyl bromide 0.97 mL (10 mmol) and triphenylphosphine 2.62 g (10 mmol) in xylene (10 mL) was stirred at 140° C. for 6 hours. The resulting white precipitates were collected by filtering and washed with diethylether to give phosphonium salt 2.15 g (5.4 mmol). A mixture of the phosphonium salt 0.596 g (1.50 mmol), tert-butoxy potassium 0.168 g (1.50 mmol) and tetrahydrofuran (3 mL) was stirred at 60° C. for 30 minutes and thereto was added methyl 3-formyl-5-[methyl(methylsulfonyl)amino]benzoate 0.271 g (1.00 mmol) obtained in Reference Example 22 and the mixture was stirred at 80° C. for 2.5 hours. To the reaction solution was added water and the mixture was extracted with ethyl acetate. After drying of the mixture on MgSO$_4$, the mixture was concentrated and the residue was purified by a column chromatography on silica gel (eluted with hexane/ethyl acetate=5:1→3:1).

The resulting solid was dissolved in a mixture of 2N aqueous sodium hydroxide solution (2 mL), methanol (2 mL) and tetrahydrofuran (2 mL) and the mixture was stirred at room temperature for 15 hours. The solvent was concentrated, and the residue was adjusted by adding 1N hydrochloric acid to pH=3 and the mixture was extracted with ethyl acetate. After drying of the mixture on magnesium sulfate, the solvent was evaporated to give 236 mg (0.80 mmol, 80%) of the title compound ((E):(Z)=1:2.5) (yield: 80%).

(E)-form $^1$H-NMR (400 MHz, CDCl$_3$): δ 0.56-0.60 (m, 2H), 0.85-0.93 (m, 2H), 1.55-1.63 (s, 1H), 2.87 (s, 3H), 3.36 (s, 3H), 5.85 (dd, 1H, J=9.1, 15.7 Hz), 6.49 (d, 1H, J=15.8 Hz), 7.59 (s, 1H), 7.82 (s, 1H), 7.95 (s, 1H).

(Z)-form $^1$H-NMR (400 MHz, CDCl$_3$): δ 0.50-0.66 (m, 2H), 0.85-0.93 (m, 2H), 1.80-1.90 (s, 1H), 2.89 (s, 3H), 3.38 (s, 3H), 5.21 (dd, 1H, J=10.1, 11.4 Hz), 6.34 (d, 1H, J=11.5 Hz), 7.76 (s, 1H), 7.88 (s, 1H), 8.08 (s, 1H).

Example 9

N-[1-Benzyl-2-hydroxy-3-(1H-imidazoyl-2-ylamino)-3-oxopropyl]-3-(2-cyclopropylvinyl)-5-[methyl(methylsulfonyl)amino]benzamide

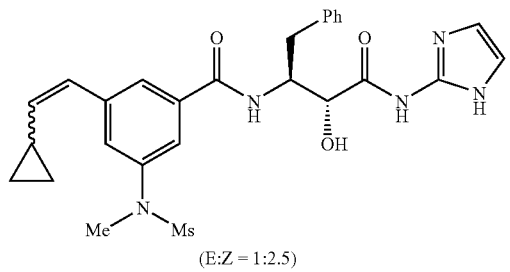

(E:Z = 1:2.5)

The title compound was prepared using (2R,3S)-3-amino-2-hydroxy-N-1H-imidazol-2-yl-4-phenylbutanamide 2 hydrochloric acid salts obtained in Reference Example 3 and 3-(2-cyclopropylvinyl)-5-[methyl(methylsulfonyl)amino]benzoic acid obtained in Reference Example 23 according to the method of Example 1.

$^1$H-NMR (400 MHz, CDCl$_3$): δ 0.46-0.55 (m, 2H), 0.81-0.88 (m, 2H), 1.50-1.77 (m, 1H), 2.81 (s, 3H), 3.12 (d, 2H, J=7.9 Hz), 3.25 and 3.27 (s, 3H), 4.44 (s, 1H), 4.89-4.97 (m, 1H), 5.10-5.17 and 5.68-5.77 (m, 1H), 6.23 and 6.37 (d, 1H, J=11.5, 15.6 Hz), 6.89-6.99 (s, 4H), 7.20-7.34 (m, 4H), 7.39 (d, 1H, J=9.1 Hz), 7.47 (d, 1H, J=7.8 Hz), 7.54 (s, 1H).

Reference Example 24

3-(2-Cyclopropylethyl)-5-[methyl(methylsulfonyl)amino]benzoic acid

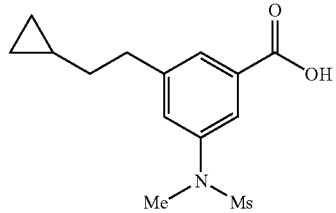

A mixture of 3-(2-cyclopropylvinyl)-5-[methyl(methylsulfonyl)amino]benzoic acid obtained in Reference Example 23 89 mg (0.30 mmol), 10% Pd/C (50% wet) 30 mg, methanol (1 mL) and ethyl acetate (1 mL) was stirred at room temperature under hydrogen atmosphere for 1.5 hours. The reaction solution was filtered on Celite and the solvent was evaporated to give 89 mg (0.30 mmol, 100%) of the title compound (yield: 100%).

$^1$H-NMR (400 MHz, CDCl$_3$): δ 0.02-0.06 (m, 2H), 0.42-0.47 (m, 2H), 0.64-0.74 (m, 1H), 1.51-1.57 (m, 2H), 3.31 (t, 2H, J=7.6 Hz), 2.87 (s, 3H), 3.36 (s, 3H), 7.49-7.53 (m, 1H), 7.84-7.89 (m, 1H).

Example 10

N-[1-Benzyl-2-hydroxy-3-(1H-imidazoyl-2-ylamino)-3-oxopropyl]-3-(2-cyclopropylethyl)-5-[methyl(methylsulfonyl)amino]benzamide

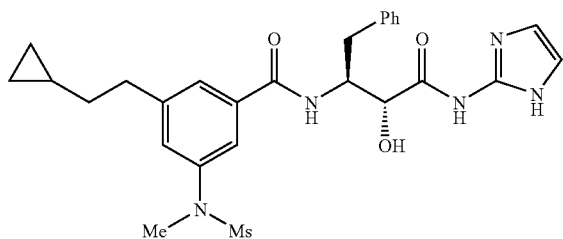

The title compound was prepared using (2R,3S)-3-amino-2-hydroxy-N-1H-imidazol-2-yl-4-phenylbutanamide 2 hydrochloric acid salts obtained in Reference Example 3 and 3-(2-cyclopropylethyl)-5-[methyl(methylsulfonyl)amino] benzoic acid obtained in Reference Example 24 according to the method of Example 1.

$^1$H-NMR (400 MHz, DMSO-d$_6$): δ-0.06-0.03 (m, 2H), 0.32-0.37 (m, 2H), 0.58-0.67 (m, 1H), 1.38-1.45 (m, 2H), 2.63 (t, 2H, J=7.7 Hz), 2.89 (s, 3H), 2.91-3.05 (m, 2H), 3.16 (s, 3H), 4.29 (s, 1H), 4.53-4.62 (m, 1H), 6.60 (s, 1H), 7.13-7.18 (m, 3H), 7.21-7.26 (m, 2H), 7.26-7.31 (m, 2H), 7.33 (s, 1H), 7.41 (s, 1H), 8.16 (d, 1H, J=8.8 Hz), 11.85 (s, 1H).

Reference Example 25

(2R,3S)-2-Hydroxy-3-{[3-[methyl(methylsulfonyl)amino]-5-({[(1R)-1-phenylethyl]amino}carbonyl)benzoyl]amino}-4-phenylbutanoic acid methylester

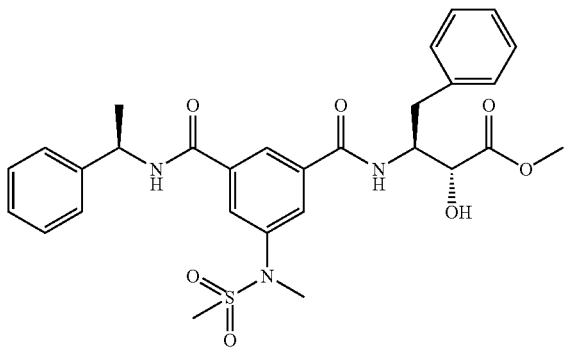

(2R,3S)-3-[(tert-butoxycarbonyl)amino]-2-hydroxy-4-phenylbutanoic acid methylester 1.55 g (5.0 mmol) was dissolved in 4N hydrochloric acid/dioxane and the mixture was stirred at room temperature for 3 hours and concenrated under reduced pressure. The concentrated residue was redissolved by adding N,N-dimethylformamide 15 mL and thereto were added triethylamine 2.16 mL (15.5 mmol), 3-[methyl(methylsulfonyl)amino]-5-({[(1R)-1-phenylethyl]amino}carbonyl)-benzoic acid 1.88 g (5.0 mmol) obtained in Reference Example 7 and HBTU 1.99 g (5.25 mmol) under ice-cooling and the resulting mixture was stirred at room temperature overnight. After completion of the reaction, the reaction solution was extracted by adding ethyl acetate and water. The organic layer was washed with 5% aqueous sodium carbonate solution, 1N hydrochloric acid and an aqueous saturated sodium chloride solution and dried on magnesium sulfate. The reaction mixture was filtered and concentrated and the resulting residue was recrystallized from a mixed solvent of ethyl acetate and hexane. A precipitated material was collected by filtering and dried to give 2.31 g (4.08 mmol) of the title compound (yield: 82%).

MS (LC/MS): 568 [M+H]$^+$ $^1$H-NMR (400 MHz, DMSO-d$_6$): δ 1.51 (d, 3H, J=7.04 Hz), 2.86-3.03 (m, 5H), 3.30 (s, 3H), 3.57 (s, 3H), 4.15-4.18 (m, 1H), 4.49-4.56 (m, 1H), 5.19 (5, 1H, J=7.36 Hz), 5.78 (d, 1H, J=6.48 Hz), 7.16-7.41 (m, 10H), 7.88 (s, 1H), 7.99 (s, 1H), 8.17 (s, 1H), 8.38 (d, 1H, J=9.00 Hz), 9.01 (d, 1H, J=7.96 Hz).

Reference Example 26

(2R,3S)-3-{[3-[Methyl(methylsulfonyl)amino]-5-({[(1R)-1-phenylethyl]-amino}carbonyl)benzoyl]amino}-4-phenyl-2-(tetrahydro-2H-pyran-2-yloxy)butanoic acid methylester

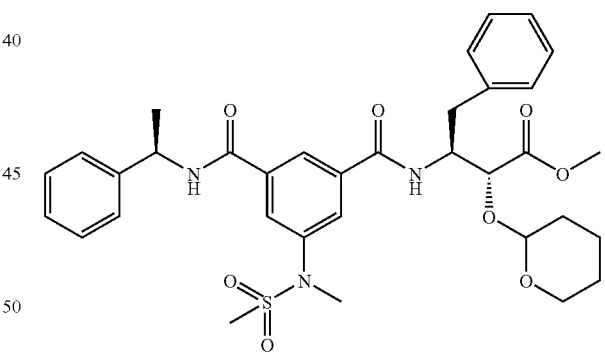

The (2R,3S)-2-hydroxy-3-{[3-[methyl(methylsulfonyl)amino]-5-({[(1R)-1-phenylethyl]amino}carbonyl)benzoyl]amino}-4-phenylbutanoic acid methylester obtained in Reference Example 25 2.30 g (4.06 mmol) was dissolved in tetrahydrofuran 8 mL and thereto were added 3,4-dihydro-2H-pyrane 4.80 mL and p-toluenesulfonic acid pyridinium 204 mg (0.81 mmol) and the mixture was stirred under reflux for 8 hours. After distillating tetrahydrofuran off, the residue was extracted by adding ethyl acetate and 5% aqueous sodium carbonate solution. The organic layer was washed with an aqueous saturated sodium chloride solution and dried on magnesium sulfate, filtered and concentrated. The concentrated residue was purified by a column chromatography on silica gel (eluted with chloroform-methanol system) and recrystallized from a mixed solvent of ethyl acetate and hexane. A precipitated material was collected by filtering and dried to give 1.81 g (2.78 mmol) of the title compound (yield: 69%).

MS (LC/MS): 652 [M+H]$^+$ $^1$H-NMR (400 MHz, DMSO-d$_6$): δ 1.44-1.83 (m, 9H), 2.89-3.02 (m, 5H), 3.29 (s, 3H), 3.46-3.49 (m, 1H), 3.62 (d, 3H, J=5.96 Hz), 3.76-3.83 (m, 1H), 4.18-4.19 (m, 1H), 4.46-4.53 (m, 1H), 4.57-4.62 (m, 1H), 5.18 (5, 1H, J=7.24 Hz), 7.13-7.41 (m, 10H), 7.83 (s, 1H), 7.98 (s, 1H), 8.13 (s, 1H), 8.51-8.55 (m, 1H), 9.00 (d, 1H, J=7.92 Hz).

Reference Example 27

(2R,3S)-3-{[3-[Methyl(methylsulfonyl)amino]-5-({[(1R)-1-phenylethyl]-amino}carbonyl)benzoyl]amino}-4-phenyl-2-(tetrahydro-2H-pyran-2-yloxy)butanoic acid

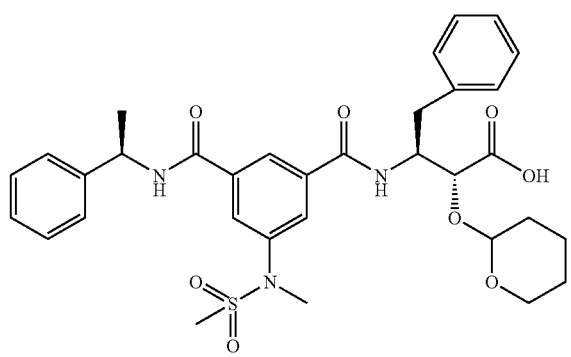

The (2R,3S)-3-{[3-[methyl(methylsulfonyl)amino]-5-({[(1R)-1-phenylethyl]amino}carbonyl)benzoyl]amino}-4-phenyl-2-(tetrahydro-2H-pyran-2-yloxy)butanoic acid methylester obtained in Reference Example 26 1.79 g (2.75 mmol) was dissolved in methanol 6 mL and thereto was added 5N aqueous sodium hydroxide solution 1.10 mL under ice-cooling and the mixture was stirred at room temperature for 6 hours. After distillating methanol off, the mixture was washed with ether. The aqueous layer was adjusted with diluted hydrochloric acid to pH 3 under ice-cooling and extracted with chloroform. The organic layer was washed with an aqueous saturated sodium chloride solution and dried on magnesium sulfate, filtered and concentrated to give 1.74 g (2.73 mmol) of the title compound (yield: 99%).

MS (LC/MS): 638 [M+H]$^+$ $^1$H-NMR (400 MHz, DMSO-d$_6$): δ 1.46-1.82 (m, 9H), 2.85-3.02 (m, 5H), 3.29 (s, 3H), 3.45-3.48 (m, 1H), 3.79-3.87 (m, 1H), 4.31-4.32 (m, 1H), 4.47-4.54 (m, 1H), 4.60-4.70 (m, 1H), 5.18 (5, 1H, J=7.32 Hz), 7.13-7.85 (m, 10H), 7.85 (s, 1H), 7.97 (s, 1H), 8.15 (s, 1H), 8.46 (d, 1H, J=9.00 Hz), 9.01 (d, 1H, J=7.92 Hz), 12.85 (br, 1H).

Example 11

N-[1-Benzyl-3-(4,5-dihydro-1H-imidazoyl-2-ylamino)-2-hydroxy-3-oxopropyl]-5-[methyl(methylsulfonyl)amino]-N'-(1-phenylethyl)isophthalamide

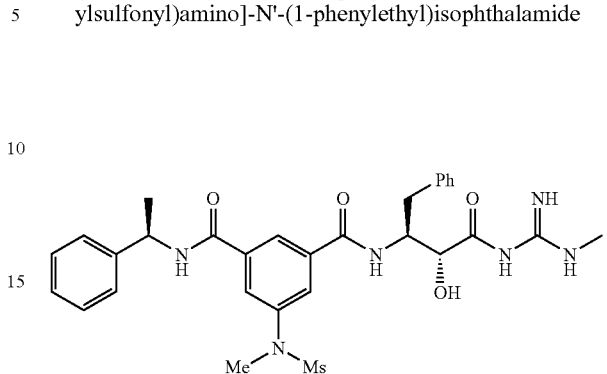

A 0.5 mL solution of (2R,3S)-3-{[3-[methyl(methylsulfonyl)amino]-5-({[(1R)-1-phenylethyl]amino}carbonyl)benzoyl]amino}-4-phenyl-2-(tetrahydro-2H-pyran-2-yloxy)butanoic acid obtained in Reference Example 27 32 mg (0.05 mmol) and 1,1'-carbonylbis-1H-imidazole 9.7 mg (0.06 mmol) in N,N-dimethylformamide was stirred at room temperature for 1 hour and the reaction mixture was added to a mixture of 1-methyguanidine hydrochloric acid salt 55 mg (0.50 mmol), triethylamine 0.070 mL (0.50 mmol) and N,N-dimethylformamide (0.5 mL) dropwise. The mixture was stirred at room temperature for 16 hours and the reaction solution was diluted with ethyl acetate and washed with saturated aqueous sodium bicarbonate solution. After drying of the mixture on magnesium sulfate, the solvent was evaporated and the residue was dissolved in chloroform (0.5 mL) and trifluoroacetic acid (0.5 mL) and the resulting mixture was stirred at room temperature for 2 hours. The reaction solution was poured into an ice-cooled aqueous sodium bicarbonate solution and the mixture was extracted with ethyl acetate. After drying of the mixture on magnesium sulfate, the solvent was evaporated and the residue was purified by a fraction collector.

$^1$H-NMR (400 MHz, DMSO-d$_6$): δ 1.46 (d, 3H, J=7.0 Hz), 2.79 (d, 3H, J=5.0 Hz), 2.95-3.00 (m, 5H), 3.25 (s, 3H), 4.21 (s, 1H), 4.49-4.56 (m, 1H), 5.10-5.18 (m, 1H), 6.81 (s, 1H), 7.13-7.37 (m, 10H), 7.80 (s, 1H), 7.96 (s, 1H), 8.10 (s, 1H), 8.36 (d, 1H, J=8.6 Hz), 8.97 (d, 1H, J=8.1 Hz), 10.81 (s, 1H), 14.28 (s, 1H).

Reference Example 28

2-Amino-4,5-dihydroimidazole hydroiodic acid salt

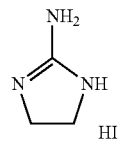

A mixture of 2-methylthio-4,5-dihydroimidazole hydroiodic acid salt 2.44 g (10 mmol), methanol (3 mL) and 28% aqueous ammonia (2 mL) was stirred at 80° C. for 4 hours. The reaction solution was concentrated and ice-cooled, and the precipitated solid was collected by filtering, washed with diethylether and dried under vacuum to give 1.71 g (8.0 mmol) of the title compound (yield: 80%).

$^1$H-NMR (400 MHz, DMSO-d$_6$): δ 3.55 (s, 4H), 7.67 (s, 2H), 7.76 (s, 2H).

Example 12

N-[1-Benzyl-3-(4,5-dihydro-1H-imidazoyl-2-ylamino)-2-hydroxy-3-oxopropyl]-5-[methyl(methylsulfonyl)amino]-N'-(1-phenylethyl)isophthalamide

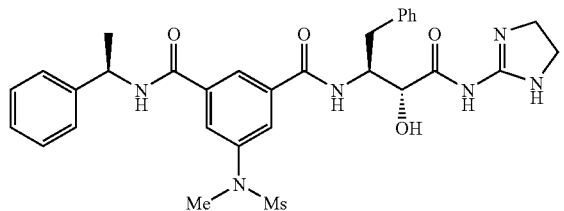

The title compound was prepared using (2R,3S)-3-{[3-[methyl(methylsulfonyl)amino]-5-({[(1R)-1-phenylethyl]amino}carbonyl)-benzoyl]amino}-4-phenyl-2-(tetrahydro-2H-pyran-2-yloxy)butanoic acid obtained in Reference Example 27 and 2-amino-4,5-dihydroimidazole hydroiodic acid salt obtained in Reference Example 28 according to the method of Example 11.

$^1$H-NMR (400 MHz, DMSO-d$_6$): δ 1.50 (d, 3H, J=7.0 Hz), 2.95-3.05 (m, 5H), 3.29 (s, 3H), 3.67 (s, 4H), 4.28 (s, 1H), 4.52-4.61 (m, 1H), 5.13-5.21 (m, 1H), 6.71 (s, 1H), 7.15-7.41 (m, 10H), 7.84 (s, 1H), 8.00 (s, 1H), 8.14 (s, 1H), 8.40 (d, 1H, J=8.7 Hz), 8.79 (s, 1H), 9.00 (d, 1H, J=8.0 Hz), 11.66 (s, 1H).

Example 13

N-[1-Benzyl-2-hydroxy-3-oxo-3-(1H-tetrazoyl-5-ylamino)propyl]-5-[methyl(methylsulfonyl)amino]-N'-(1-phenylethyl)isophthalamide

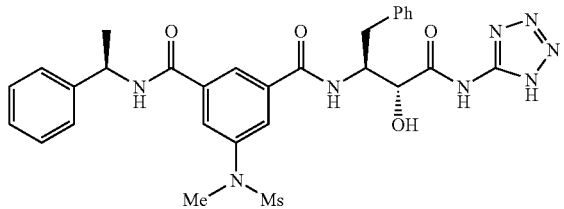

The title compound was prepared using (2R,3S)-3-{[3-[methyl(methylsulfonyl)amino]-5-({[(1R)-1-phenylethyl]amino}carbonyl)-benzoyl]amino}-4-phenyl-2-(tetrahydro-2H-pyran-2-yloxy)butanoic acid obtained in Reference Example 27 and 5-amino-1H-tetrazole according to the method of Example 11.

$^1$H-NMR (400 MHz, DMSO-d$_6$): δ 1.46 (d, 3H, J=7.0 Hz), 2.95-3.00 (m, 5H), 3.21 (s, 3H), 4.36 (s, 1H), 4.64-4.71 (m, 1H), 5.10-5.18 (m, 1H), 6.10 (s, 1H), 7.13-7.41 (m, 10H), 7.81 (s, 1H), 7.95 (s, 1H), 8.12 (s, 1H), 8.37 (d, 1H, J=8.6 Hz), 8.99 (d, 1H, J=8.2 Hz), 11.99 (s, 1H), 15.84 (s, 1H).

Example 14

N-[(1S,2R)-1-Benzyl-2-hydroxy-3-(1H-benzimidazol-2-ylamino)-3-oxopropyl]-5-[methyl(methylsulfonyl)amino]-N'-[(1R)-1-phenylethyl]-isophthalamide

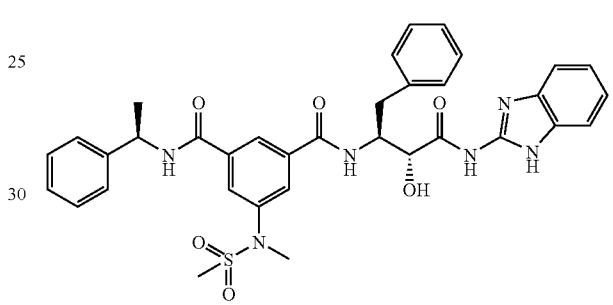

To a 2 mL solution of (2R,3S)-3-{[3-[methyl(methylsulfonyl)amino]-5-({[(1R)-1-phenylethyl]amino}carbonyl)benzoyl]amino}-4-phenyl-2-(tetrahydro-2H-pyran-2-yloxy)butanoic acid obtained in Reference Example 27 64 mg (0.1 mmol), 2-aminobenzimidazole 27 mg (0.2 mmol), HOBt.H$_2$O 31 mg (0.2 mmol) and 4-(dimethylamino)pyridine 2.4 mg (0.02 mmol) in N,N-dimethylformamide was added a polystyrene-supported carbodiimide (1.38 mmol/g) 181 mg (equivalent to carbodiimide 0.25 mmol) and the mixture was shaken overnight. After completion of the reaction, the mixture was filtered and the filtrate was extracted by adding ethyl acetate and 5% aqueous sodium carbonate solution. The organic layer was washed with an aqueous saturated sodium chloride solution and dried on the magnesium sulfate, filtered and concentrated. The concentrated residue was redissolved in chloroform 2 mL and thereto was added TFA 1 mL and the mixture was stirred at room temperature for 3 hours to remove the protecting group. After completion of the reaction, the mixture was concentrated and the concentrated residue was purified by HPLC fraction collector to give 32 mg (0.05 mmol) of the title compound (overall yields: 48%).

MS (LC/MS): 669 [M+H]$^+$ $^1$H-NMR (400 MHz, DMSO-d$_6$): δ 1.47 (d, 3H, J=7.04 Hz), 2.97-3.10 (m, 5H), 3.24 (s, 3H), 4.42 (m, 1H), 4.71 (m, 1H), 5.16 (m, 1H), 6.43 (br, 1H), 7.16-7.55 (m, 12H), 7.56 (d, 1H, J=3.20 Hz), 7.57 (d, 1H, J=3.16 Hz), 7.82 (s, 1H), 7.96 (s, 1H), 8.13 (s, 1H), 8.45 (d, 1H, J=8.84 Hz), 8.97 (d, 1H, J=7.96 Hz), 12.12 (br, 1H).

Example 15

N-[(1S,2R)-1-Benzyl-2-hydroxy-3-(1H-5-phenylimidazol-2-ylamino)-3-oxopropyl]-5-[methyl(methylsulfonyl)amino]-N'-[(1R)-1-phenylethyl]isophthalamide

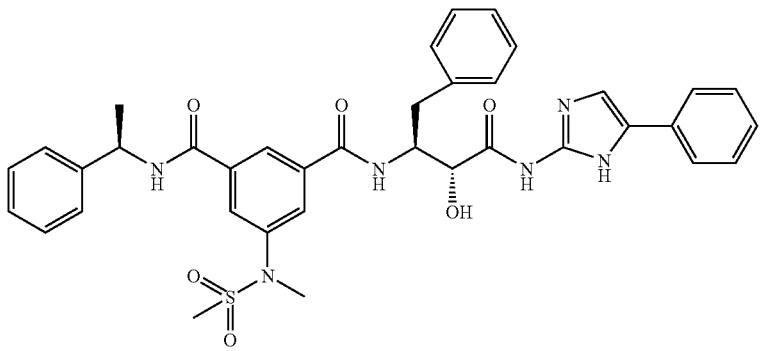

To a 14 mL solution of 2-amino-5-phenylimidazole.½ sulphate salt 42 mg (0.2 mmol) in methanol was added a 0.2 mL solution of 1N sodium methoxide in methanol under ice-cooling, and the mixture was stirred at room temperature for 1 hour and concentrated. To the concentrated residue were added a 3 mL solution of (2R,3S)-3-{[3-[methyl(methylsulfonyl)amino]-5-({[(1R)-1-phenylethyl]amino}carbonyl)-benzoyl]amino}-4-phenyl-2-(tetrahydro-2H-pyran-2-yloxy) butanoic acid obtained in Reference Example 27 85 mg (0.13 mmol), HOBt.H$_2$O 23 mg (0.15 mmol) and WSC.HCl 76 mg (0.4 mmol) in N,N-dimethylformamide and the mixture was stirred at room temperature overnight. After completion of the reaction, the reaction solution was extracted by adding ethyl acetate and 5% aqueous sodium carbonate solution. The organic layer was washed with an aqueous saturated sodium chloride solution and dried on magnesium sulfate, filtered and concentrated. The concentrated residue was redissolved in chloroform 1.5 mL and thereto was added TFA 1.5 mL to remove the protecting group. After completion of the reaction, the mixture was concentrated and the concentrated residue was purified by HPLC fraction collector to give 12 mg (0.02 mmol) of the title compound (overall yields: 13%).

MS (LC/MS): 695 [M+H]$^+$ $^1$H-NMR (400 MHz, DMSO-d$_6$): δ 1.54 (d, 3H, J=7.04 Hz), 2.99-3.09 (m, 5H), 3.32 (s, 3H), 4.34 (m, 1H), 4.74 (m, 1H), 5.23 (m, 1H), 6.01 (d, 1H, J=6.04 Hz), 7.21-7.47 (m, 15H), 7.76 (d, 2H, J=7.36 Hz), 7.92 (s, 1H), 8.02 (s, 1H), 8.42 (s, 1H), 9.05 (d, 1H, J=7.96), 11.08 (br, 1H), 11.71 (s, 1H).

Example 16

N-[(1S,2R)-1-Benzyl-2-hydroxy-3-(1H-5-methylimidazol-2-ylamino)-3-oxopropyl]-5-[methyl(methylsulfonyl)amino]-N'-[(1R)-1-phenylethyl]isophthalamide

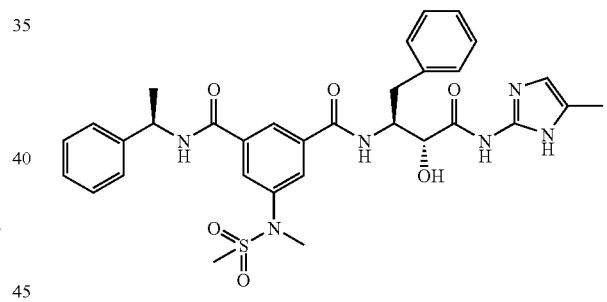

To a 3 mL solution of (2R,3S)-3-{[3-[methyl(methylsulfonyl)amino]-5-({[(1R)-1-phenylethyl]amino}carbonyl)benzoyl]amino}-4-phenyl-2-(tetrahydro-2H-pyran-2-yloxy) butanoic acid obtained in Reference Example 27 246 mg (0.39 mmol), 2-amino-5-methylimidazole 75 mg (0.77 mmol) and HBTU 155 mg (0.41 mmol) in N,N-dimethylformamide was added triethylamine 0.11 mL (0.80 mmol) under ice-cooling and the mixture was stirred at room temperature overnight. After completion of the reaction, the reaction solution was extracted by adding ethyl acetate and 5% aqueous sodium carbonate solution. The organic layer was washed with an aqueous saturated sodium chloride solution and dried on sodium sulfate, filtered and concentrated. The concentrated residue was redissolved in chloroform 2 mL and thereto was added TFA 2 mL to remove the protecting group. After completion of the reaction, the mixture was concentrated and the concentrated residue was purified by HPLC fraction collector to give 32 mg (0.05 mmol) of the title compound (overall yields: 13%).

MS (LC/MS): 633 [M+H]$^+$ $^1$H-NMR (400 MHz, DMSO-d$_6$): δ 1.49 (d, 3H, J=7.04 Hz), 2.03 (br, 3H), 2.89-3.05 (m, 5H), 3.28 (s, 3H), 4.19 (m,

1H), 4.61 (m, 1H), 5.17 (5, 1H, J=7.36 Hz), 6.00 (br, 1H), 6.42 (br, 1H), 7.14-7.40 (m, 10H), 7.83 (s, 1H), 7.95 (s, 1H), 8.15 (s, 1H), 8.31 (d, 1H, J=8.92 Hz), 9.00 (d, 1H, J=7.92 Hz), 10.59 (br, 1H), 11.23 (br, 1H)

Example 17

N-[(1S,2R)-1-Benzyl-2-hydroxy-3-(1H-5-ethylimidazol-2-ylamino)-3-oxopropyl]-5-[methyl(methylsulfonyl)amino]-N'-[(1R)-1-phenylethyl]isophthalamide

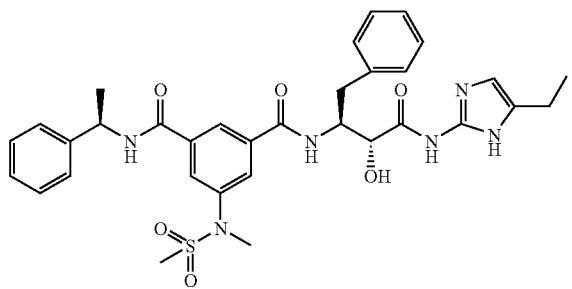

The title compound was prepared using (2R,3S)-3-{[3-[methyl(methylsulfonyl)amino]-5-({[(1R)-1-phenylethyl] amino}carbonyl)-benzoyl]amino}-4-phenyl-2-(tetrahydro-2H-pyran-2-yloxy)butanoic acid obtained in Reference Example 27 and 2-amino-5-ethylimidazole according to the method of Example 16.

MS (LC/MS): 647 [M+H]$^+$ $^1$H-NMR (400 MHz, DMSO-d$_6$): δ 1.09 (t, 3H, J=7.56 Hz), 1.49 (d, 3H, J=7.04 Hz), 2.40 (br, 2H), 2.89-3.01 (m, 5H), 3.26 (s, 3H), 4.19 (m, 1H), 4.61 (m, 1H), 5.17 (5, 1H, J=7.32 Hz), 5.94 (br, 1H), 6.40 (br, 1H), 7.14-7.40 (m, 10H), 7.83 (s, 1H), 7.96 (s, 1H), 8.15 (s, 1H), 8.32 (d, 1H, J=8.96 Hz), 9.00 (d, 1H, J=7.92 Hz), 10.66 (br, 1H), 11.17 (br, 1H).

Example 18

N-[(1S,2R)-1-Benzyl-2-hydroxy-3-(1H-4,5-dimethylimidazol-2-ylamino)-3-oxopropyl]-5-[methyl(methylsulfonyl)amino]-N'-[(1R)-1-phenylethyl]isophthalamide

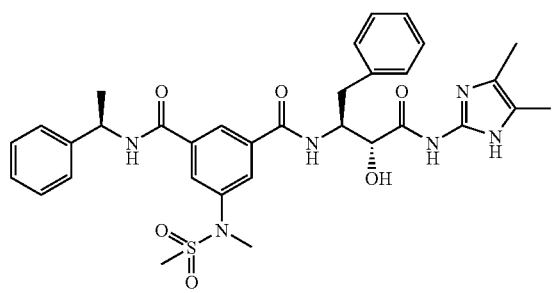

To an 0.2 mL aqueous solution of 2-amino-4,5-dimethylimidazole.ethylsulphate salt 47 mg (0.2 mmol) was added 10N aqueous sodium hydroxide solution 0.02 mL under ice-cooling. Thereto were added a solution of (2R,3S)-3-{[3-[methyl(methylsulfonyl)amino]-5-({[(1R)-1-phenylethyl] amino}carbonyl)benzoyl]amino}-4-phenyl-2-(tetrahydro-2H-pyran-2-yloxy)butanoic acid obtained in Reference Example 27 64 mg (0.1 mmol), HOBt.H$_2$O 18 mg (0.12 mmol) and WSC.HCl 29 mg (0.15 mmol) in N,N-dimethylformamide 2 mL and the mixture was stirred at 50° C. for 9 hours. After completion of the reaction, the reaction solution was extracted by adding ethyl acetate and 5% aqueous sodium carbonate solution. The organic layer was washed with an aqueous saturated sodium chloride solution, dried on magnesium sulfate, filtered and concentrated. The concentrated residue was redissolved in chloroform 1.5 mL and thereto was added TFA 1.5 mL to remove the protecting group. After completion of the reaction, the mixture was concentrated and the concentrated residue was purified with HPLC fraction collector to give 18 mg (0.03 mmol) of the title compound (overall yields: 27%).

MS (LC/MS): 647 [M+H]$^+$ $^1$H-NMR (400 MHz, DMSO-d$_6$): δ 1.49 (d, 3H, J=7.00 Hz), 1.96 (br, 6H), 2.83-3.03 (m, 5H), 3.26 (s, 3H), 4.14 (m, 1H), 4.59 (m, 1H), 5.17 (m, 1H), 6.02 (br, 1H), 7.15-7.40 (m, 10H), 7.83 (s, 1H), 7.96 (s, 1H), 8.15 (s, 1H), 8.31 (d, 1H, J=8.72 Hz), 9.01 (d, 1H, J=7.80 Hz), 10.45 (br, 1H), 11.58 (br, 1H).

Example 19

N-{(1S)—1-[(1R)-1-Hydroxy-2-(1H-imidazol-2-ylamino)-2-oxoethyl]-3-methylbutyl}-5-[methyl(methylsulfonyl)amino]-N'-[(1R)-1-phenylethyl]isophthalamide

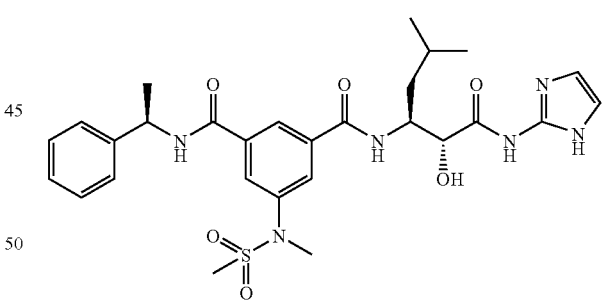

The title compound was prepared using (2R,3S)-3-[(tert-butoxycarbonyl)amino]-2-hydroxy-5-methylhexanoic acid according to the methods of Reference Examples 1, 2 and 3 and Example 1.

MS (LC/MS): 585 [M+H]$^+$ $^1$H-NMR (400 MHz, DMSO-d$_6$): δ 0.90 (d, 3H, J=6.12 Hz), 0.91 (d, 3H, J=5.60 Hz), 1.40-1.47 (m, 1H), 1.50 (d, 3H, J=7.08 Hz), 1.57-1.66 (m, 1H), 1.68-1.75 (m, 1H), 3.01 (s, 3H), 3.28 (s, 3H), 4.31 (br, 1H), 4.53 (m, 1H), 5.18 (m, 1H), 6.52 (br, 1H), 7.20-7.41 (m, 7H), 7.91 (s, 1H), 8.00 (s, 1H), 8.26 (s, 1H), 8.31 (d, 1H, J=8.84 Hz), 9.06 (d, 1H, J=8.00 Hz), 12.01 (br, 1H), 13.05 (br, 1H).

Example 20

N-[(1S,2R)-1-(3,5-Difluorobenzyl)-2-hydroxy-3-(1H-imidazol-2-ylamino)-3-oxopropyl]-5-[methyl(methylsulfonyl)amino]-N'-[(1R)-1-phenylethyl]isophthalamide

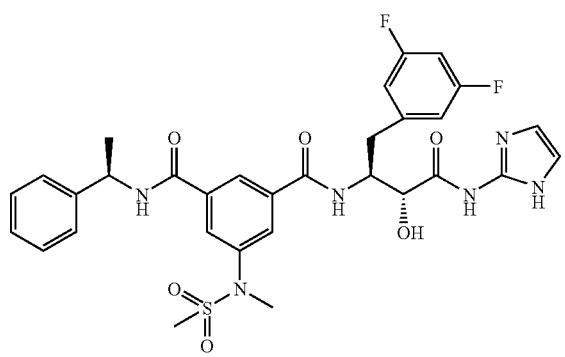

The title compound was prepared using (2R,3S)-3-[(tert-butoxycarbonyl)amino]-2-hydroxy-4-(3,5-difluorophenyl)butanoic acid according to the method of Example 19.

MS (LC/MS): 655 [M+H]$^+$ $^1$H-NMR (400 MHz, DMSO-d$_6$): δ 1.49 (d, 3H, J=7.04 Hz), 2.89-3.06 (m, 5H), 3.34 (s, 3H), 4.33 (br, 1H), 4.67 (m, 1H), 5.17 (m, 1H), 6.41 (br, 1H), 6.98 (br, 2H), 7.02-7.04 (m, 3H), 7.29-7.39 (m, 5H), 7.82 (s, 1H), 7.98 (s, 1H), 8.13 (s, 1H), 8.37 (d, 1H, J=9.12 Hz), 8.99 (d, 1H, J=7.88 Hz), 11.43 (br, 1H), 12.59 (br, 1H).

Reference Example 29 tert-Butyl [(1S,2R)-3-(1H-benzimidazolyl-2-ylamino)-1-benzyl-2-hydroxy-3-oxopropyl]carbamate

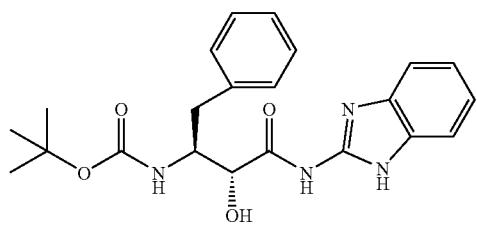

(2R,3S)-3-[(tert-Butoxycarbonyl)amino]-2-hydroxy-4-phenylbutanoic acid (295 mg) was dissolved in N,N-dimethylformamide and thereto were added 2-aminobenzimidazole (107 mg), WSC.HCl (191 mg), HOBt.H$_2$O (153 mg) and triethylamine (0.112 mL) and the mixture was stirred overnight. The reaction mixture was concenrated under reduced pressure and the residue was dissolved in ethyl acetate and washed with 5% aqueous citrate solution, 5% aqueous sodium carbonate solution and an aqueous saturated sodium chloride solution and dried on anhydride sodium sulfate. The solvent was concenrated under reduced pressure to give the title compound 207 mg as white solid.

Reference Example 30 tert-Butyl [(1S)-1-({[(1S,2R)-3-(1H-benzimidazolyl-2-ylamino)-1-benzyl-2-hydroxy-3-oxopropyl]amino}carbonyl)-3-methylbutyl]carbamate

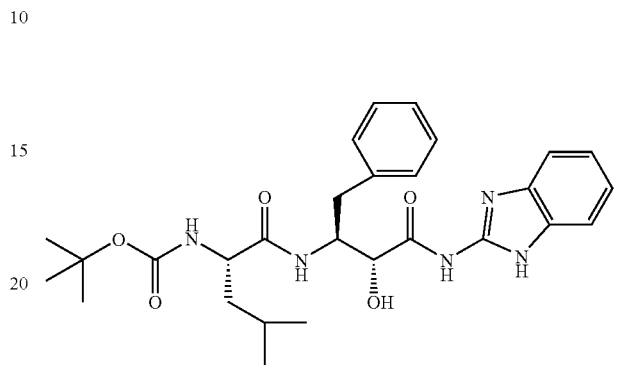

To the compound obtained in Reference Example 29 (207 mg) was added anisole (0.054 mL) and the mixture was dissolved in 4N hydrochloric acid/dioxane (3.2 mL) and the mixture was stirred at room temperature for 1 hour. The reaction mixture was concentrated under reduced pressure and the residue was precipitated with diethylether to give the hydrochloric acid salt. The hydrochloric acid salt was dissolved in N,N-dimethylformamide and the mixture was neutralized with triethylamine and thereto were added Boc-Leu-OH.H$_2$O (112 mg), WSC.HCl (86 mg) and HOBt.H$_2$O (69 mg) and the mixture was stirred overnight. The reaction mixture was concenrated under reduced pressure and the residue was dissolved in ethyl acetate ad washed with 5% aqueous citrate solution, 5% aqueous sodium carbonate solution and an aqueous saturated sodium chloride solution, and dried on anhydride sodium sulfate. The solvent was concentrated under reduced pressure to give the title compound 204 mg as white solid.

Reference Example 31

N-(Tert-butoxycarbonyl)-L-valyl-N$^1$-[(1S,2R)-3-(1H-benzimidazolyl-2-ylamino)-1-benzyl-2-hydroxy-3-oxopropyl]-L-leucinamide

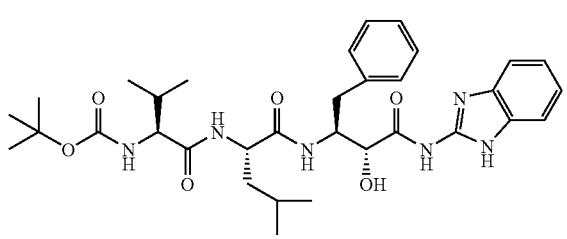

The title compound was prepared using the compound obtained in Reference Example 30 and Boc-Val-OH (76 mg) in a similar manner to Reference Example 30 to give the compound (245 mg).

Example 21

L-α-glutamyl-L-valyl-N¹-[(1S,2R)-3-(1H-benzimidazolyl-2-ylamino)-1-benzyl-2-hydroxy-3-oxopropyl]-L-leucinamide

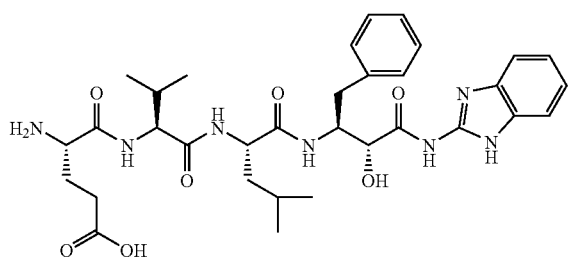

The condensation was performed using the compound obtained in Reference Example 30 (40 mg) and Boc-Glu(OtBu)-OH (19.5 mg) in a similar manner to Reference Example 30. To the resulting protected peptide derivative were then added thioanisole (0.05 mL) and m-cresol (0.05 mL) and the mixture was dissolved in trifluoroacetic acid (1.9 mL) and the mixture was stirred at room temperature for 1 hour. The solvent was concenrated under reduced pressure and the mixture was precipitated with diethylether to give the crude product. A partial of the crude product was purified by preparative HPLC to give the desired product as white powder.

HRMS (FAB): m/z (M+H)⁺ Calculated C33H45N7O7+H, 652.3459, Founded 652.3464.

Reference Example 32

Benzyl 2-amino-4-methyl-1H-imidazol-1-carboxylate

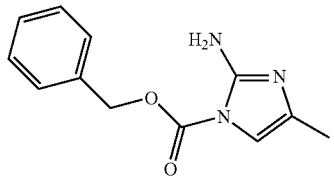

A mixture of N-benzyloxycarbonylguanidine 1.93 g (10 mmol), triethylamine 1.39 ml (10 mmol), chloroacetone 2.40 ml (30 mmol) and ethyl acetate 40 ml was stirred at 50° C. for 10 hours. The reaction solution was washed with water and an aqueous sodium chloride solution and dried on magnesium sulfate. After evaporation of the solvent, the residue was purified by a column chromatography on silica gel and further recrystallized from n-hexane to give 500 mg of the title compound (yield: 22%).

$^1$H-NMR (400 MHz, DMSO-$d_6$): δ 1.89 (d, 3H, J=1.3 Hz), 5.33 (s, 2H), 6.45 (s, 2H), 6.61 (d, 1H, J=1.3 Hz), 7.36-7.47 (m, 5H).

Reference Example 33

Benzyl 2-amino-4-ethyl-1H-imidazol-1-carboxylate

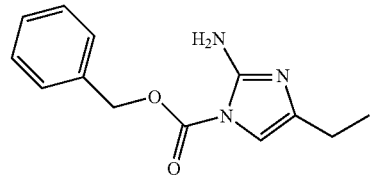

A mixture of N-benzyloxycarbonyl guanidine 2.52 g (13.1 mmol), diisopropylethylamine 1.81 ml (8.7 mmol), 1-bromo-2-butanone 0.89 ml (8.7 mmol) and ethyl acetate 50 ml was stirred at room temperature overnight. The reaction solution was washed with water and aqueous sodium chloride solution and dried on magnesium sulfate. After evaporation of the solvent, the residue was purified by a column chromatography on silica gel and further recrystallized from n-hexane to give 0.71 g of the title compound (yield: 33%).

$^1$H-NMR (400 MHz, DMSO-$d_6$): δ 1.06 (t, 3H, J=7.5 Hz), 2.26 (q, 2H, J=7.5 Hz), 5.33 (s, 2H), 6.47 (s, 2H), 6.58 (s, 1H), 7.37-7.47 (m, 5H).

Reference Example 34 tert-Butyl {(1S,2R)-1-benzyl-2-hydroxy-3-[(5-methyl-1H-imidazol-2-yl)amino]-3-oxopropyl}carbamate

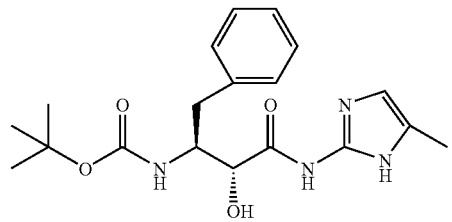

To a 5.00 ml solution of benzyl 2-amino-4-methyl-1H-imidazole-1-carboxylate obtained in Reference Example 32 601 mg (2.60 mmol), (2R,3S)-3-tert-butoxycarbonylamino-2-hydroxy-4-phenylbutanoic acid 590 mg (2.00 mmol) and HOBt.H₂O 321 mg (2.10 mmol) in DMF was added WSC.HCl 422 mg (2.20 mmol) and the mixture was stirred at room temperature for 5 hours. After distillating DMF off, the mixture was extracted by adding ethyl acetate and 5% aqueous sodium carbonate solution. The organic layer was washed with an aqueous saturated sodium chloride solution and dried on sodium sulfate. Filtration and concentration gave a residue and the resulting residue was redissolved in methanol 30 mL. To this solution were added ammonium formate 2.52 g (40.00 mmol), 10% Pd/C (containing 50% water) and the mixture was heated under reflux for 2 hours. The mixture was filtered to remove 10% Pd/C and concentrated. The concentrated residue was suspended in ethyl acetate and washed with 5% sodium carbonate and an aqueous saturated sodium chloride solution. The organic layer was dried on sodium sulfate. After filtration and concentration of the mixture, the mixture was purified by a column chromatography on silica gel (eluted with a mixed solvent of chloroform and methanol) to give 558 mg (1.49 mmol) of the title compound (yield: 75%).

MS (LC/MS): 375 [M+H]+

1H-NMR (400 MHz, DMSO-d6): δ 1.12 (s, 3H), 1.24 (s, 6H), 2.05 (s, 3H), 2.70-2.75 (m, 1H), 2.79-2.85 (m, 1H), 3.98 (br, 1H), 4.00-4.06 (m, 1H), 6.41-6.45 (br, 2H), 7.17-7.30 (m, 5H), 10.49 (br, 1H), 11.18 (br, 1H).

Reference Example 35

(2R,3S)-3-Amino-2-hydroxy-N-[(5-methyl-1H-imidazole-2-yl)-4-phenylbutanamide 2 hydrochloric acid salts

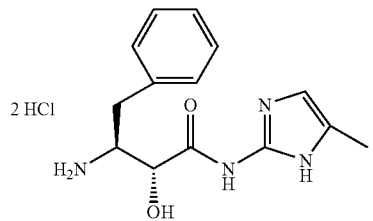

To a solution of tert-butyl {(1S,2R)-1-benzyl-2-hydroxy-3-[(5-methyl-1H-imidazol-2-yl)amino]-3-oxopropyl}carbamate obtained in Reference Example 34 449 mg (1.20 mmol) was added 4N hydrochloric acid/dioxane 12 ml under ice-cooling, and the mixture was stirred at a temperature of a range of ice-cooling to room temperature for 3 hours. The mixture was then concentrated to give 410 mg (1.18 mmol) of the title compound (yield: 98%).

MS (LC/MS): 275 [M+H]+ (free amine)

Example 22

(2R,3S)-2-Hydroxy-N-[(5-methyl-1H-imidazol-2-yl)-4-phenyl-3-[(2-thienylacetyl)amino]butanamide

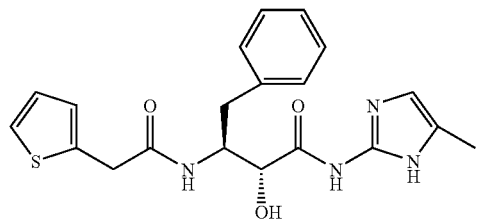

A 1 mL solution of (2R,3S)-3-amino-2-hydroxy-N-[(5-methyl-1H-imidazol-2-yl)-4-phenylbutanamide 2 hydrochloric acid salts obtained in Reference Example 35 35 mg (0.10 mmol) and HOBt.H2O 26 mg (0.17 mmol) in DMF was neutralized by adding triethylamine 0.028 ml (0.20 mmol). To this solution were added 2-thienyl acetic acid 21 mg (0.15 mmol) and PS-Carbodiimide (1.60 mmol/g, ARGONAUT Inc.) 125 mg and the mixture was stirred using a rotator at room temperature overnight. Thereto was added MP-Carbonate (2.90 mmol/g, ARGONAUT Inc.) 172 mg and the mixture was stirred at room temperature for an additional 5 hours, and HOBt.H2O and excess of 2-thienyl acetic acid were absorbed.

After filtration to remove the resins, the filtrate was extracted with ethyl acetate and 5% aqueous sodium carbonate solution. The organic layer was washed with an aqueous saturated sodium chloride solution and dried on sodium sulfate. After filtration and concentration of the mixture, the mixture was purified by HPLC fraction collector to give 15 mg (0.04 mg) of the title compound (yield: 37%).

MS (LC/MS): 399 [M+H]+

1H-NMR (400 MHz, DMSO-d6): δ 2.06 (s, 3H), 2.70-2.75 (m, 1H), 2.82-2.88 (m, 1H), 3.56 (s, 2H), 4.03 (br, 1H), 4.30-4.36 (m, 1H), 6.09 (br, 1H), 6.43 (s, 1H), 6.70-6.71 (m, 1H), 6.80-6.82 (m, 1H), 7.15-7.30 (m, 6H), 7.94 (d, 1H, J=9.00), 10.22 (br, 1H), 11.28 (br, 1H).

Example 23

Tert-butyl (4R)-4-[({(1S,2R)-1-benzyl-2-hydroxy-3-[(5-methyl-1H-imidazol-2-yl)amino]-3-oxopropyl}amino)carbonyl]-5,5-dimethyl-1,3-thiazolidine-3-carboxylate

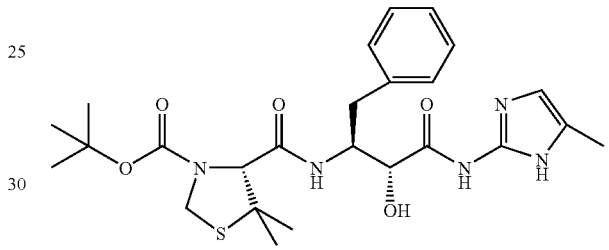

The title compound was prepared using (2R,3S)-3-amino-2-hydroxy-N-[(5-methyl-1H-imidazol-2-yl)-4-phenylbutanamide 2 hydrochloric acid salts obtained in Reference Example 35 and (4R)-3-(tert-butoxycarbonyl)-5,5-dimethyl-1,3-thiazolidine-4-carboxylic acid in a similar manner to Example 22 to give 32 mg (0.06 mmol) of the compound (yield 62%).

MS (LC/MS): 518 [M+H]+

1H-NMR (400 MHz, DMSO-d6): δ 0.93 (s, 3H), 1.35 (s, 9H), 1.40 (s, 3H), 2.05 (s, 3H), 2.73-2.89 (m, 2H), 3.89 (br, 3H), 4.22 (s, 1H), 4.34-4.39 (m, 1H), 4.48-4.54 (m, 2H), 6.40 (s, 1H), 7.21-7.36 (m, 5H), 10.03 (br, 1H), 11.23 (br, 1H).

Example 24

(2R,3S)-2-Hydroxy-N-(5-methyl-1H-imidazol-2-yl)-4-phenyl-3-{[(2E)-3-phenylprop-2-enoyl]amino}butanamide

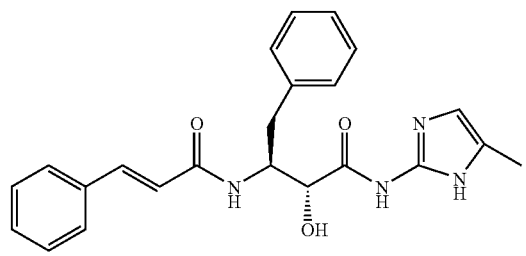

The title compound was prepared using (2R,3S)-3-amino-2-hydroxy-N-[(5-methyl-1H-imidazol-2-yl)-4-phenylbutanamide 2 hydrochloric acid salts obtained in Reference Example 35 and (2E)-3-phenylacrylic acid in a similar manner to Example 22 to give 28 mg (0.07 mmol) of the compound (yield: 69%).

MS (LC/MS): 405 [M+H]+

$^1$H-NMR (400 MHz, DMSO-$d_6$): δ 2.04 (s, 3H), 2.78-2.83 (m, 1H), 2.90-2.95 (m, 1H), 4.10 (br, 1H), 4.47-4.53 (m, 1H), 6.07 (br, 1H), 6.40 (br, 1H), 6.72 (s, 1H), 7.19-7.52 (m, 10H), 7.96 (d, 1H, J=9.00 Hz), 10.31 (br, 1H), 11.18 (br, 1H).

Example 25

(2R,3S)-3-{[(2E)-3-(2-Furyl)prop-2-enoyl]amino}-2-hydroxy-N-(5-methyl-1H-imidazol-2-yl)-4-phenylbutanamide

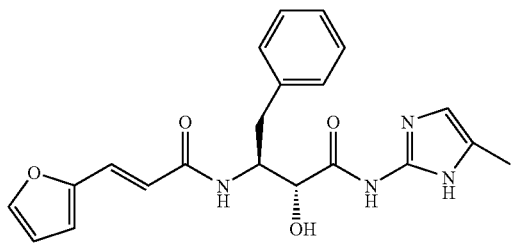

The title compound was prepared using (2R,3S)-3-amino-2-hydroxy-N-[(5-methyl-1H-imidazol-2-yl)-4-phenylbutanamide 2 hydrochloric acid salts obtained in Reference Example 35 and (2E)-3-(2-furyl)acrylic acid in a similar manner to Example 22 to give 25 mg (0.06 mmol) of the compound (yield: 63%).

MS (LC/MS): 395 [M+H]+

$^1$H-NMR (400 MHz, DMSO-$d_6$): δ 2.04 (s, 3H), 2.76-2.81 (m, 1H), 2.88-2.93 (m, 1H), 4.08 (br, 1H), 4.44-4.50 (m, 1H), 6.07 (br, 1H), 6.36-6.41 (m, 2H), 6.64 (s, 1H), 7.16-7.29 (m, 6H), 7.70 (s, 1H), 7.83 (d, 1H, J=8.96 Hz), 7.94 (s, 1H), 10.27 (br, 1H), 11.25 (br, 1H).

Reference Example 36

1-(Methylsulfonyl)piperidine-3-carboxylic acid

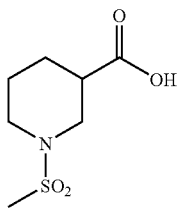

To a 3 ml solution of ethyl nicopetate 471 mg (3.00 mmol) in chloroform were added triethylamine 0.46 ml (3.30 mmol) and methanesulfonyl chloride 0.26 ml (3.30 mmol) under ice-cooling and the mixture was stirred at room temperature overnight. To this reaction solution was added 1N hydrochloric acid to remove unreacted ethyl nicopetate and the mixture was washed with 5% aqueous sodium carbonate solution and an aqueous saturated sodium chloride solution and dried on magnesium sulfate. After filtration and concentration of the mixture, the mixture was purified by a column chromatography on silica gel (eluted with a mixed solvent of chloroform and methanol) to give 451 mg (1.92 mmol) of 1-(methylsulfonyl)piperidine-3-carboxylic acid ethylester. This solution was then dissolved in methanol 10 ml and thereto was added 1N aqueous sodium hydroxide solution 2.30 ml under ice-cooling and the mixture was stirred at room temperature for 6 hours. After distilling methanol off, the mixture was washed with ether and the aqueous layer was adjusted with 1N hydrochloric acid to pH 3. The mixture was extracted with ethyl acetate and the organic layer was washed with an aqueous saturated sodium chloride solution and dried on magnesium sulfate. After filtration and concentration of the mixture, the mixture was recrystallized from a mixed solvent of ethyl acetate and hexane to give 156 mg (0.75 mmol) of the title compound (yield: 39%).

Example 26

N-{(1S,2R)-1-Benzyl-2-hydroxy-3-[(5-methyl-1H-imidazol-2-yl)amino]-3-oxopropyl}-1-(methylsulfonyl)piperidine-3-carboxamide

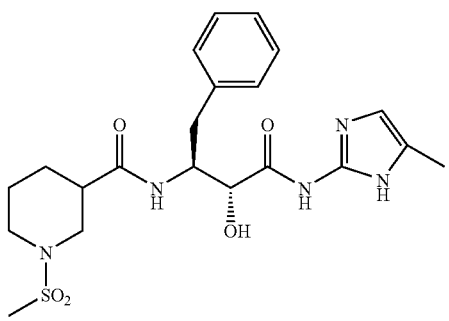

The title compound was prepared using (2R,3S)-3-amino-2-hydroxy-N-[(5-methyl-1H-imidazol-2-yl)-4-phenylbutanamide 2 hydrochloric acid salts obtained in Reference Example 35 and 1-(methylsulfonyl)piperidine-3-carboxylic acid obtained in Reference Example 36 in a similar manner to Example 22 to give 18 mg (0.04 mmol) of the compound (yield: 39%).

MS (LC/MS): 464 [M+H]+

$^1$H-NMR (400 MHz, DMSO-$d_6$): δ 1.13-1.24 (m, 2H), 1.32-1.43 (m, 1H), 1.53-1.68 (m, 2H), 2.05 (s, 3H), 2.33-2.39 (m, 2H), 2.68-2.91 (m, 7H), 3.45 (d, 2H, J=7.56 Hz) 4.06 (br, 1H), 4.31-4.37 (m, 1H), 5.95 (br, 1H), 6.41 (br, 1H), 7.18-7.27 (m, 6H), 7.80 (t, 1H, J=8.92 Hz), 10.28 (br, 1H), 11.23 (br, 1H).

Example 27

Benzyl (2S)-2-[({(1S,2R)-1-benzyl-2-hydroxy-3-[(5-methyl-1H-imidazol-2-yl)amino]-3-oxopropyl}amino)carbonyl]pyrrolidine-1-carboxylate

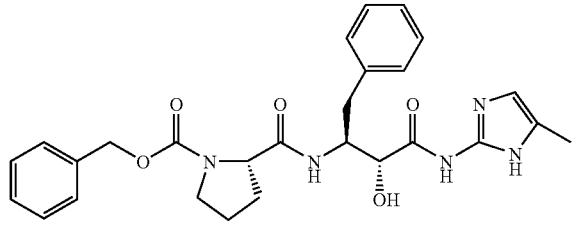

The title compound was prepared using (2R,3S)-3-amino-2-hydroxy-N-[(5-methyl-1H-imidazol-2-yl)-4-phenylbutanamide 2 hydrochloric acid salts obtained in Reference Example 35 and 1-[(benzyloxy)carbonyl]-L-proline in a similar manner to Example 22 to give 24 mg (0.05 mmol) of the compound (yield: 48%).

MS (LC/MS): 506 [M+H]$^+$ $^1$H-NMR (400 MHz, DMSO-d$_6$): δ 1.56-1.62 (m, 3H), 1.84-1.99 (m, 1H), 2.05 (s, 3H), 2.59-2.88 (m, 2H), 3.96 (br, 1H), 4.15-4.24 (m, 1H), 4.34-4.38 (m, 1H), 4.82-5.11 (m, 2H), 6.01 (br, 1H), 6.41 (s, 1H), 7.16-7.37 (m, 6H), 7.73-7.80 (m, 1H), 10.16 (br, 1H), 11.21 (br, 1H).

Example 28

N-[2-({(1S,2R)-1-Benzyl-2-hydroxy-3-[(5-methyl-1H-imidazol-2-yl)amino]-3-oxopropyl}amino)-2-oxoethyl]-2-furamide

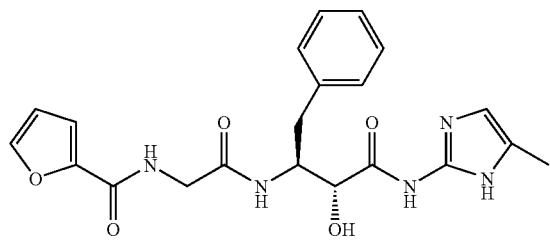

The title compound was prepared using (2R,3S)-3-amino-2-hydroxy-N-[(5-methyl-1H-imidazol-2-yl)-4-phenylbutanamide 2 hydrochloric acid salts obtained in Reference Example 35 and N-2-furoylglycine in a similar manner to Example 22 to give 22 mg (0.05 mmol) of the compound (yield: 52%).

MS (LC/MS): 426 [M+H]$^+$ $^1$H-NMR (400 MHz, DMSO-d$_6$): δ 2.06 (s, 3H), 2.71-2.76 (m, 1H), 2.83-2.89 (m, 1H), 3.71-3.84 (m, 2H), 4.02 (br, 1H), 4.31-4.36 (m, 1H), 6.09 (br, 1H), 6.43 (br, 1H), 6.61 (s, 1H), 7.11 (d, 1H, J=3.16 Hz), 7.18-7.31 (m, 5H), 7.78 (d, 1H, J=8.84 Hz), 8.34 (t, 1H, J=5.76 Hz), 10.24 (br, 1H), 11.18 (br, 1H).

Reference Example 37

N-α-Butoxycarbonyl-trans-4-(3-chlorophenoxy)-L-proline methylester

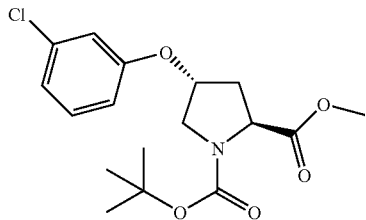

To a mixture of N-α-butoxycarbonyl-cis-4-hydroxy-L-proline methylester 123 mg (0.50 mmol), 3-chlorophenol 0.058 ml (0.55 mmol), triphenylphosphine 184 mg (0.70 mmol) and tetrahydrofuran 2 ml was added diisopropyl azodicarboxylate 0.150 ml (0.75 mmol) dropwise under ice-cooling and the mixture was stirred at room temperature for 16 hours. The reaction solution was concentrated and the residue was purified by a column chromatography on silica gel (eluted with a mixed solvent of ethyl acetate and hexane) to give 155 mg (0.44 mmol) of the title compound (yield: 87%).

$^1$H-NMR (400 MHz, CDCl$_3$): δ 1.42 (s, 9H), 2.19-2.27 (m, 1H), 2.47-2.59 (m, 1H), 3.74-3.80 (m, 5H), 4.38-4.53 (m, 1H), 4.88 (s, 1H), 6.72-6.78 (m, 1H), 6.86 (s, 1H), 6.94-6.99 (m, 1H), 7.18-7.24 (m, 1H).

Example 29

(4R)—N-{1-Benzyl-2-hydroxy-3-[(5-methyl-1H-imidazol-2-yl)amino]-3-oxopropyl}-4-(3-chlorophenoxy)-L-prolineamide

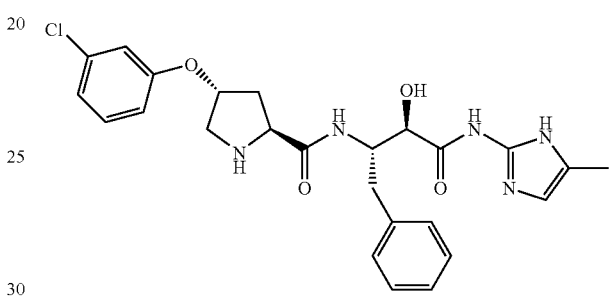

A mixture of N-α-butoxycarbonyl-trans-4-(3-chlorophenoxy)-L-proline methylester obtained in Reference Example 37 18 mg (0.050 mmol), methanol 0.2 ml, tetrahydrofuran 0.2 ml and 2N aqueous sodium hydroxide solution 0.2 ml was stirred at room temperature for 16 hours. The reaction solution was concentrated and adjusted with 1N hydrochloric acid to pH=5. The mixture was extracted with ethyl acetate and dried on magnesium sulfate. After filtration and concentration of the mixture, to the residue were added (2R,3S)-3-amino-2-hydroxy-N-[(5-methyl-1H-imidazol-2-yl)-4-phenylbutanamide 2 hydrochloric acid salts obtained in Reference Example 35 19 mg (0.050 mmol), HBTU 21 mg (0.055 mmol), DMF 1.0 ml and triethylamine 0.032 ml (0.23 mmol) and the mixture was stirred at room temperature for 16 hours. The reaction solution was extracted by adding ethyl acetate and saturated aqueous sodium bicarbonate solution and dried on magnesium sulfate. After evaporation of the solvent, thereto was added 4N hydrochloric acid/dioxane 1 ml under ice-cooling and the mixture was stirred at room temperature for 2 hours. After concentration, the mixture was purified by HPLC fraction collector to give the title compound.

MS (LC/MS): 498 [M+H]$^+$ $^1$H-NMR (400 MHz, DMSO-d$_6$): δ 1.84-1.94 (m, 1H), 2.19 (s, 3H), 2.52-2.59 (m, 1H), 2.72-2.82 (m, 1H), 2.94-3.01 (m, 1H), 3.50-3.55 (m, 1H), 4.29 (s, 2H), 4.40-4.49 (m, 1H), 5.15 (t, 1H, J=4.2 Hz), 6.80 (s, 1H), 6.92-7.00 (m, 2H), 7.02-7.05 (m, 2H), 7.07-7.11 (m, 1H), 7.22-7.25 (m, 2H), 7.31 (d, 2H, J=4.4 Hz), 7.37 (t, 1H, J=8.2 Hz), 8.82 (d, 12H, J=8.4 Hz).

Reference Example 38

N-α-Butoxycarbonyl-trans-4-[(4-methylphenyl)sulfonyl]amino-L-proline methylester

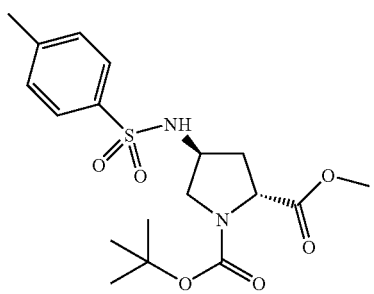

A 3 ml solution of N-α-butoxycarbonyl-trans-4-amino-L-proline methylester 49 mg (0.20 mmol), triethylamine 0.042 ml (0.30 mmol), p-toluenesulfonyl chloride 42 mg (0.22 mmol) in chloroform was stirred at room temperature for 16 hours. To the reaction solution was added water and the mixture was extracted with chloroform and dried on magnesium sulfate. After filtration and concentration of the mixture, the residue was purified by a column chromatography on silica gel (eluted with a mixed solvent of ethyl acetate and hexane) to give 64 mg (0.16 mmol) of the title compound (yield: 80%).

$^1$H-NMR (400 MHz, CDCl$_3$): δ 1.38 (s, 9H), 2.05-2.29 (m, 2H), 2.44 (s, 3H), 3.11-3.17 (m, 1H), 3.56-3.64 (m, 1H), 3.71 (s, 3H), 3.89-3.97 (m, 1H), 4.24-4.35 (m, 1H), 4.66-4.76 (m, 1H), 7.32 (d, 2H, J=7.3 Hz), 7.74 (d, 2H, J=8.0 Hz).

Example 30

(4R)—N-{1-Benzyl-2-hydroxy-3-[(5-methyl-1H-imidazol-2-yl)amino]-3-oxopropyl}-4-[(4-methylphenyl)sulfonyl]amino-L-prolineamide

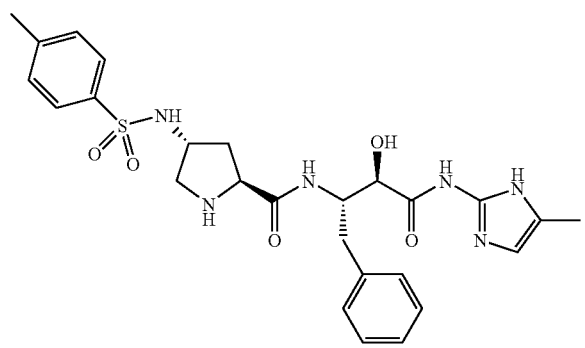

The title compound was prepared using N-α-butoxycarbonyl-trans-4-[(4-methylphenyl) sulfonyl]amino-L-proline methylester obtained in Reference Example 38 20 mg (0.050 mmol) in a similar manner to Example 29.

MS (LC/MS): 541 [M+H]$^+$ $^1$H-NMR (400 MHz, DMSO-d$_6$): δ 1.81-1.91 (m, 1H), 2.18 (s, 3H), 2.21-2.35 (m, 1H), 2.39 (s, 3H), 2.71-2.81 (m, 1H), 2.84-3.00 (m, 2H), 3.03-3.10 (m, 1H), 3.58-3.63 (m, 1H), 4.17-4.30 (m, 2H), 4.32-4.44 (m, 1H), 6.79 (s, 1H), 6.96 (s, 1H), 7.18-7.23 (m, 2H), 7.29 (d, 2H, J=4.4 Hz), 7.42 (d, 2H, J=8.0 Hz), 7.68 (d, 2H, J=8.2 Hz), 8.14 (d, 2H, J=5.8 Hz), 8.67 (d, 2H, J=9.2 Hz).

Example 31

(2R,3S)-3-{[4-(4-hexylphenyl)-4-oxobutanoyl]amino}-2-hydroxy-N-1H-imidazol-2-yl-4-phenylbutanamide

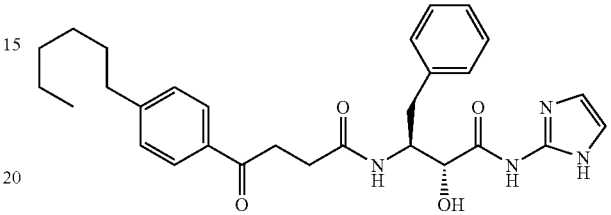

The title compound was prepared using (2R,3S)-3-amino-2-hydroxy-N-1H-imidazol-2-yl-4-phenylbutanamide 2 hydrochloric acid salts obtained in Reference Example 3 and 4-(4-hexylphenyl)-4-oxobutanoic acid in a similar manner to Example 22 to give 23 mg (0.05 mmol) of the compound (yield: 46%).

MS (LC/MS): 505 [M+H]$^+$ $^1$H-NMR (400 MHz, DMSO-d$_6$): δ 0.85 (t, 3H, J=6.76 Hz), 1.27 (br, 3H), 1.58 (t, 2H, J=6.84 Hz), 2.34-2.42 (m, 2H), 2.63 (t, 2H, J=7.44 Hz), 2.72-2.78 (m, 1H), 2.84-2.90 (m, 1H), 3.00-3.04 (m, 2H), 4.05 (br, 1H), 4.30-4.37 (m, 1H), 6.06 (br, 1H), 6.74 (br, 1H), 7.20-7.32 (m, 6H), 7.77-7.80 (m, 3H), 10.37 (br, 1H), 11.51 (br, 1H).

Example 32

(2R,3S)-3-({(2E)-3-[4-(Benzyloxy)-3-methoxyphenyl]prop-2-enoyl}amino}-2-hydroxy-N-1H-imidazol-2-yl-4-phenylbutanamide

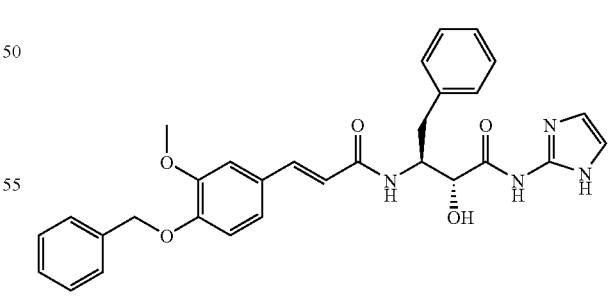

The title compound was prepared using (2R,3S)-3-amino-2-hydroxy-N-1H-imidazol-2-yl-4-phenylbutanamide 2 hydrochloric acid salts obtained in Reference Example 3 and (2E)-3-[4-(benzyloxy)-3-methoxyphenyl]acrylic acid in a similar manner to Example 22 to give 24 mg (0.05 mmol) of the compound (yield: 46%).

MS (LC/MS): 527 [M+H]+

$^1$H-NMR (400 MHz, DMSO-$d_6$): δ 2.78-2.84 (m, 1H), 2.90-2.93 (m, 1H), 3.80 (s, 3H), 4.12 (br, 1H), 4.48-4.54 (m, 1H), 5.10 (s, 2H), 6.11 (br, 1H), 6.60 (s, 1H), 6.71 (br, 2H), 7.03-7.45 (m, 14H), 7.83 (d, 1H, J=9.00 Hz), 10.45 (br, 1H), 11.51 (br, 1H).

Example 33

(2R,3S)-3-{[({4-Chloro-6-[(2,3-dimethylphenyl)amino]pyrimidin-2-yl}thio)acetyl]amino}-2-hydroxy-N-1H-imidazol-2-yl-4-phenyl butanamide

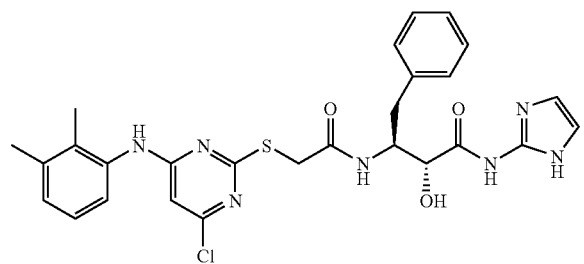

The title compound was prepared using (2R,3S)-3-amino-2-hydroxy-N-1H-imidazol-2-yl-4-phenylbutanamide 2 hydrochloric acid salts obtained in Reference Example 3 and ({4-chloro-6-[(2,3-dimethylphenyl)amino]pyridine-2-yl}thio)acetic acid in a similar manner to Example 22 to give 22 mg (0.04 mmol) of the compound yield: 39%).

MS (LC/MS): 567 [M+H]+

$^1$H-NMR (400 MHz, DMSO-$d_6$): δ 2.06 (s, 3H), 2.26 (s, 3H), 2.67-2.73 (m, 1H), 2.81-2.91 (m, 1H), 3.62 (d, 1H, J=14.68 Hz), 3.74 (d, 1H, J=14.68 Hz), 4.05 (br, 1H), 4.30-4.36 (m, 1H), 6.09 (br, 1H), 6.71 (br, 2H), 7.02-7.34 (m, 8H), 7.87 (d, 1H, J=8.88 Hz), 9.58 (br, 1H), 10.39 (br, 1H), 11.35 (br, 1H).

Example 34

(2R,3S)-3-{[4-(4-Butoxyphenyl)-4-oxobutanoyl]amino}-2-hydroxy-N-1H-imidazol-2-yl-4-phenylbutanamide

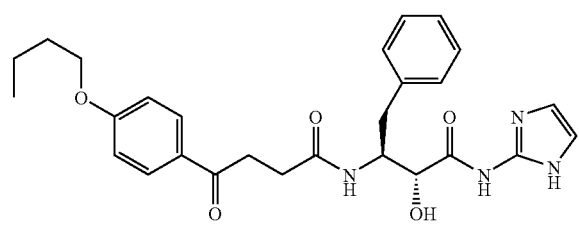

The title compound was prepared using (2R,3S)-3-amino-2-hydroxy-N-1H-imidazol-2-yl-4-phenylbutanamide 2 hydrochloric acid salts obtained in Reference Example 3 and 4-(4-butoxyphenyl)-4-oxobutanoic acid in a similar manner to Example 22 to give 21 mg (0.04 mmol) of the compound (yield: 43%).

MS (LC/MS): 493 [M+H]+

$^1$H-NMR (400 MHz, DMSO-$d_6$): δ 0.94 (t, 3H, J=7.36 Hz), 1.39-1.49 (m, 2H), 1.68-1.75 (m, 2H), 2.32-2.40 (m, 2H), 2.73-2.78 (m, 1H), 2.85-2.90 (m, 1H), 2.98 (t, 2H, J=6.84 Hz), 4.06 (m, 3H), 4.31-4.36 (m, 1H), 6.07 (br, 1H), 6.76 (br, 1H), 7.00 (d, 2H, J=8.84 Hz), 7.19-7.37 (m, 5H), 7.77 (d, 1H, J=9.00 Hz), 7.83 (d, 2H, J=8.80 Hz), 8.15 (s, 1H), 8.31 (d, 1H, J=8.96 Hz), 8.99 (d, 1H, J=7.92 Hz), 10.67 (br, 1H), 11.21 (br, 1H).

Reference Example 39

(2R,3S)-2-Hydroxy-3-{[3-[methyl(methylsulfonyl)amino]-5-({[(1R)-1-phenylethyl]amino}carbonyl)benzoyl]amino}-4-phenylbutanoic acid

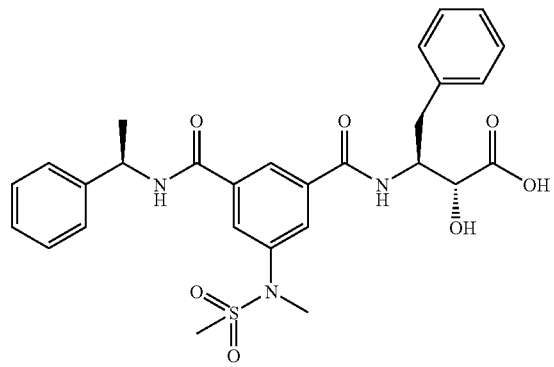

To a 10 ml solution of (2R,3S)-2-hydroxy-3-{[3-[methyl(methylsulfonyl)amino]-5-({[(1R)-1-phenylethyl]amino}carbonyl)-benzoyl]amino}-4-phenylbutanoic acid methylester 775 mg (1.37 mmol) in methanol was added 1N aqueous sodium hydroxide solution 1.64 ml and the mixture was stirred at room temperature for 5 hours. After distilling methanol off, the mixture was washed with ether. The mixture was adjusted with 1N hydrochloric acid to pH 3 under ice-cooling and the mixture was extracted with ethyl acetate. The organic layer was washed with an aqueous saturated sodium chloride solution and dried on magnesium sulfate, filtered and concentrated to give the title compound 730 mg (1.32 mmol) (yield 96%).

Example 35

N-((1S,2R)-1-Benzyl-2-hydroxy-3-{[5-(2-methoxyethyl)-1H-imidazol-2-yl]amino}-3-oxopropyl)-5-[methyl(methylsulfonyl)amino]-N'-[(1R)-1-phenylethyl]isophthalamide

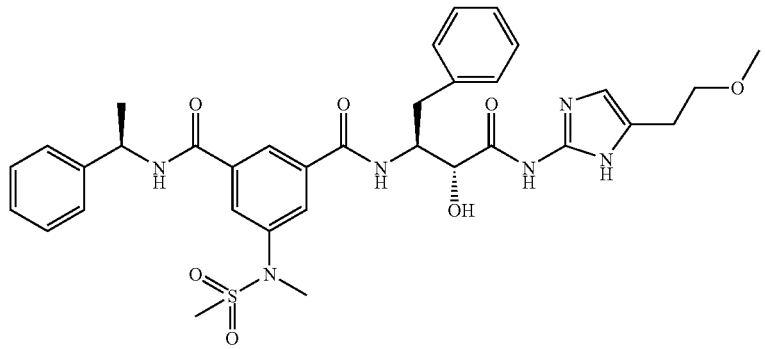

To a 0.5 ml solution of benzyl 2-amino-4-(2-methoxyethyl)-1H-imidazole-1-carboxylate prepared in a similar manner to Example 32 63 mg (0.22 mmol), (2R,3S)-2-hydroxy-3-{[3-[methyl(methylsulfonyl)amino]-5-({[(1R)-1-phenylethyl]amino}carbonyl)benzoyl]amino}-4-phenylbutanoic acid obtained in Reference Example 39 63 mg (0.11 mmol) and HOBt —H$_2$O 18 mg (0.12 mmol) in DMF was added EDC.HCl 23 mg (0.12 mmol) under ice-cooling and the mixture was heated to room temperature and stirred for 2 hours. The reaction solution then was extracted by adding ethyl acetate and 5% aqueous sodium carbonate solution. The organic layer was washed with an aqueous saturated sodium chloride solution and dried on sodium sulfate. Filtration and concentration gave a residue and the resulting residue was redissolved in methanol 2 ml and thereto were added ammonium formate 126 mg (2.00 mmol) and 10% Pd/C (containing 50%) 50 mg and the mixture was heated under reflux for 1.5 hours. The mixture was filtered to remove 10% Pd/C and concentrated. The concentrated residue was suspended in ethyl acetate and the mixture was washed with 5% sodium carbonate and an aqueous saturated sodium chloride solution. The organic layer was dried on sodium sulfate. After filtration and concentration of the mixture, the mixture was purified by a column chromatography on silica gel (eluted with a mixed solvent of chloroform and methanol) to give 50 mg (0.07 mmol) of the title compound (yield: 67%).

MS (LC/MS): 677 [M+H]$^+$ $^1$H-NMR (400 MHz, DMSO-d$_6$): δ 1.49 (d, 3H, J=7.04 Hz), 2.66 (br, 2H), 2.88-3.03 (m, 5H), 3.21 (s, 3H), 3.26 (s, 3H), 3.47 (t, 2H, J=6.84 Hz), 4.20 (br, 1H), 4.59-4.65 (m, 1H), 5.17 (5, 1H, J=7.44 Hz), 5.95 (br, 1H), 6.47 (br, 1H), 7.14-7.40 (m, 10H), 7.84 (s, 1H), 7.95 (s, 1H), 8.15 (s, 1H), 8.31 (d, 1H, J=8.96 Hz), 8.99 (d, 1H, J=7.92 Hz), 10.67 (br, 1H), 11.21 (br, 1H).

Example 36

N-[(1S,2R)-1-Benzyl-3-({5-[2-(benzyloxy)ethyl]-1H-imidazol-2-yl}amino)-2-hydroxy-3-oxopropyl]-5-[methyl(methylsulfonyl)amino]-N'-[(1R)-1-phenylethyl]isophthalamide

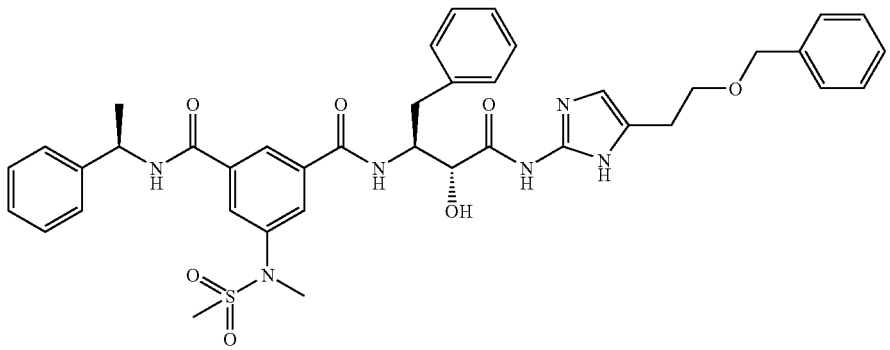

The title compound was prepared using benzyl 2-amino-4-[2-(benzyloxy)ethyl]-1H-imidazole-1-carboxylate obtained in a similar manner to Reference Example 32 in a similar manner to Example 35 to give 151 mg (0.20 mmol) of the compound (yield: 80%).

MS (LC/MS): 753 [M+H]$^+$ $^1$H-NMR (400 MHz, DMSO-d$_6$): δ 1.49 (d, 3H, J=7.04 Hz), 2.66 (br, 2H), 2.89-3.01 (m, 5H), 3.25 (s, 3H), 3.58 (t, 2H, J=7.04 Hz), 4.19 (br, 1H), 4.46 (s, 2H), 4.56-4.62 (br, 1H), 5.17 (5, 1H, J=7.28 Hz), 5.98 (br, 1H), 6.48 (br, 1H), 7.14-7.39 (m, 15H), 7.84 (s, 1H), 7.96 (s, 1H), 8.15 (s, 1H), 8.34 (d, 1H, J=6.08 Hz), 9.01 (d, 1H, J=7.60 Hz), 10.72 (br, 1H), 11.19 (br, 1H).

Example 37

N-[(1S,2R)-1-Benzyl-2-hydroxy-3-({5-[2-(methyl-sulfonyl)ethyl]-1H-imidazol-2-yl}amino)-3-oxopropyl]-5-[methyl(methylsulfonyl)amino]-N'-[(1R)-1-phenylethyl]isophthalamide

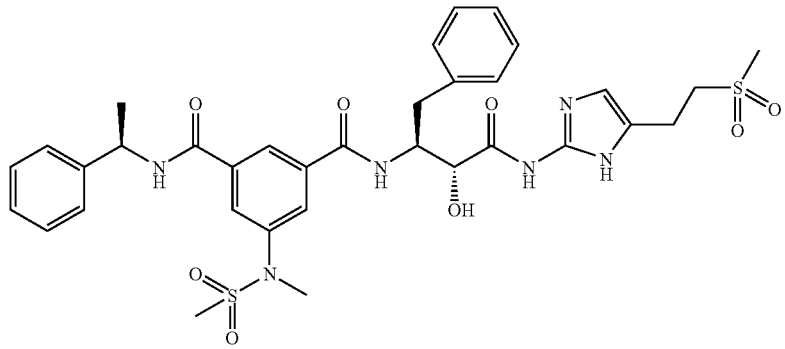

Benzyl 2-amino-4-[2-(methylsulfonyl)ethyl]-1H-imidazole-1-carboxylate was prepared in a similar manner to Reference Example 32 and the title compound was prepared in a similar manner to Reference Example 35 in 12 mg (0.02 mmol) (yield: 62%).

MS (LC/MS): 725 [M+H]$^+$ $^1$H-NMR (400 MHz, DMSO-d$_6$): δ 1.49 (d, 3H, J=7.08 Hz), 2.83 (br, 2H), 2.93-3.00 (m, 8H), 3.27 (s, 3H), 4.22 (br, 1H), 4.59-4.66 (m, 1H), 5.17 (5, 1H, J=7.28 Hz), 5.98 (br, 1H), 6.59 (br, 1H), 7.14-7.40 (m, 10H), 7.84 (s, 1H), 7.96 (s, 1H), 8.14 (s, 1H), 8.32 (d, 1H, J=9.08 Hz), 8.99 (d, 1H, J=7.92 Hz), 10.73 (br, 1H), 11.30 (br, 1H).

Example 38

N-[(1S,2R)-1-Benzyl-2-hydroxy-3-({5-[(methylsulfonyl)methyl]-1H-imidazol-2-yl}amino)-3-oxopropyl]-5-[methyl(methylsulfonyl)amino]-N'-[(1R)-1-phenylethyl]isophthalamide

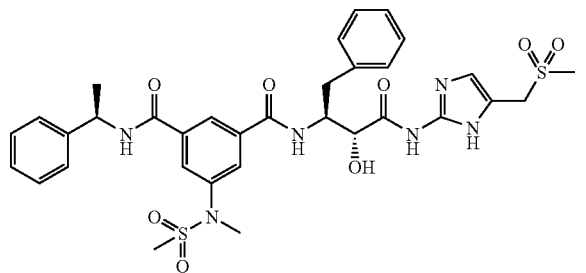

Benzyl 2-amino-4-[(methylsulfonyl)methyl]-1H-imidazole-1-carboxylate was prepared in a similar manner to Reference Example 32 and the title compound was prepared in a similar manner to Reference Example 35 in 32 mg (0.05 mmol) (yield: 45%).

MS (LC/MS): 711 [M+H]$^+$ $^1$H-NMR (400 MHz, DMSO-d$_6$): δ 1.23 (s, 3H), 1.49 (d, 3H, J=7.04 Hz), 2.92-3.02 (m, 8H), 4.21 (s, 2H), 4.62-4.65 (m, 1H), 5.17 (5, 1H, J=7.40 Hz), 5.96 (br, 1H), 6.82 (s, 1H), 7.14-7.39 (m, 11H), 7.85 (s, 1H), 7.95 (s, 1H), 8.15 (s, 1H), 8.33 (d, 1H, J=8.80 Hz), 8.99 (d, 1H, J=7.80 Hz), 10.92 (br, 1H), 11.59 (br, 1H).

Testing Example 1

Measurement of β Secretase Inhibitory Activity

To a 96 well black plate (Corning Inc.) were added 20 μL of a 0.5% solution of test compound in DMSO diluted with 0.2 M acetate buffer (pH 4.5) and 40 μL of Dabcyl-Ser-Glu-Val-Asn-Lue-Asp-Ala-Glu-Phe-Arg-Glu(Edans)-(D)Arg-(D)Arg-NH$_2$ (Peptide Institute) in a final concentration of 30 μM. The enzymatic reaction was performed by adding a 40 μL of a 0.5 μg/mL of a recombinant human BACE-1 (R&D systems) and incubating for 2 hours at 37° C. Before and after the incubation, the fluorescence intensity (excitation wavelength: 355 nm; measured wavelength: 500 nm) was measured using a fluorescence plate reader (SPECTRA MAX GEMINI XS, Molecular Devices inc.). The increasing amount between the measurements obtained before incubation and after incubation was calculated. The effect on the β secretase inhibitory activity by the test compound is shown by an inhibitory ratio when compared increasing amount in the test compound with that of the control group wherein the increasing amount measured when only DMSO is added being defined as 100%.

As the result of the testing, compounds given in all Examples were shown to exhibit an IC$_{50}$ value of 10 to 10000 nM.

Testing Example 2

Measurement of Effects on an Activity of Inhibiting a Production and Secretion of Aβ by the Compounds of the Present Invention in a Human Neuroblastoma IMR-32 Cell 1) Incubation of IMR-32 Cell IMR-32 cells (American Type Culture Collection Inc.) were seeded to 35 mmφPetri dish (FALCON Ltd.) at 37° C. for 2 to 3 days at 1.5×10$^5$ cells/petri dish. A DMSO solution containing test compound was dissolved in a 0.2% bovine serum albumin (Sigma Inc.)/Dulbecco's modified Eagle medium (Sigma Inc.), and a 1 mL of the mixture was added to the above Petri dish and the mixture was incubated for additional 24 hours. A 0.2% bovine serum albumin/Dulbecco's modified Eagle medium without the test compound was used as a control. The supernatant was collected and centrifuged at 5000 rpm for 5 minutes to precipitate a suspension cell. After centrifugation, the supernatant was used as a measurement sample of Aβ.

(2) Determination by Enzyme-Linked Immunoassay (ELISA) of Aβ

To a maxi sorp 96 well plate (Nunc Inc.) was added 50 μL portions of 4G8 antibody (Sigma Inc.) dissolved in 0.1M carbonate buffer (pH 9.5) and the mixture was allowed to stand at 4° C. overnight. The mixture was washed twice with phosphate/saline buffer (phosphate buffered saline, hereinafter abbreviated as PBS) and the mixture was blocked by 100 μL of 25% BlockAse (Dainippon Pharmaceuticals Co. Ltd.). After washing three times with 0.02% Tween 20/PBS (hereinafter abbreviated as PBST), thereto were added 50 μL of the supernatant aforementioned in (1) or Aβ(1-40) standard (Sigma Inc.) diluted with 25% BlockAse/PBS and Biotinylated 6E10 antibody (Signet Inc.) diluted with 25% BlockAse/PBS, and the mixture was allowed to stand at 4° C. overnight and more. After washing three times with PBST, thereto was added 50 μL of horseradish peroxidase labeled streptavidin (Amersham Biosciences, Inc.) diluted with 10% BlockAse/PBS and the mixture was allowed to stand at room temperature for 1 hour. After washing three times with PBST, color was developed by TMB substrate kit (Pias Inc.) and the calorimetric method (measured wavelength: 450 nm) was determined by a plate reader (ELx 808, BIO-TEK INSTRUMENTS Inc.).

As the result of the testing, the compound given in Example 1 was shown to exhibit an $IC_{50}$ value of 200 nM.

INDUSTRIAL APPLICABILITY

The present compound containing hydroxymethylcarbonyl structure and or a pharmaceutically acceptable salt thereof can be used as an agent for preventing or treating Alzheimer's disease.

The invention claimed is:

1. A compound represented by the general formula (1):

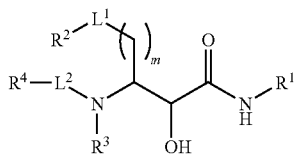

(1)

wherein
$R^1$ is a group of the formula (2):

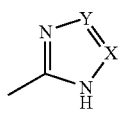

(2)

wherein X is a nitrogen atom or a group of the formula: $C(R^5)$,
Y is a nitrogen atom or a group of the formula: $C(R^6)$,
$R^5$ and $R^6$ are each independently a hydrogen atom, a halogen atom, a carboxyl group, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted, saturated or unsaturated aliphatic heterocyclic group, a substituted or unsubstituted aryl group, a substituted or unsubstituted aromatic heterocyclic group, a substituted or unsubstituted alkoxycarbonyl group, or a substituted or unsubstituted amino group, or alternatively $R^5$ and $R^6$ may combine together with the carbon atoms to which they bind, to form a substituted or unsubstituted cyclopentene ring, a substituted or unsubstituted cyclohexane ring, a substituted or unsubstituted benzene ring, or a substituted or unsubstituted pyridine ring; or a group of the formula (3):

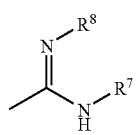

(3)

wherein $R^7$ is a hydrogen atom, a substituted or unsubstituted alkyl group, or a group of the formula: $C(=O)R^9$ or $C(=S)R^9$ (wherein $R^9$ is a substituted or unsubstituted alkyl group), $R^8$ is a hydrogen atom or a substituted or unsubstituted alkyl group, or alternatively $R^7$ and $R^8$ may combine to form a group of the formula: $—[C(R^{10})(R^{11})]_n—$, $—C(=O)[C(R^{10})(R^{11})]_p—$ or $—C(=S)[C(R^{10})(R^{11})]_p—$ (wherein $R^{10}$ and $R^{11}$ are each independently a hydrogen atom or a substituted or unsubstituted alkyl group, n is an integer of 2 to 4 and p is an integer of 1 to 3, or when n or p is more than 1, two or more $R^{10}$ and two or more $R^{11}$ may be each independently the same or different group);

m is an integer of 1 to 6, $L^1$ is a single bond, an oxygen atom or a sulfur atom, $R^2$ is a hydrogen atom, a substituted or unsubstituted alkyl group, a substituted or unsubstituted cycloalkyl group, a substituted or unsubstituted cycloalkenyl group, a substituted or unsubstituted, saturated or unsaturated aliphatic heterocyclic group, a substituted or unsubstituted aryl group, or a substituted or unsubstituted aromatic heterocyclic group, $R^3$ is a hydrogen atom or a substituted or unsubstituted alkyl group, $L^2$ is a single bond or a group selected from following formulae (a) to (n):

$—[C(R^{12})(R^{13})]_q—$, (a)

$—C(=O)—$, (b)

$—[C(R^{12})(R^{13})]_q—C(=O)—$, (c)

$—O—[C(R^{12})(R^{13})]_q—C(=O)—$, (d)

$—S—[C(R^{12})(R^{13})]_q—C(=O)—$, (e)

$—N(R^{14})—[C(R^{12})(R^{13})]_q—C(=O)—$, (f)

$—[N(R^{14})—C(R^{12})(R^{13})—C(=O)]_r—$, (g)

$—[C(R^{12})(R^{13})]_s—O—C(=O)—$, (h)

$—[C(R^{12})(R^{13})]_s—N(R^{14})—C(=O)—$, (i)

$—[C(R^{12})(R^{13})]_s—N(R^{14})—C(=S)—$, (j)

—S(=O)₂—,  (k)

—C(R¹²)=C(R¹³)—C(=O)—,  (l)

—C(=O)—N(R¹⁴)—C(R¹²)(R¹³)—C(=O)—,  (m)

—C(=O)—[C(R¹²)(R¹³)]_q—C(=O)—  (n)

wherein R¹², R¹³ and R¹⁴ are each independently a hydrogen atom or a substituted or unsubstituted alkyl group, q is an integer of 1 to 6, r is 2 or 3, s is an integer of 0 to 6, and when q, r or s is more than 1, two or more R¹², two or more R¹³ and two or more R¹⁴ may be each independently the same or different group;

R⁴ is a hydrogen atom, a substituted or unsubstituted, saturated or unsaturated aliphatic heterocyclic group, a substituted or unsubstituted aryl group, or a substituted or unsubstituted aromatic heterocyclic group, or a pharmaceutically acceptable salt thereof.

2. The compound according to claim 1 or a pharmaceutically acceptable salt thereof, wherein R² is a hydrogen atom, a substituted or unsubstituted cycloalkyl group, a substituted or unsubstituted cycloalkenyl group, a substituted or unsubstituted, saturated or unsaturated aliphatic heterocyclic group, a substituted or unsubstituted aryl group, or a substituted or unsubstituted aromatic heterocyclic group, L² is a single bond or a group selected from the following formulae (a) to (e) and (i) to (n):

—[C(R¹²)(R¹³)]_q—,  (a)

—C(=O)—,  (b)

—[C(R¹²)(R¹³)]_q—C(=O)—,  (c)

—O—[C(R¹²)(R¹³)]_q—C(=O)—,  (d)

—S—[C(R¹²)(R¹³)]_q—C(=O)—,  (e)

—[C(R¹²)(R¹³)]_s—N(R¹⁴)—C(=O)—,  (i)

—[C(R¹²)(R¹³)]_s—N(R¹⁴)—C(=S)—,  (j)

—S(=O)₂—,  (k)

—C(R¹²)=C(R¹³)—C(=O)—,  (l)

—C(=O)—N(R¹⁴)—C(R¹²)(R¹³)—C(=O)—,  (m)

—C(=O)—[C(R¹²)(R¹³)]_q—C(=O)—  (n)

wherein R¹², R¹³, R¹⁴, q and s have the same meanings as defined in claim 1, and R⁴ is a substituted or unsubstituted, saturated or unsaturated aliphatic heterocyclic group, a substituted or unsubstituted aryl group, or a substituted or unsubstituted aromatic heterocyclic group.

3. The compound according to claim 1 or 2 or a pharmaceutically acceptable salt thereof, wherein R¹ is a group of the formula (2):

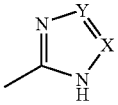

wherein X and Y have the same meanings as defined in claim 1.

4. The compound according to claim 3 or a pharmaceutically acceptable salt thereof, wherein X is a group of the formula: C(R⁵) (wherein R⁵ has the same meaning as defined in claim 1) and Y is a group of the formula: C(R⁶) (wherein R⁶ has the same meaning as defined in claim 1).

5. The compound according to claim 1 or 2 or a pharmaceutically acceptable salt thereof, wherein R¹ is a group of the formula: (3):

wherein R⁷ and R⁸ have the same meanings as defined in claim 1.

6. The compound according to claim 1 or a pharmaceutically acceptable salt thereof, wherein m is 1, L¹ is a single bond and R² is a substituted or unsubstituted aryl group.

7. The compound according to claim 1 or a pharmaceutically acceptable salt thereof, wherein L² is a group of the formula: —C(=O)— and R⁴ is a substituted or unsubstituted aryl group.

8. The compound according to claim 1 or a pharmaceutically acceptable salt thereof, wherein a compound of the formula (1) is represented by the formula (4):

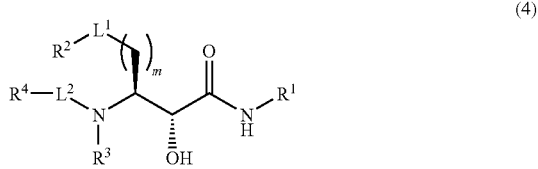

wherein R¹, R², R³, R⁴, L¹, L² and m have the same meanings as defined in claim 1.

9. A βsecretase inhibitor comprising the compound according to claim 1 or a pharmaceutically acceptable salt thereof as an active ingredient.

10. An agent for treating Alzheimer's disease, comprising the compound according to claim 1 or a pharmaceutically acceptable salt thereof as an active ingredient.

* * * * *

UNITED STATES PATENT AND TRADEMARK OFFICE
CERTIFICATE OF CORRECTION

PATENT NO. : 7,816,387 B2
APPLICATION NO. : 11/991426
DATED : October 19, 2010
INVENTOR(S) : Tsutomu Mimoto et al.

It is certified that error appears in the above-identified patent and that said Letters Patent is hereby corrected as shown below:

On the Title Page, Item (73) Assignee should read:
Item (73) Assignees: ~~Dainippon Sumitomo Pharma Co., Ltd., Osaka-Shi, Osaka (JP);~~ Yoshiaki Kiso, Ibaraki-Shi, Osaka (JP)

Signed and Sealed this
Thirteenth Day of March, 2012

David J. Kappos
*Director of the United States Patent and Trademark Office*